United States Patent
Marras et al.

(10) Patent No.: US 11,111,515 B2
(45) Date of Patent: *Sep. 7, 2021

(54) HIGHLY SELECTIVE NUCLEIC ACID AMPLIFICATION PRIMERS

(71) Applicant: Rutgers, The State University of New Jersey, New Brunswick, NJ (US)

(72) Inventors: Salvatore A. Marras, Roselle Park, NJ (US); Diana Vargas-Gold, Millburn, NJ (US); Sanjay Tyagi, New York, NY (US); Fred R. Kramer, Riverdale, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,463

(22) Filed: Oct. 23, 2020

(65) Prior Publication Data

US 2021/0164009 A1 Jun. 3, 2021

Related U.S. Application Data

(60) Continuation of application No. 15/877,007, filed on Jan. 22, 2018, now Pat. No. 10,815,512, which is a (Continued)

(51) Int. Cl.
*C12P 19/34* (2006.01)
*C12Q 1/6858* (2018.01)
*C12Q 1/686* (2018.01)

(52) U.S. Cl.
CPC .............. *C12P 19/34* (2013.01); *C12Q 1/686* (2013.01); *C12Q 1/6858* (2013.01)

(58) Field of Classification Search
CPC ........ C12Q 2525/161; C12Q 2525/191; C12Q 1/686; C12P 19/34
See application file for complete search history.

(56) References Cited

U.S. PATENT DOCUMENTS 5,866,336 A 2/1999 Nazarenko et al.
6,277,607 B1 8/2001 Tyagi et al.
(Continued)

FOREIGN PATENT DOCUMENTS

CN 102459630 A 5/2012
CN 102639712 A 8/2012
(Continued)

OTHER PUBLICATIONS

Stratagene Catalog, p. 39 (Year: 1988).*
(Continued)

*Primary Examiner* — Teresa E Strzelecka
(74) *Attorney, Agent, or Firm* — Fox Rothschild LLP

(57) ABSTRACT

This invention discloses multi-part primers for primer-dependent nucleic acid amplification methods. Also disclosed are primer-dependent nucleic acid amplification reactions, particularly DNA amplification reactions, reaction mixtures and reagent kits for such reactions. This invention relates to primer-dependent nucleic acid amplification reactions, particularly DNA amplification relations such as PCR, and primers, reaction mixtures and reagent kits for such reactions and assays employing same.

12 Claims, 19 Drawing Sheets

Specification includes a Sequence Listing.

Related U.S. Application Data division of application No. 14/766,139, filed as application No. PCT/US2014/015351 on Feb. 7, 2014, now Pat. No. 9,909,159.

(60) Provisional application No. 61/762,117, filed on Feb. 7, 2013.

(56) References Cited

U.S. PATENT DOCUMENTS

| | | |
|---|---|---|
| 8,323,895 B2 | 12/2012 | Chun |
| 2010/0221702 A1 | 9/2010 | Moser |
| 2011/0097764 A1 | 4/2011 | Johnson et al. |
| 2011/0269192 A1 | 11/2011 | Ruan et al. |
| 2012/0171673 A1 | 7/2012 | Nakamura et al. |
| 2012/0220468 A1 | 8/2012 | Chun et al. |

FOREIGN PATENT DOCUMENTS

| | | |
|---|---|---|
| CN | 102770556 A | 11/2012 |
| JP | 4528885 B1 | 8/2010 |
| WO | 2006095981 A1 | 9/2006 |
| WO | 2008111741 A1 | 9/2008 |
| WO | 2011001496 A1 | 1/2011 |
| WO | 2011050278 A1 | 4/2011 |
| WO | 2011055875 A1 | 5/2011 |
| WO | 2011078441 A1 | 6/2011 |
| WO | 2013/123552 A1 | 8/2013 |

OTHER PUBLICATIONS

Hwang et al., "Annealing control primer system for improving specificity of PCR amplification," Biotechniques (Dec. 2003); 35:1180-1184.

Chun et al., "Dual priming oligonucleotide system for the multiplex detection of respiratory viruses and SNP genotyping of CYP2C19 gene," Nucleic Acids Research (2007); 35(6):e40 (6 pages).

Weiner, et al: "Kits and Their Unique Role in Molecular Biology: A Brief Retrospective"; BioTechniques, 2008, vol. 44, pp. 701-704.

AMOYDXTM: "TP53 Six Mutations Detection Kit, Detection of Six Mutations in the TP53 Gene", 2012, pp. 1-4.

Bergstrom, et al: "Comparison of the Base Pairing Properties of a Series of Nitroazole Nucleobase Analogs in the Oligodeoxyribonucleotide Sequence 54-d(CGCXAATTYGCG)-34", Nucleic Acids Research, 1997, vol. 25, No. 10, pp. 1935-1942.

Fang, et al: "Designing a Novel Molecular Beacon for Surface-Immobilized DNA Hybridization Studies", 1999, J. Am. Chem. Soc,, vol. 121, pp. 2921-2922.

Vet, et al: "Molecular Beacons: Colorful Analysis of Nucleic Acids", 2002, Expert Rev. Mol. Diagn., vol. 2, No. 1, pp. 39-99.

Okubo, et al: "A Rapid Multiplex PCR Assay That Can Reliably Discriminate the Cytochrome P450 2D6 Whole-Gene Deletion Allele From 2D6*10 Alleles", 2012, Clinica Chimica Acta, vol. 413, pp. 1675-1677.

\* cited by examiner

A

B

A

B

SEQUENCE LISTING

```
<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
attttgggcg ggccaaactg c                                          21

<210> SEQ ID NO 2
<211> LENGTH: 95
<212> TYPE: DNA
<213> ORGANISM: Artificial Sequence
<220> FEATURE:
<223> OTHER INFORMATION: Primer

<400> SEQUENCE: 2
ccttgcatga ccacttttgt ggcgtcgtac agttctagtg tctaaaaccc gcccggtttg    60
acgacccacg ccttctcttt cttatggtac gtctt                              95
```

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gcatggtatt ctttctcttc cgca                                          24

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
caagatcaca gattttgggc g                                             21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
aagatcacag attttgggcg g                                             21

<210> SEQ ID NO 6
<211> LENGTH: 45
<212> TYPE: DNA
<213> ORGANISM: Artificial Sequence
<220> FEATURE:
<223> OTHER INFORMATION: Primer

<400> SEQUENCE: 6
ctggtgaaaa caccgcagca tgtcgcacga gtgagccctg ggcgg                   45

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
tggtgaaaac accgcagcat gtcacacgag tgagccccgg gcgg                    44

<210> SEQ ID NO 8
<211> LENGTH: 46
<212> TYPE: DNA
<213> ORGANISM: Artificial Sequence
<220> FEATURE:
<223> OTHER INFORMATION: Primer

<400> SEQUENCE: 8
actggtgaaa acaccgcagc atgttggagc tgtgagcctt gggcgg                  46

<210> SEQ ID NO 9
<211> LENGTH: 49
<212> TYPE: DNA
<213> ORGANISM: Artificial Sequence
<220> FEATURE:

<223> OTHER INFORMATION: Primer

<400> SEQUENCE: 9
cgtactggtg aaaacaccgc agcactgacg acaagtgagc cctgggcgg         49

<210> SEQ ID NO 10
<211> LENGTH: 41
<212> TYPE: DNA
<213> ORGANISM: Artificial Sequence
<220> FEATURE:
<223> OTHER INFORMATION: Primer

<400> SEQUENCE: 10
tgaaaacacc gcagcatgtc aagacactca gccctgggcg g         41

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
actggtgaaa acaccgcagc atgttgcacg agtgagcctt gggcg         45

<210> SEQ ID NO 12
<211> LENGTH: 45
<212> TYPE: DNA
<213> ORGANISM: Artificial Sequence
<220> FEATURE:
<223> OTHER INFORMATION: Primer

<400> SEQUENCE: 12
tggtgaaaac accgcagcat gtcacacgag tgagccacgg gcggg         45

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
ggtgaaaaca ccgcagcatg tcaaacgagt gagccacagg cgggc         45

<210> SEQ ID NO 14
<211> LENGTH: 45
<212> TYPE: DNA
<213> ORGANISM: Artificial Sequence
<220> FEATURE:
<223> OTHER INFORMATION: Primer

<400> SEQUENCE: 14
gtgaaaacac cgcagcatgt caaggaagtg agccacaagc gggcc         45

<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
tgaaaacacc gcagcatgtc aagacagact gacccaaacg ggcca         45

```
<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16
tgaaaacacc gcagcatgtc aagacacacg acaagtgagc cctgggcgg                49

<210> SEQ ID NO 17
<211> LENGTH: 47
<212> TYPE: DNA
<213> ORGANISM: Artificial Sequence
<220> FEATURE:
<223> OTHER INFORMATION: Primer

<400> SEQUENCE: 17
ggtgaaaaca ccgcagcatg tcaatccaac aagtgagccc tgggcgg                  47

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
tactggtgaa acaccgcag catggacgac gagccctggg cgg                       43

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
cgtactggtg aaaacaccgc agcactgacg gccctgggcg g                        41

<210> SEQ ID NO 20
<211> LENGTH: 45
<212> TYPE: DNA
<213> ORGANISM: Artificial Sequence
<220> FEATURE:
<223> OTHER INFORMATION: Primer

<400> SEQUENCE: 20
agacaactgt tcaaactgat gggaaaacac aatcatctat ttctc                    45

<210> SEQ ID NO 21
<211> LENGTH: 75
<212> TYPE: DNA
<213> ORGANISM: Artificial Sequence
<220> FEATURE:
<223> OTHER INFORMATION: Primer

<400> SEQUENCE: 21
ggtctgttga caagtttgac taccctgggt gaggtagctc taaagagaca tcgatctggt    60
tttagtggat aaaaa                                                     75

<210> SEQ ID NO 22
<211> LENGTH: 20
<212> TYPE: DNA
<213> ORGANISM: Artificial Sequence
<220> FEATURE:
```

```
<223> OTHER INFORMATION: Primer

<400> SEQUENCE: 22
ataggtgatt ttggtctagc                                              20

<210> SEQ ID NO 23
<211> LENGTH: 44
<212> TYPE: DNA
<213> ORGANISM: Artificial Sequence
<220> FEATURE:
<223> OTHER INFORMATION: Primer

<400> SEQUENCE: 23
gcctgctggg catctgcctc acctaataat ctacaacaat catg                   44

<210> SEQ ID NO 24
<211> LENGTH: 77
<212> TYPE: DNA
<213> ORGANISM: Artificial Sequence
<220> FEATURE:
<223> OTHER INFORMATION: Primer

<400> SEQUENCE: 24
cacggcggac gacccgtaga cggagtggag gtggcacgtc gagtagtacg tcgagtacgg   60
gaagccgacg gaggacc                                                 77

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
gaggcagccg aagggcatga gc                                           22

<210> SEQ ID NO 26
<211> LENGTH: 43
<212> TYPE: DNA
<213> ORGANISM: Artificial Sequence
<220> FEATURE:
<223> OTHER INFORMATION: Primer

<400> SEQUENCE: 26
ctggtgaaaa caccgcagca tgtcgcacga gtgagccctg ggc                    43

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ctggtgaaaa caccgcagca tgtc                                         24
```

HIGHLY SELECTIVE NUCLEIC ACID AMPLIFICATION PRIMERS

CROSS REFERENCE TO RELATED APPLICATIONS

This application is a continuation application, which claims priority to U.S. Nonprovisional patent application Ser. No. 15/877,007, filed on Jan. 22, 2018, now U.S. Pat. No. 10,815,512, which is a divisional application of U.S. application Ser. No. 14/766,139, filed on Aug. 6, 2015, now U.S. Pat. No. 9,909,159, issued on Mar. 6, 2018, which is a U.S. National Phase of International Patent Application No. PCT/US2014/015351, filed Feb. 7, 2014, which claims priority of U.S. Provisional Application No. 61/762,117 filed on Feb. 7, 2013. The contents of the applications are incorporated herein by reference in their entirety.

FIELD OF THE INVENTION

This invention relates to primer-dependent nucleic acid amplification reactions, particularly DNA amplification reactions such as PCR, and primers, reaction mixtures and reagent kits for such reactions and assays employing same.

BACKGROUND OF THE INVENTION

Primer-dependent nucleic acid amplification reactions, which may include detection of amplification products ("amplicons"), require "specificity," that is, annealing of a primer to the intended place in a nucleic acid strand and extension of primers bound only to the intended target sequence. Conventionally, specificity is obtained by making a primer sufficiently long so that under the amplification reaction conditions, primarily during the primer-annealing step, the primer goes to only one place in a nucleic acid strand.

Certain amplification reactions are intended to distinguish between or among allelic variants, for example, single-nucleotide polymorphisms (SNPs). One way to do that is to amplify all variants and to distinguish between or among them by allele-specific hybridization probes such as molecular beacon probes. For such an approach, the amplification primers are made equally complementary to all variants so as to amplify a region that includes the sequence that varies between or among alleles, and a probe identifies an allele that is present in the amplified product or products. See, for example, Tyagi et al. (1998) Nature Biotechnology 16:49-53. If the sequence being investigated is an allele, such as a SNP that is present in a mixture with another allele, for example, a wild-type (WT) variant, distinguishing by use of a probe has a practical detection limit of about 3% (not less than about 30,000 target allele molecules in the presence of 1,000,000 molecules of the alternate allele) due to the tendency of amplification of the prevalent allele to overwhelm amplification of the rare allele.

Another way to distinguish between or among alleles is to use a primer that is selective for the sequence being investigated. For such an approach, the primer is made complementary to the sequence that varies between or among alleles, and amplified product may be detected either by labeled primers, a DNA binding dye, or a labeled probe (in this case the probe detects a sequence common to amplicons of all alleles). A primer that is highly specific typically has a length of 15-30 nucleotides. Such a conventional primer has very limited selectivity for one allele over another. It is known that shortening a primer will improve its selectivity, but because that improvement comes at the expense of specificity, and because short primers are unlikely to form stable hybrids with their target sequence at typical annealing temperatures, shortening a primer is of limited value for analyzing mixtures of alleles.

Other modifications of primers have been developed to improve their selectivity while retaining specificity. One such approach is ARMS ("amplification refractory mutation system"). An ARMS primer has a 3'-terminal nucleotide that is complementary to the sequence variant being investigated, but that is mismatched to another allele or alleles. See Newton et al. (1989) Nucleic Acids Res. 17:2503-2516; and Ferrie et al. (1992) Am. J. Hum. Genet. 51:251-262. ARMS relies on the refractory nature of certain DNA polymerases, that is, a tendency not to extend a primer-target hybrid having such a mismatch. ARMS has been demonstrated to be useful for determining zygosity (homozygous WT, heterozygous, or homozygous mutant (MUT)), but it has a practical detection limit for other uses of about 1% (not less than about 10,000 target allele molecules in the presence of 1,000,000 molecules of the alternate allele).

Another approach is to make a primer into a hairpin to increase its selectivity. See Tyagi et al. European patent EP 1 185 546 (2008), which discloses making the hairpin loop complementary to the sequence being investigated but mismatched to another allele or alleles; and Hazbón and Alland (2004) J. Clin. Microbiol. 42:1236-1242, which discloses making the terminal nucleotide of the 3' arm of the hairpin primer complementary to the sequence variant being investigated but that is mismatched to another allele or alleles, as with ARMS. These modifications also have practical detection limits of about 1% (not less than about 10,000 target allele molecules in the presence of 1,000,000 molecules of the alternate allele).

Jong-Yoon Chun and his colleagues at the Seegene Institute of Life Science in Seoul, South Korea, have devised a type of primer that they refer to as a "dual-priming oligonucleotide (DPO)." See, Chun et al. (2007) Nucleic Acids Res. 35 (6) e40; Kim et al. (2008) J. Virol. Meth. 149:76-84; Horii et al. (2009) Lett. Appl. Microbiol. 49:46-52; WO 2006/095981 A1; and WO 2007/097582 A1. A DPO primer consists of three segments: a long 5' high-temperature segment, for example, 20-25 nucleotides in length, a central separation segment of five deoxyriboinosines, and a 3' priming segment, generally 8-12 nucleotides in length, that is complementary to the intended target sequence but mismatched to other target sequences. The target sequence is complementary to all three segments, but the Tm of the 3' segment is lower than the Tm of the 5' segment, due to its shorter length, and the separation segment has the lowest Tm due to the five deoxyriboinosines. A DPO primer is designed such that amplification results only if both the 5' segment and the 3' segment hybridize to a target strand. According to Chun et al. (2007), the separation segment was selected to be five deoxyriboinosines, because 3-4 and 6-8 deoxyriboinosines did not give results as good; the 3' segment was positioned so as to provide a GC content of 40-80%, and the 5' segment was provided a length sufficient to raise its Tm above the annealing temperature to be used in 3'-RACE amplifications (Nucleic Acids Res. 35(6) e40 at page 2). Chun et al. reports successful genotyping (homozygous wild type, heterozygous, or homozygous mutant) of a SNP (G→A mutation) in the CYP2C19 gene using two pairs of DPO primers. Of the four DPO primers, one had a 3' segment 12-nucleotides long, perfectly complementary to both alleles; one had a 3' segment 9-nucleotides long, perfectly complementary to both alleles; and two had 3' segments 8-nucleotides long with the variable nucleotide located in the middle, that is, at the fourth nucleotide position from the 3' end. Genotyping was accomplished by means of gel electrophoresis.

There are situations in which it is desired to detect a very rare first allele in the presence of a very abundant second allele. This has been termed "sensitivity". In other words, the primer must not only be "specific" (go to the correct place in the genome), and be "selective" (reject wild type or other abundant sequences similar to the target sequence), but it must be highly selective, that is, "sensitive" enough to detect a very few mutant or other rare first sequence in the presence of an abundance of wild type or other abundant second sequence. See Makarov and Chupreta international patent application WO 2012/112 582 A2 at paragraph [0004].

To improve sensitivity while retaining specificity and selectivity, Vladimir Makarov and his colleagues at Swift Biosciences (Ann Arbor, Mich., U.S.A.) disclose a "discontinuous polynucleotide ["primer"] design" (WO 2012/112 582 A2 at paragraph [0051]) that has been commercialized as myT™ Primers. Such primers may be viewed as long conventional primers that are composed of two oligonucleotides so as to create an eight-nucleotide 3' priming sequence; and adding complementary tails to the 5' end of that sequence and to the 3' end of the other oligonucleotide to form a high-temperature stem. Through the stem, the two oligonucleotides are joined non-covalently and form a stable three-way junction when bound to the target sequence. The oligonucleotide with the eight-nucleotide 3' end is referred to as the "primer", and the other oligonucleotide is referred to as the "fixer". The function of the fixer is to provide specificity, that is, to bind the primer to the intended place in the genome. It is accordingly long, typically about 30-nucleotides in length. The function of the tails is to hybridize the two oligonucleotides under amplification conditions, so the tails also are fairly long, forming a stem 20-25 nucleotides in length. The function of the eight-nucleotide 3' region is to prime with selectivity. The discontinuous hybridization "in effect stabilized binding between the [priming] region of the primer oligonucleotide even if this region is as small as eight bases, thereby increasing the efficiency of PCR." (WO 2012/112582 A2). Further improvements are disclosed in Examples 9-11 of WO 2012/112582 A2. The nucleotide that is mismatched to the wild-type target is made the 3'-terminal nucleotide, as in ARMS; a third oligonucleotide, a blocking oligonucleotide ("blocker"), whose 5'-terminal nucleotide overlaps the 3'-terminal nucleotide of the primer and is complementary to the wild-type target, is included in the amplification reaction; and the 3'-terminal nucleotide of the primer is made of locked nucleic acid ("LNA"). For the detection of single-nucleotide polymorphisms in the K-ras and B-raf genes, detection sensitivity of one mutant in 14,000 wild-type (approximately 0.01%) was disclosed.

There remains a need for a single-oligonucleotide primer that has the ability to detect and, preferably, to quantify the number of a rare first target sequence, for example, a mutant target sequence, in the presence of a very large number of a second target sequence that differs from the first target sequence by as little as a single nucleotide, for example, a wild-type sequence.

SUMMARY OF INVENTION

This invention includes a multi-part primer for primer-dependent nucleic acid amplification methods, including particularly polymerase chain reaction (PCR) methods, that is capable of distinguishing between a rare intended target (e.g., a mutant DNA target) and a closely related sequence (e.g., a wild-type DNA target) that differs by a single-nucleotide substitution, sometimes referred to as a single-nucleotide polymorphism, for short, a SNP.

This invention includes primer-dependent nucleic acid amplification methods, for example PCR methods, that utilize a multi-part primer according to this invention and that are capable of selectively amplifying one or more rare target sequences in a population of abundant closely related sequences. Such intended target sequences may be rare mutant sequences, for example, sequences found in malignant cells, in an otherwise abundant wild-type population found in normal cells. For methods such as PCR methods that utilize a DNA-dependent DNA polymerase, the intended target and related sequences are DNA sequences that occur in a sample, or they are cDNA sequences that are made by reverse transcription from RNA sequences, including mRNA sequences, that occur in a sample. Reverse transcription may be performed in the same reaction mixture as subsequent amplification, or it may be performed separately before amplification. Multi-part primers can be used as primers in reverse transcription reactions. This invention also includes amplification and detection methods that include detection of amplified products, or "amplicons". The description that follows, including the Example, describes multi-part primers in connection with PCR amplification reactions starting with DNA targets. Persons skilled in the art will understand how to apply these teachings to multi-part primers in connection with other primer-dependent nucleic acid amplification methods.

This invention further includes reagent kits containing reagents for performing such amplification methods, including such amplification and detection methods.

This invention addresses, inter alia, a major goal of molecular diagnostics, which is to find a sensitive and specific means for detecting extremely rare cancer cells (by virtue of an identifying somatic mutation) in a clinical sample containing very abundant normal cells, and to be able to quantitatively determine their abundance There are multiple advantages of being able to do this, including:

1. The ability to detect the presence and abundance of cancer cells after treatment (such as after a bone marrow transplant in leukemia patients). Utilizing this invention will enable physicians to determine whether the administration of (rather toxic) drugs can be discontinued. This invention will enable clinical studies to be carried out to determine the level of minimum residual disease that can be handled by the body without drug treatment. Moreover, patients can be monitored over time after treatment to detect the appearance of higher levels that can then be treated by appropriate means.

2. The ability to rapidly detect and quantitate rare cancer cells in biopsies taken during surgery (at levels too low to be seen in a microscope by a pathologist). Utilizing this invention will enable surgeons to rationally decide the extent of surgery, sparing the removal of unaffected tissues.

3. The ability to detect key mutations in DNA molecules released into blood plasma by the natural process of destruction of rare circulating tumor cells in blood. Utilizing this invention will enable the early detection of tumors whose cells have acquired the ability to metastasize, providing physicians an opportunity for early intervention.

4. The ability to monitor patients whose genetic inheritance suggests that life-threatening tumors can arise during their lifetime (such as in many breast cancers). Utilizing this invention will enable periodic monitoring to determine if key somatic mutations have occurred, so that therapeutic intervention can be provided at a very early stage in the disease.

Other applications for this invention will occur to persons skilled in the art.

By "rare" and "abundant" is meant that the ratio of intended target sequences to closely related sequences is at least in the range of $1/10^3$ to $1/10^7$ (that is, one in a thousand, one in ten thousand, one in one-hundred thousand, one in a million, or one in ten million). By "closely related" is meant a sequence that differs from an intended target sequence by one, two, or at most a few nucleotides. Mutant target sequences that differ from wild-type sequences at a particular location by a single nucleotide are commonly referred to as being or having a single-nucleotide polymorphism (SNP).

Methods according to this invention include primer-dependent nucleic acid amplification for at least one intended target sequence (e.g., a mutant DNA target sequence), which may occur rarely in a sample or reaction mixture containing an abundance of the closely related, unintended target sequence (e.g., a wild-type DNA target sequence). These methods utilize a reaction mixture that contains for each rare target a multi-part primer according to this invention. Three parts of the primer cooperate with one another to yield an amplification that is extremely selective. FIG. 1 is a schematic representation of a primer according to this invention. FIG. 1 includes two schematics: the top schematic shows a multi-part primer 103 under hybridization conditions, such as occurs during the annealing step of a PCR cycle, in relation to its intended target 101, which may be rare; and the bottom schematic shows the same primer in relation to a closely related sequence, herein referred to as an unintended or mismatched target 102. Intended target 101 and unintended target 102 have the same nucleotide sequence, except that intended target 101 has one or more nucleotides "x", preferably a single nucleotide, that differ from the corresponding nucleotide or nucleotides in mismatched target 102, here designated "y". For example, unintended target sequence 102 may be a wild-type human DNA sequence, and intended target sequence 101 may be a mutant cancer cell sequence containing a SNP. The upper schematic depicts a primer 103 that is hybridized to intended target strand 101. In the 5'-to-3' direction, the primer includes anchor sequence 104, bridge sequence 105, and foot sequence 106. Primer 103 optionally may include a 5' tail 107 to impart added functionality. It also optionally includes a blocking group 108. During primer annealing at the start of amplification, anchor sequence 104 hybridizes to intended target 101, as conventionally indicated by the short vertical lines between the anchor sequence and its binding site (representing the pairing of complementary nucleotides). Bridge sequence 105 is mismatched (not complementary) to target 101 at sequence 109, which we refer to as the "intervening sequence," and causes a "bubble" in the duplex structure. Foot sequence 106 hybridizes to intended target 101 and primes copying by a DNA polymerase. The lower schematic depicts the same primer 103 that is hybridized to unintended, mismatched target 102. As stated, mismatched target 102 differs from intended target 101 by at least one nucleotide change (x to y) in the sequence opposite primer foot 106. During primer annealing at the start of amplification, anchor sequence 104 hybridizes to unintended target 102 at the anchor-sequence binding site, as shown. Again, bridge sequence 105 is mismatched to intervening sequence 109. However, foot sequence 106 is not hybridized to target 102, and target 102 is not primed for copying.

In an ideal amplification reaction according to FIG. 1, intended target 101, even if rare, would always be copied, and unintended target 102, even if abundant, would never be copied. However, priming is a statistical matter. For example, primers go on and off targets, perfect and mismatched, with some frequency. Consequently, perfect targets are not always copied, and mismatched targets are sometimes copied. Selectively amplifying and detecting rare targets thus depends both on the frequency at which perfect targets are copied and on the frequency at which mismatched targets are copied. Multi-part primers useful in this invention have three contiguous sequences (anchor sequence, bridge sequence and foot sequence) that cooperate with one another to achieve very high selectivity in practical amplification reactions, including amplification-and-detection assays. The anchor sequence serves to hybridize the primer to the target sequence, which is the same (or almost the same) in the intended target and the unintended, mismatched target, in an efficient manner not dissimilar to hybridization of a conventional primer. The bridge and foot sequences, more fully described below, cooperate to impart primer specificity, that is, selectivity for the intended target over the mismatched target. We have discovered that a high degree of selectivity is achieved if the bridge and foot sequences cooperate to make copying of the intended target unlikely rather than likely. Further, we make the bridge sequence rabidly and efficiently copyable. The bridge sequence is preferably a DNA sequence. The result achieved is amplification of the intended target sequence that is delayed in starting, but that proceeds normally once it has begun; but amplification of the unintended, mismatched target sequence that is significantly more delayed but that proceeds normally once it has begun. The increased delay for the mismatched target relative to the matched target is an improvement in selectivity achieved by the primer. Such improved selectivity is achieved, because the probability of the unintended target sequence being copied by a DNA polymerase is at least 1,000 times less than the probability of the intended target sequence being copied, preferably at least 10,000 times less and more preferably at least 100,000 times less.

Referring to FIG. 1, the primer includes an anchor sequence 104 that hybridizes the primer to a binding site in the intended target and the closely related target sequence during the primer-annealing step, which includes a primer-annealing temperature, of the amplification reaction. In that regard, the anchor sequence is like, and functions like, a conventional primer. It may be perfectly complementary to the target and to the closely related sequence, or it may contain one or more mismatched nucleotides. In the amplification reaction in which it is used, it generally has a melting temperature, Tm, at least equal to or above the annealing temperature, so as to enhance hybridization. In most of the Examples the anchor sequence Tm is between 3° C. and 10° C. above the primer-annealing temperature. To the extent not prevented by a blocking group, all or a portion of anchor sequences of multi-part primers used in this invention are copied by DNA polymerase. Because exponential amplification proceeds rapidly with high, normal PCR efficiency, the inclusion of non-natural nucleotides, nucleotide mimics, and non-natural internucleotide linkages in copied portions is limited to types and numbers that permit rapid and efficient copying by DNA polymerase. We prefer that anchor sequences be DNA sequences.

Anchor sequence 104 typically forms a probe-target hybrid 15-40 nucleotides in length, preferably 15-30 nucleotides in length, and more preferably 20-30 nucleotides in length. Shorter anchor sequences must still hybridize to their target sequences during primer annealing, as stated above, which often means that their Tm's must be at least 50° C. (e.g., 66-72° C.). It may be perfectly complementary to the target, or it may contain one or more mismatches; for example, where one is investigating a target whose sequence versus the anchor is variable, one may choose an anchor sequence 104 that is a consensus sequence that is not perfectly complementary to any version of the target but that hybridizes to all variants during primer annealing. We prefer DNA anchor sequences that form anchor-sequence/target hybrids generally in the range of 15-30 base pairs, as is typical for conventional PCR primers. We demonstrate in the Examples below anchor sequences that are 24-nucleotides long, that are DNA, and that are fully complementary to the target sequence. The multi-part primer does not prime sequences in the reaction mixture other than its target sequence, that is, the intended target sequence and the unintended, mismatched target sequence. Whereas a conventional primer must be designed to achieve that function, the requirement for an anchor sequence is less strict, because the foot sequence aids in discriminating against other sequences that are or may be present in a sample.

Referring to FIG. 1, the primer includes a foot sequence 106 that is complementary to the intended target sequence in the region that includes the nucleotide (the SNP nucleotide), or in some cases two nucleotides, that are different from the unintended, mismatched target sequence. The foot sequence may be perfectly complementary to the intended target sequence, or it may contain one or, in some cases, even two nucleotides that are mismatched to both the intended target sequence and the unintended target sequence. Foot sequence 106 is always more complementary to the intended target sequence than to the mismatched target sequence by at least one nucleotide. The foot sequence is copied during amplification. Because exponential amplification proceeds rapidly with high, normal PCR efficiency, the inclusion of non-natural nucleotides, nucleotide mimics, and non-natural internucleotide linkages is limited to types and numbers that permit rapid and efficient copying by DNA polymerase. We prefer that foot sequences be DNA sequences. Because it is desirable that subsequent exponential amplification of amplicons proceed with high, normal PCR efficiency, the inclusion in the foot sequence of non-natural nucleotides, nucleotide mimics, and non-natural internucleotide linkages is limited to types and numbers that permit efficient copying by DNA polymerase. In preferred embodiments the foot sequence is a DNA sequence that is perfectly complementary to the intended target sequence and contains a single nucleotide that is mismatched to a nucleotide in the unintended target sequence.

Foot sequence 106 forms a hybrid with the intended target sequence that is at least 5 nucleotides long, for example, in the range of 5-8 base pairs, preferably in the range of 6-8 base pairs, and more preferably not longer than 7 nucleotides long, for example, in the range of 6-7 base pairs. When the anchor sequence is hybridized to the intended target sequence, there is only one binding site for the foot sequence. As the foot sequence is shortened, the chance is increased that it could have another possible binding site, particularly if the foot sequence is shortened to just 5 nucleotides, a matter to be taken into account in primer design. While, as we demonstrate in the Examples, the mismatched nucleotide versus the unintended target may occur at any nucleotide position of foot 106, we prefer that the mismatched nucleotide either be the 3' terminal nucleotide, as in an ARMS primer (Newton et al. (1989) Nucleic Acids Res. 17:2503-2516; and Ferrie et al. (1992) Am. J. Hum. Genet. 51:251-262) or reside one nucleotide in from the 3' end of the foot, which we sometimes refer to as the "3' penultimate nucleotide."

Again referring to FIG. 1, the primer includes a bridge sequence 105 that is chosen so that it cannot hybridize with the intervening sequence 109 during the annealing of the multi-part primer to a target molecule. The bridge sequence or, if it contains a blocking group, the 3' portion thereof, is copied by DNA polymerase. Because it is desired that exponential amplification of the amplicons proceed rapidly with high, normal PCR efficiency, the inclusion in the bridge sequence's copied portion of non-natural nucleotides, nucleotide mimics, and non-natural internucleotide linkages is limited to types and numbers that permit rapid and efficient copying by DNA polymerase. Bridge sequences that are DNA are preferred.

The bridge sequence 105 and its opposed intervening sequence 109 in the target form a bubble in the primer/intended target hybrid. The circumference of the bubble is the length of bridge sequence 105 plus the length of intervening sequence 109, plus 4 (a pair of nucleotides from the anchor-sequence hybrid and a pair of nucleotides from the foot-sequence hybrid). The bridge and intervening sequence need not be of equal length: either can be shorter than the other. In certain embodiments the length of the intervening sequence can be zero. In preferred embodiments it is at least six nucleotides long. In more preferred embodiments wherein the sum of the lengths of the bridge and intervening sequences is at least 24 nucleotides, we prefer that the intervening sequence have a length of at least eight nucleotides, more preferably at least ten nucleotides. The bridge sequence should be at least six nucleotides long. Certain preferred embodiments have bridge and intervening sequences that are equal in length. The circumference of the bubble may be as short as 16 nucleotides and as long as 52 nucleotides, for example 16-52 nucleotides, 20-52 nucleotides, or 28-44 nucleotides.

As general considerations for design of multi-part primers, increasing the circumference of the bubble and shortening the foot increases the delay in amplification of the intended target. The number of PCR cycles needed to synthesize a predetermined detectable number of amplicons in a reaction initiated with a particular number of intended target sequences (the threshold cycle, $C_T$, for that reaction) can be measured, for instance, by observing the fluorescence intensity of the intercalating dye SYBR® Green, whose intensity reflects the number of amplicons present during each PCR cycle. This provides a method for measuring the difference in probability that a DNA polymerase extends multi-part primer/unintended-target hybrids relative to the probability that the DNA polymerase extends multi-part primer/intended target hybrids. Given that amplification proceeds by exponential doubling, a $C_T$ difference of 10 cycles indicates that the probability of extension of a multi-part primer/unintended-target hybrid is 1,000 times lower than the probability of extension of the multi-part primer/intended-target hybrid; a $C_T$ difference of 13.3 cycles indicates that the probability is 10,000 times lower; a $C_T$ difference of about 16.6 cycles indicates that the probability is 100,000 times lower; and a $C_T$ difference of 20 cycles indicates that the probability is one-million times lower.

In an assay according to this invention utilizing multi-part primers, the difference between the higher threshold cycle observed for mismatched target sequences and the lower threshold cycle observed for the same number, for example $10^6$ copies, of intended target sequences, as reflected in the $\Delta C_T$ from measurements of fluorescence intensity at each PCR cycle achieved by adding SYBR® Green dye to the reaction mixture, should be at least 10 cycles, preferably at least 12 cycles, more preferably at least 14 cycles, even more preferably at least 17 cycles, even more preferably at least 18 cycles, and most preferably 20 cycles or more. In amplification reactions wherein a multi-part primer according to this invention replaces a well-designed conventional PCR primer, there is a delay ($\Delta C_T$) in the threshold cycle achieved using the intended target sequence. The amount of delay depends on how well the compared conventional primer is designed, but typically, comparing to a conventional primer consisting of just the anchor sequence of the multi-part primer, the delay is at least two amplification cycles, often at least three cycles, and sometimes at least eight cycles, or even ten cycles.

Preferred embodiments of methods according to this invention include detecting product resulting from amplification of the rare target sequence. Detection of amplified product may be performed separately following amplification, for example, by gel electrophoresis. In preferred embodiments, detection reagents are included in the amplification reaction mixture, in which case detection may be "real time," that is, performed on multiple occasions during the course of amplification, or "end point," that is, performed after conclusion of the amplification reaction, preferably by homogeneous detection without opening the reaction container. Detection reagents include DNA binding dyes, for example SYBR® Green, dual-labeled fluorescent probes that signal production of amplified product, for example, molecular beacon probes, and a combination of a binding dye and a fluorescent probe that is stimulated by emission from the dye. In addition, as described herein, the primers themselves can include fluorescent labels that only fluoresce when the primer is incorporated into an amplicon, or alternatively, when the primer binds to a complementary amplicon.

This invention includes reaction mixtures for amplifying at least one target sequence. Reaction mixtures include a pair of primers for each intended target sequence, one primer in each pair being a multi-part primer as described herein. Reaction mixtures also include reagents for amplifying the targets, including deoxyribonucleoside triphosphates, amplification buffer, and DNA polymerase. Preferred reaction mixtures for assay methods according to this invention also include detection reagents, that is, DNA binding dye, hybridization probes (or both), or a 5' functional tail of each multi-part primer. If the starting samples contain RNA, the amplification reaction mixtures may also include reverse transcriptase and primers for reverse transcription.

This invention also includes products that are kits for performing the amplification reactions and amplification-and-detection reactions described above for one or more intended target sequences. A kit includes oligonucleotides and reagents needed to create a reaction mixture according to this invention. A kit for starting samples that are RNA may include reagents for reverse transcription.

The details of one or more embodiments of the invention are set forth in the description below. Other features, objectives, and advantages of the invention will be apparent from the description and from the claims.

DETAILED DESCRIPTION

Figure 1:
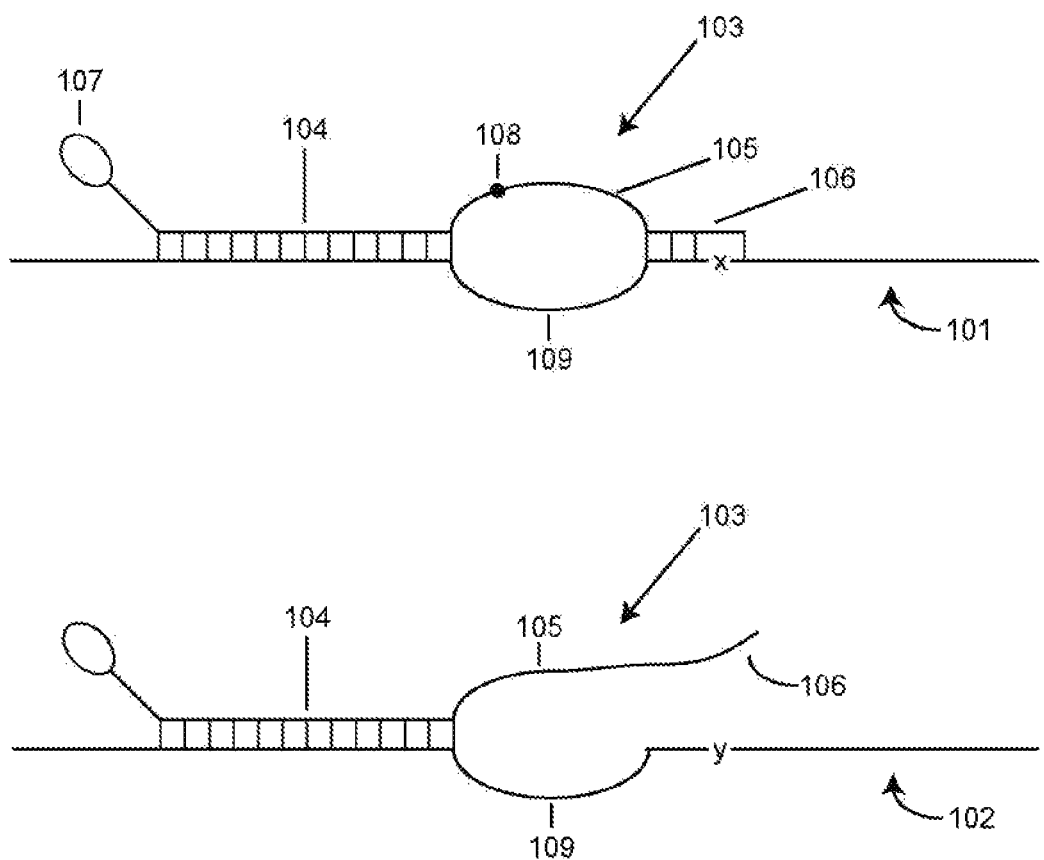
FIG. 1 is a schematic representation of a multi-part primer useful in this invention hybridized to its intended target sequence and hybridized to a mismatched sequence differing from the intended target sequence by one or more nucleotide substitutions.

This invention is based, at least in part, on a unique design of multi-part primers for primer-dependent amplification reactions. Accordingly, this invention discloses the design and characteristics of multi-part primers, which exhibit extraordinary selectivity when they are hybridized to the templates that are present in the original sample. Due to this extraordinary selectivity, we call the multi-part primers of this invention "SuperSelective" primers.

Significantly, once synthesis is initiated on mutant templates, the resulting amplicons are exponentially amplified with high efficiency, and the real-time data provide a conventional means of assessing the abundance of the mutant templates present in the original sample. The experiments described below demonstrate that SuperSelective primers are sufficiently discriminatory to suppress the synthesis of wild-type sequences to such an extent that as few as 10 molecules of a mutant sequence can be reliably detected in a sample containing 1,000,000 molecules of the wild-type sequence, even when the only difference between the mutant and the wild-type is a single-nucleotide polymorphism.

1. Primer-Dependent Amplification Reactions

Primer-dependent amplification reactions useful in methods of this invention may be any suitable exponential amplification method, including the polymerase chain reaction (PCR), either symmetric or non-symmetric, the ligase chain reaction (LCR), the nicking enzyme amplification reaction (NEAR), strand-displacement amplification (SDA), nucleic acid sequence-based amplification (NASBA), transcription-mediated amplification (TMA), and rolling circle amplification (RCA). Preferred methods utilize PCR. In non-symmetric PCR amplification methods, for example asymmetric PCR, one primer, the limiting primer, is present in a limiting amount so as to be exhausted prior to completion of amplification, after which linear amplification occurs, using the remaining primer, the excess primer. A non-symmetric PCR method useful in this invention is LATE-PCR (see, for example, European Patent EP 1,468,114; and Pierce et al. (2005) Proc. Natl. Acad. Sci. USA 102:8609-8614). If a non-symmetric amplification method is used, the multi-part primer is preferably the excess primer. Preferred methods also include digital PCR (see, for example, Vogelstein and Kinzler (1999) Proc. Natl. Acad. Sci. USA 98:9236-9241), where it is desirable to detect a large number of amplicons from a single mutant template molecule that is present in reactions that contain abundant wild-type molecules.

If the amplification reaction utilizes an RNA-dependent DNA polymerase (an example being NASBA), the amplification reaction is isothermal. We refer to repeated rounds of synthesis of amplified product as "cycles", but they are not thermal cycles. For such amplification the "intended target sequence" and the "unintended target sequence" that are primed by a multi-part primer according to this invention are RNA sequences that occur in an original sample and in the amplification reaction mixture, where they are present with the DNA polymerase and the multi-part primer.

If the amplification reaction utilizes a DNA-dependent DNA polymerase (an example being PCR), an original sample may contain either DNA or RNA targets. For such amplifications, the "intended target sequence" and the "unintended target sequence" that are primed by a multi-part primer according to this invention are DNA sequences that either occur in an original sample or are made by reverse transcribing RNA sequences that occur in the original sample. If the multi-part primer is used for reverse transcription, the "intended target sequence" and the "unintended target sequence" are RNA as well as cDNA. If a separate, outside primer is used for reverse transcription, the "intended target sequence" and the "unintended target sequence" are cDNA. In either case, the "intended target sequence" and the "unintended target sequence" are nucleic acid sequences that are present in the amplification reaction mixture with the DNA polymerase and the multi-part primer. Primer-dependent amplification reactions comprise repeated thermal cycles of primer annealing, primer extension, and strand denaturation (strand melting). Primer annealing may be performed at a temperature below the primer-extension temperature (for example, three-temperature PCR), or primer annealing and primer extension may be performed at the same temperature (for example, two-temperature PCR). The overall thermal profile of the reaction may include repetitions of a particular cycle, or temperatures/times may be varied during one or more cycles. For example, once amplification has begun and the priming sequence of a multi-part primer is lengthened, a higher annealing temperature appropriate for the longer primer might be used to complete the amplification reaction.

Assay methods according to this invention include detection of an amplified target sequence. Methods according to this invention are not limited to particular detection schemes. Detection may be performed following amplification, as by gel electrophoresis. Alternately, homogeneous detection may be performed in a single tube, well, or other reaction vessel during (real time) or at the conclusion (end point) of the amplification reaction using reagents present during amplification. Alternatively, using a microfluidic device, amplified products can be moved to a chamber in which they contact one or more detection reagents or isolating reagents, such as immobilized capture probes. Detection reagents include double-stranded DNA binding dyes, for example SYBR Green, and fluorescently or luminescently labeled hybridization probes that signal upon hybridization, for example molecular beacon probes or ResonSense® probes, or probes that are cleaved during amplification, for example 5'-nuclease (TaqMan®) probes.

2. Multi-Part Primer

Figure 2:
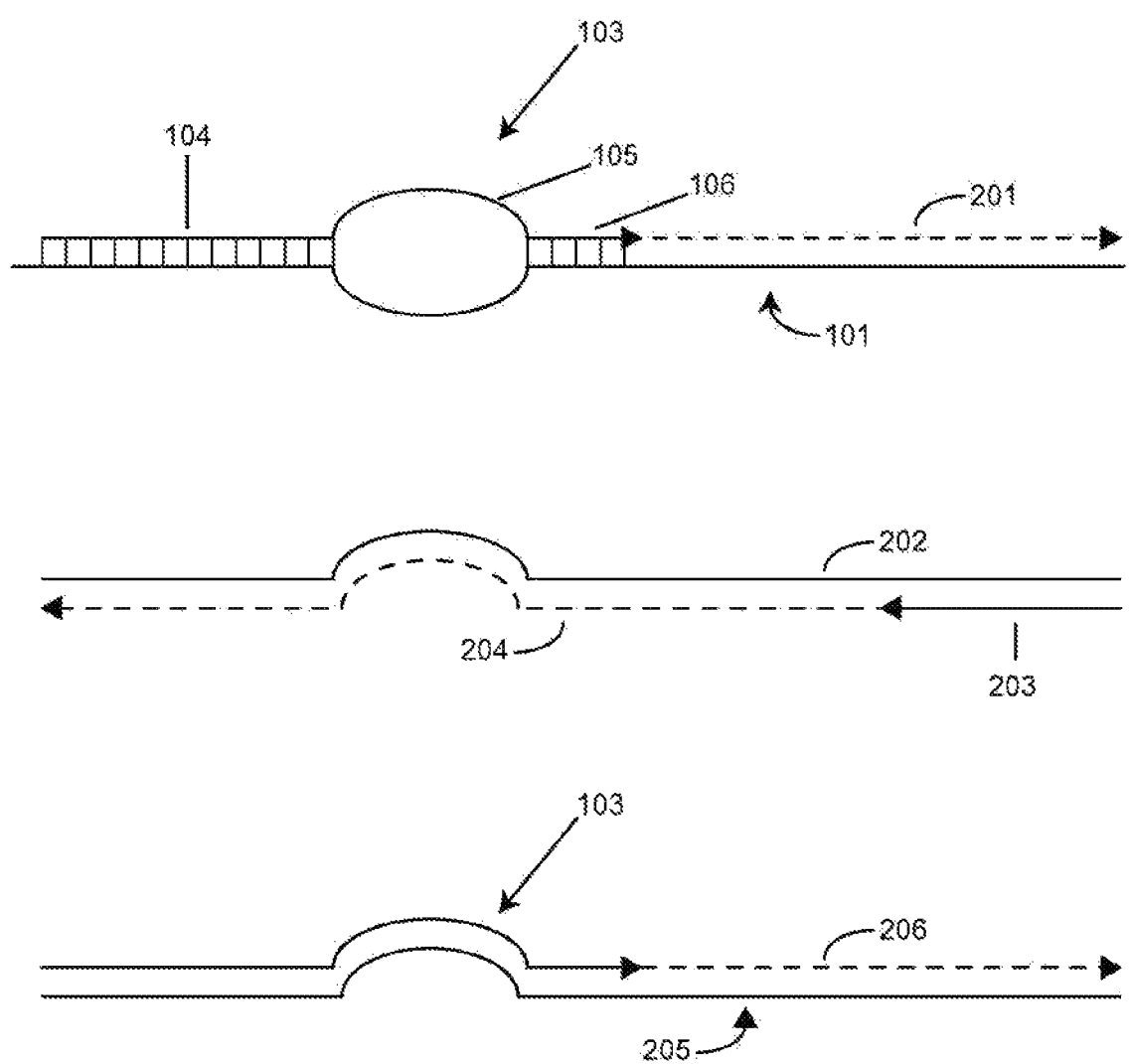
FIG. 2 is a schematic representation of the amplification cycle in which a multi-part primer of this invention is first copied, as well as subsequent copying of the resulting amplicon in the next two cycles.

As discussed above, methods of this invention include use of a multi-part primer for each rare target sequence. Amplification with a multi-part primer is illustrated in FIG. 2 for primer 103 and intended target sequence 101 (FIG. 1). First, primer 103, shown as a forward primer, anneals to target sequence 101 and is extended by a DNA polymerase using strand 101 as a template to produce extension product 201. Referring to the middle sketch, in the next amplification cycle strand 202, which comprises primer 103 and extension product 201, becomes a template for the reverse primer, a conventional primer 203. Reverse primer 203 anneals and is extended by the DNA polymerase using strand 202 as a template to produce extension product 204. It will be observed that extension product 204 includes a sequence perfectly complementary to primer 103. Extension product 204 includes such a perfectly complementary sequence irrespective of the sequence of strand 101. That is, if primer 103 has been extended in the earlier cycle (top sketch), the resulting strand 202 (middle sketch) always includes the perfect complement of primer 103. In the next amplification cycle (lower sketch), strand 205, which comprises reverse primer 203 and extension product 204, contains the perfect complement of primer 103; and primer 103 binds to strand 205 and is extended by a DNA polymerase to produce extension product 206. Thus, FIG. 2 applies to mismatched target sequence 102, as well as to intended target sequence 101, any time that the multi-part primer anneals and is extended to generate amplicon 202.

Figure 3:
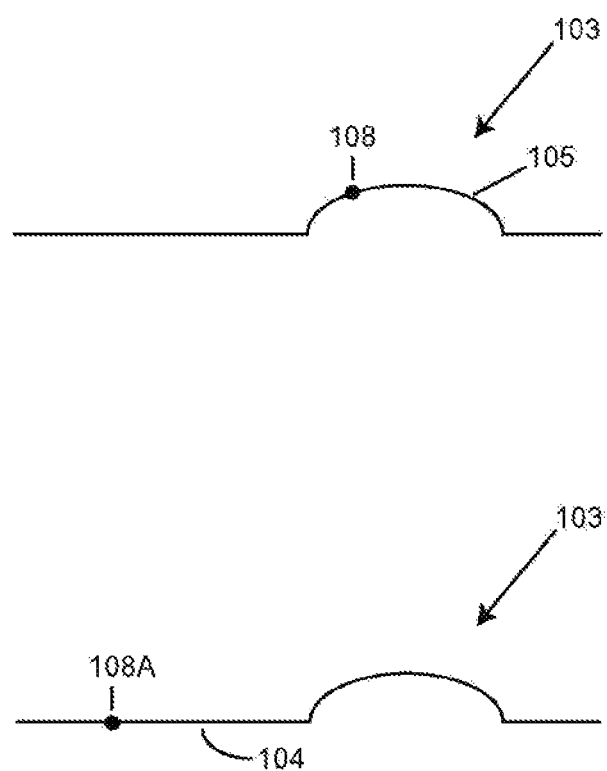
FIG. 3 is a schematic representation of a multi-part primer according to this invention showing locations for placement of a blocking group that terminates copying by a DNA polymerase.

As indicated in the preceding paragraph, FIG. 2 shows copying of the entirety of primer 103 during extension of reverse primer 203. That creates a long priming region for the next cycle, namely, a sequence complementary to anchor sequence 104, bridge sequence 105 and foot sequence 106. In certain embodiments it may not be desired to proceed with the remainder of amplification with a priming region of such length. FIG. 3 illustrates the use of multi-part primers that possess a blocking group to shorten the priming region in later cycles. Blocking groups are well known for stopping extension by a DNA polymerase. A blocking group may be, for example, hexethylene glycol (HEG). Particularly if bridge sequence 105 is long, it may be desirable to place a blocking group 108 in bridge sequence 105, as shown in the top sketch of FIG. 3. The priming region in later amplification cycles will consist of the nucleotides of foot 106 plus nucleotides of bridge 105 that are located 3' of blocking group 108. Alternatively, it may be desirable to place a blocking group 108A in anchor sequence 104, as shown in the bottom sketch of FIG. 3. In such an embodiment, the priming region in later cycles of amplification will include the nucleotides of foot 106, the nucleotides of bridge 105, plus nucleotides of anchor 104 that are located 3' of blocking group 108A.

Figure 4:
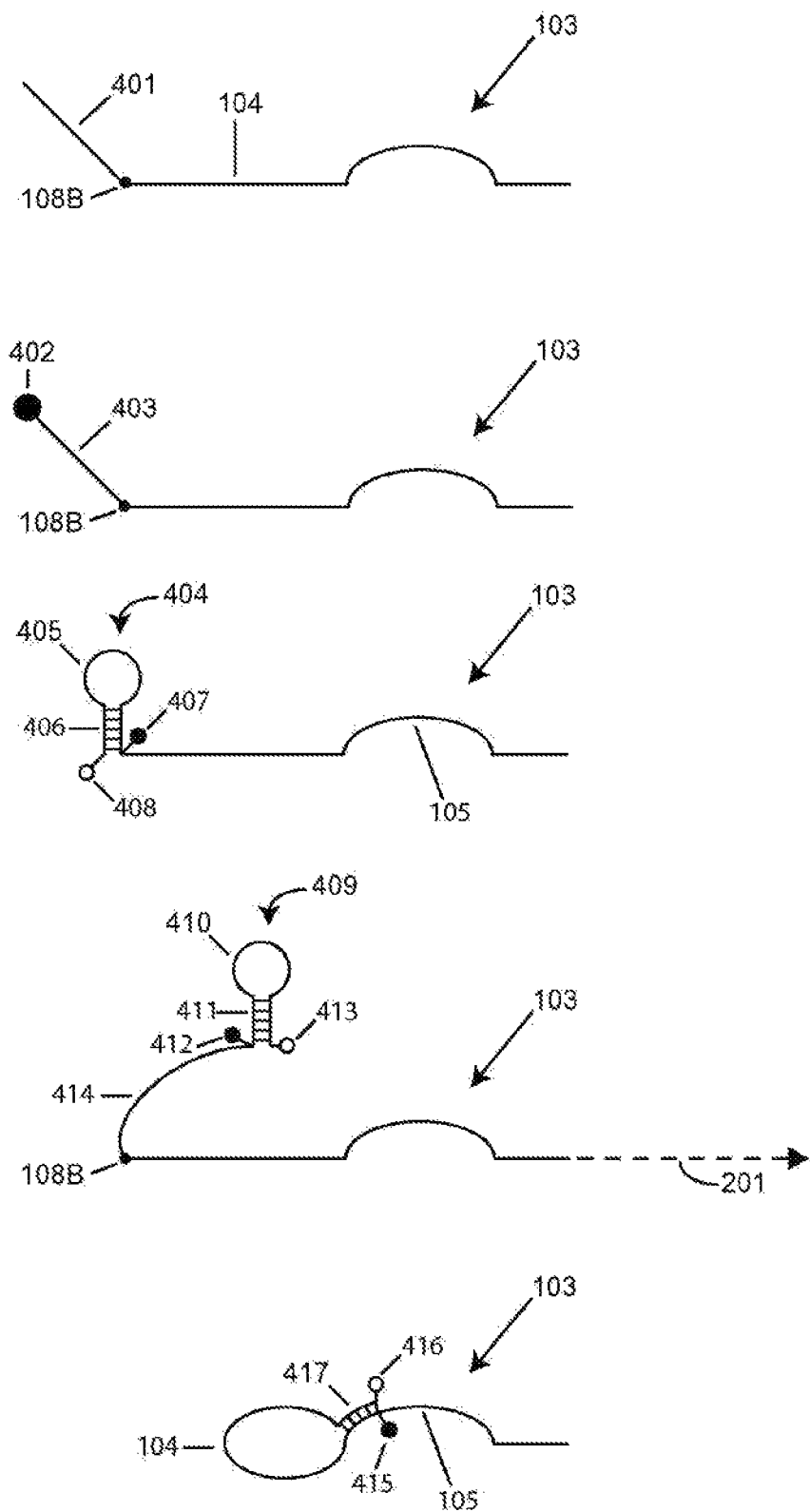
FIG. 4 is a schematic representation of several exemplary optional 5' functional moieties.

As stated above, a multi-part primer for use in this invention may include a functional moiety, a 5' tail attached to anchor sequence 104. This invention is not limited as to the function such a group may perform or as to the structure thereof. Examples of several functional moieties are illustrated in FIG. 4. Each drawing shows a multi-part primer 103 with anchor sequence 104 and a different functional group located at the 5' end of the anchor sequence. Functional group 401 is simply an oligonucleotide tail that can be used for hybridization to a capture probe or hybridization to a labeled probe. Tail 401, as depicted, is not complementary to another sequence within primer 103. Because of the presence of blocking group 108B in the primer containing Tail 401, DNA polymerase does not copy Tail 401, and Tail 401 is always single stranded and available to bind to a capture probe or to a labeled probe, irrespective of whether the complementary amplicons are single stranded or double stranded. Oligonucleotide 401 may serve as a "zip code" for the immobilization of the resulting amplicons to a specific position on an array of capture probes, or to capture probes linked to different elements of a distributed array. Another functional moiety includes biotin group 402 attached to anchor sequence 104 through linker 403. Because of the presence of blocking group 108B in the primer, DNA polymerase does not copy linker 403, and linker 403 is always single stranded. Biotin group 402 enables the amplicons synthesized from the primer to acquire an additional function. For example, a biotin group allows amplicons to be strongly captured by streptavidin proteins that are immobilized through a linking group to a solid surface, such as a paramagnetic bead. Another functional moiety is hairpin oligonucleotide 404 having a stem-and-loop structure comprising single-stranded loop 405 and double-stranded stem 406 that is labeled with quencher 407 (preferably a non-fluorescent quencher such as Dabcyl or Black Hole Quencher 2) and an interacting fluorescent moiety 408 (preferably a fluorophore). Extension of reverse primer 203 (FIG. 2) would continue through labeled hairpin 404, separating quencher 407 from fluorescent moiety 408, thereby generating a fluorescent signal. See Nazarenko et al. (1997) Nucleic Acids Res. 25:2516-2521. Inclusion of labeled hairpin 404 in primer 103 leads to a fluorescent signal indicative of amplification. Yet another functional moiety is a molecular beacon probe 409 attached to anchor sequence 104 through oligonucleotide sequence 414 and blocking group 108B. This functional moiety has the additional function of a Scorpion® primer, that is, enabling the tethered molecular probe to hybridize to the target strand (both the intended target sequence and the mismatched target sequence) downstream from primer 103 as copy 201 is generated. Molecular beacon probe 409 comprises loop 410 and stem 411 covalently attached to which are interacting quencher 412 and fluorescent moiety 413, such that hybridization of probe 409 to extension product 201 disrupts stem 411 and generates a fluorescent signal indicative of amplification. Unlike hairpin 404, hairpin 409 is not copied, because in this case primer 103 contains blocking group 108B. The drawing at the bottom of FIG. 4 depicts a variant of hairpin 404 in which the 5'-terminal sequence of the stem 417 of the molecular beacon is complementary to a portion of bridge sequence 105 and the loop comprises anchor sequence 104. Consequently, upon hybridization to a complementary amplicon strand, the rigidity of the resulting hybrid separates interacting quencher 415 from fluorescent moiety 416, thereby generating a fluorescent signal indicative of amplification.

The multi-part primer does not prime sequences in the reaction mixture other than its target sequence, that is, the intended target sequence and the unintended, mismatched target sequence. The 3' portion of the bridge sequence plus the foot sequence do not together form a sequence that serves as a primer for such irrelevant sequences.

A multi-part primer useful in methods of this invention functions as follows, with reference to FIG. 1. In the first round of synthesis, for example, in the first PCR cycle, which may follow a high-temperature denaturation step, anchor sequence 104 hybridizes to the target sequence, both the intended target 101 and the unintended, mismatched target 102. Bridge sequence 105 does not hybridize to the target sequence. Foot sequence 106 hybridizes preferentially to intended target sequence 101, but to some extent it hybridizes also to unintended, mismatched target sequence 102. The hybrids form and separate with some frequency. Also with some frequency, a DNA polymerase binds to the formed hybrids and initiates extension of the primer. With respect to intended target sequence 101, the combined frequencies of hybrid formation and polymerase binding/extension result in inefficient copying of intended target sequence 101, which we measure as a delay in the PCR threshold cycle, $C_T$, of at least two cycles when comparison is made between a PCR amplification and detection assay with SYBR Green detection using the multi-part primer and $10^6$ copies of intended target sequence 101 (with or without copies of unintended target sequence 102) and the same assay using a corresponding conventional primer (which is similar to the anchor sequence in multi-part primers). With respect to unintended, mismatched target sequence 102, the combined frequencies of hybrid formation and polymerase binding/extension result in extremely inefficient copying, which we measure as a difference ($\Delta C_T$) in such an assay between the $C_T$ with the multi-part primer and $10^6$ copies of mismatched target sequence 102 and the $C_T$ with the multi-part primer and $10^6$ copies of intended target sequence 101 (with or without copies of unintended target sequence 102). The delay for the intended target sequence caused by the multi-part primer is at least two PCR cycles, and may be larger, for example, four cycles or even 5-10 cycles. The difference ($\Delta C_T$) between the unintended, mismatched target and the intended target is at least ten PCR cycles, preferably more. The intended target sequence will be copied as amplification proceeds through additional cycles, and, eventually, so will the mismatched target. Synthesized copies from both targets will contain the multi-part primer and so will be identical.

After a multi-part primer initiates the synthesis of an amplicon on a target nucleic acid molecule that was present in the sample to be tested prior to amplification, whether that initiation occurs in the first cycle or in a later cycle, the resulting amplicon is then exponentially amplified in subsequent cycles rapidly with normal, high efficiency, with the multi-part primer acting as a conventional primer with respect to the amplicons. For example, for the copying of amplicons, the multi-part primer functions in the same manner as a conventional PCR primer that is 20-50 nucleotides long. This means that more than the foot acts as a primer once amplification has begun. One possibility is that the entirety (or at least the entirety except for a functional moiety located 5' to a blocking group, such as 401, 403, and 409) is copied and acts as a primer for the copying of amplicons.

In those embodiments that possess a blocking group in the multi-part primer, the purpose of the blocking group is to prevent copying of some portion of the primer's 5' end. Blocking groups are familiar to persons skilled in the art. A blocking group may be, for example, hexethylene glycol or an abasic nucleotide that lacks a nitrogenous base. A blocking group may be placed to the 5' end of anchor sequence 104 to prevent copying of a functional moiety, such as the placement of blocking group 108B with respect to functional moieties 401, 403, or 409; or it may be placed at any location within anchor sequence 104, such as the placement of blocking group 108A; or it may be placed within bridge sequence 105, such as the placement of blocking group 108; just so long as the shortened sequence that is copied is sufficiently long to act as an efficient primer when the template molecules are amplicons. To illustrate, suppose that a multi-part primer has a foot sequence six nucleotides long and that one wishes that 35 nucleotides be copied. If bridge sequence 105 is twenty-four nucleotides long, five nucleotides of the anchor sequence 104 must be downstream (that is, 3') of a blocking group to achieve the desired primer length.

3. Nomenclatures

In the Examples disclosed below, two nomenclatures are used to refer to a number of multi-part primers of this invention.

In one nomenclature, a multi-part primer is referred to in such a format as, e.g., a "24-14-5:1:1" primer, referring to an anchor sequence that is 24 nucleotides long, a bridge sequence that is 14 nucleotides long, and a foot sequence that is seven nucleotides long (comprising, from the 5' end of the foot, five nucleotides complementary to both the mutant (MUT) and wild type (WT) targets, one interrogating nucleotide that is not complementary to the corresponding nucleotide in the WT target, but that is complementary to the corresponding nucleotide in the MUT target, and, finally, one nucleotide complementary to both targets. Because the interrogating nucleotide is located one nucleotide inboard of the 3' end of the primer, we refer to this nucleotide as being located at the "3'-penultimate position."

Comparing the bridge sequence to the region of the target sequence lying between the binding sequence of the anchor and the binding sequence of the foot, which we call the "intervening sequence," one can see that the intervening sequence in some of the Examples below is fourteen nucleotides long, the same length as the bridge sequence while in others (such as Example 8) the intervening sequence and the bridge sequence have different lengths. To specify the length of the intervening sequence, a second nomenclature is sometimes used. In that case, a "24-18/10-5:1:1" multi-part primer indicates that its 5'-anchor sequence is 24-nucleotides long, its bridge sequence is 18-nucleotides long and occurs opposite an intervening sequence in the template that is 10-nucleotides long, and its 3'-foot sequence is 7-nucleotides long and consists of a 5' segment that is fully complementary to both the mutant and to the wild-type templates, followed by an interrogating nucleotide that is only complementary to the corresponding nucleotide in the mutant template, followed by a 3' nucleotide that is complementary to the corresponding nucleotide in both the mutant and the wild-type templates.

The sequence of the bridge sequence is chosen so that it is not complementary to the intervening sequence, in order to prevent the hybridization of the bridge sequence to the intervening sequence during primer annealing. Instead of annealing to each other, the bridge sequence and the intervening sequence form a single-stranded "bubble" when both the anchor sequence and the foot sequence are hybridized to the template. We sometimes refer to the combination of a bridge sequence and an intervening sequence as a bubble. For example, the designation 24-14/14-5:1:1 may be said to have a "14/14 bubble."

The "circumference of the bubble" is defined as the sum of the number of nucleotides in the bridge sequence plus the number of nucleotides in the intervening sequence plus the anchor sequence's 3' nucleotide and its complement plus the foot sequence's 5'-terminal nucleotide and its complement. Consequently, the circumference of the bubble formed by the binding of a 24-14/14-5:1:1 multi-part primer (a 14/14 bubble) to the template molecules is 14+14+2+2, which equals 32 nucleotides in length. The listing below lists some of the primers used in the Examples below, utilizing this second format.

Exemplary Primers Utilized in PCR Assays

| Primer | Sequence (5' to 3') | SEQ ID NO: |
|---|---|---|
| EGFR L858R | | |
| Conventional Forward | CTGGTGAAAACACCGCAGCATGTC | 27 |
| Conventional Reverse | GCATGGTATTCTTTCTCTTCCGCA | 3 |
| 24-14/14-5:1:1 | CTGGTGAAAACACCGCAGCATGTCGCACGAGTGAGCCCTGGGCGG | 6 |
| 24-14/14-4:1:1 | TGGTGAAAACACCGCAGCATGTCACACGAGTGAGCCCCGGGCGG | 7 |
| 24-14/14-5:1:1 | CTGGTGAAAACACCGCAGCATGTCGCACGAGTGAGCCCTGGGCGG | 6 |
| 24-14/14-6:1:1 | ACTGGTGAAAACACCGCAGCATGTTGGAGCTGTGAGCCTTGGGCGG | 8 |
| 24-14/14-6:1:0 | ACTGGTGAAAACACCGCAGCATGTTGCACGAGTGAGCCTTGGGCG | 11 |
| 24-14/14-5:1:1 | CTGGTGAAAACACCGCAGCATGTCGCACGAGTGAGCCCTGGGCGG | 6 |
| 24-14/14-4:1:2 | TGGTGAAAACACCGCAGCATGTCACACGAGTGAGCCACGGGCGGG | 12 |
| 24-14/14-3:1:3 | GGTGAAAACACCGCAGCATGTCAAACGAGTGAGCCACAGGCGGGC | 13 |
| 24-14/14-2:1:4 | GTGAAAACACCGCAGCATGTCAAGGAAGTGAGCCACAAGCGGGCC | 14 |
| 24-14/14-1:1:5 | TGAAAACACCGCAGCATGTCAAGACAGACTGACCCAAACGGGCCA | 15 |
| 24-10/10-5:1:1 | TGAAAACACCGCAGCATGTCAAGACACTCAGCCCTGGGCGG | 10 |
| 24-14/14-5:1:1 | CTGGTGAAAACACCGCAGCATGTCGCACGAGTGAGCCCTGGGCGG | 6 |
| 24-18/18-5:1:1 | CGTACTGGTGAAAACACCGCAGCACTGACGACAAGTGAGCCCTGGGCGG | 9 |
| 24-18/10-5:1:1 | TGAAAACACCGCAGCATGTCAAGACACACGACAAGTGAGCCCTGGGCGG | 16 |
| 24-16/12-5:1:1 | GGTGAAAACACCGCAGCATGTCAATCCAACAAGTGAGCCCTGGGCGG | 17 |
| 24-14/14-5:1:1 | CTGGTGAAAACACCGCAGCATGTCGCACGAGTGAGCCCTGGGCGG | 6 |
| 24-12/16-5:1:1 | TACTGGTGAAAACACCGCAGCATGGACGACGAGCCCTGGGCGG | 18 |
| 24-10/18-5:1:1 | CGTACTGGTGAAAACACCGCAGCACTGACGGCCCTGGGCGG | 19 |
| B-raf V600E | | |
| 24-14/14-5:1:1 | AGACAACTGTTCAAACTGATGGGAAAACACAATCATCTATTTCTC | 20 |
| Conventional Reverse | ATAGGTGATTTTGGTCTAGC | 22 |

The bridge sequence within each SuperSelective primer is underlined, and the interrogating nucleotide in its foot sequence is represented by an underlined bold letter. The primers are arranged into groups that reflect their use in comparative experiments.

4. Uses This invention is not limited to particular intended targets, particular amplification methods, or particular instruments. For comparative purposes we present in Examples 1-8 several series of experiments that utilize the same intended target, EGFR mutation L858R, a homogeneous PCR assay starting with plasmid DNA, utilizing SYBR® Green detection, and using the same thermal cycler, a Bio-Rad IQ5 spectrofluorometric thermal cycler. We have performed other assays that gave results consistent with those reported in the Examples. Such assays have utilized other intended targets, including human EGFR mutant T790M and human B-raf mutant V600E; have utilized genomic DNA; have included detection with molecular beacon probes; have utilized different PCR parameters; and have utilized a different instrument, the ABI PRISM 7700 spectrofluorometric thermal cycler.

Figure 5:
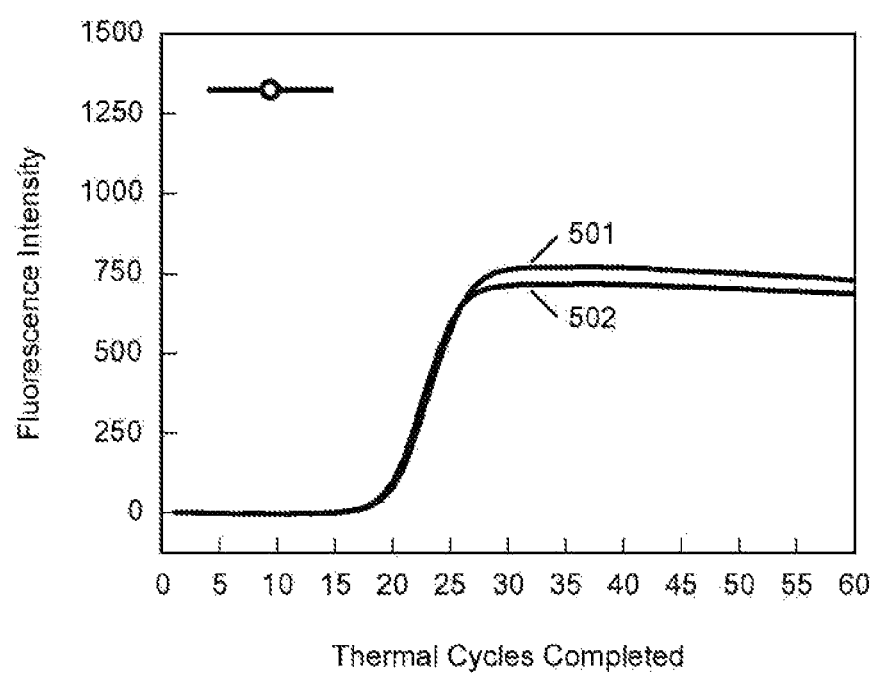
FIG. 5 shows the real-time fluorescence results obtained with a conventional linear primer and either 1,000,000 intended target sequences or 1,000,000 unintended, mismatched target sequences that differ from each other at a single nucleotide located in the middle of the sequence to which the primers bind.

Example 1 is a control assay in which a conventional PCR forward primer 21-nucleotides long was used to amplify a perfectly matched intended target sequence and also to amplify an unintended, mismatched target sequence differing by a single-nucleotide polymorphism that is located near the middle of sequence to which the primer binds (here, as in other Examples, a conventional PCR reverse primer was used as well). Homogeneous detection of double-stranded amplification products (or double-stranded "amplicons") was enabled by the inclusion of SYBR Green® in the initial amplification reaction mixture, which binds to double-stranded amplicons is such a manner as to significantly increase their fluorescence. Consequently, the intensity of the SYBR Green® fluorescence measured at the end of the chain elongation stage of each PCR amplification cycle provides an accurate indication of the number of amplicons present. Real-time kinetic fluorescence curves (fluorescence intensity versus amplification cycle number) presented in FIG. 5 show that the amplifications produced sufficient double-stranded product, on the order of $10^{12}$ amplicons, to give a detectable signal above background (the threshold cycle, abbreviated "$C_T$") at the point where roughly 20 PCR cycles had been carried out, which is typical for a PCR assay starting with $10^6$ templates. FIG. 5 also shows that the forward primer had little selectivity in favor of the intended target over the unintended, mismatched target, that is, there was no significant delay in the threshold cycle ($C_T$) when starting with the mismatched target. Thermodynamically, there is little difference in the stability of the perfectly complementary hybrids compared to the stability of the mismatched hybrids (resulting in virtually no observable delay in the appearance of amplicons made from the slightly less probable-to-form mismatched primer-target hybrids).

Example 2 describes two additional controls, wherein the substituted nucleotide in the mismatched target was placed first at the 3' terminal nucleotide of the conventional forward primer, the well-known ARMS technique, and then at one nucleotide inboard from the 3' terminal nucleotide of the conventional forward primer. We sometimes refer to the location of the nucleotide within a primer sequence that will be opposite the nucleotide in the target where a single-nucleotide polymorphism can be present or absent as the "interrogating nucleotide." Real-time kinetic curves for these controls are presented in FIG. 6, where it can be seen that, with the intended target, the $C_T$ remained in the vicinity of 20 cycles, indicating that the amplification reaction was just as efficient for the intended target as the amplification reported in Example 1. However, with the mismatched target, the $C_T$ was delayed by several cycles. In the case of the primer with the interrogating nucleotide at the 3'-terminus of the foot sequence, FIG. 6A, the delay (11 cycles) was roughly 10 cycles, which indicates a selectivity in favor of the perfectly matched intended target of a thousand fold ($2^{10}$ is 1,024). In the case of the interrogating nucleotide being at the penultimate position from the 3' end of the foot sequence, the $C_T$ was somewhat less, about 8 cycles. Comparing Examples 1 and 2, one sees that the efficiency of amplification of the intended target is not reduced by placing the interrogating nucleotide at or near the 3' end of the primer, but selectivity for the intended target over the unintended target differing by a single nucleotide is improved. We understand that selectivity is limited because, due to keto-enol tautomerism, some base pairing of the mismatched interrogating nucleotide with the non-complementary nucleotide in the target sequence occasionally occurs, and therefore some undesirable extension does take place, so the probability of generating an amplicon is the product of the probability of a hybrid being formed times the probability that the resulting hybrid forms a structure that can be extended.

Example 3 shows the same experiment with a multi-part primer according to this invention. We describe the primer used here as 24-14-5:1:1. The first number, 24, is the nucleotide length of the anchor sequence. The second number, 14, is the nucleotide length of the bridge sequence (and in this experiment, as in the other experiments that are described herein, except where we explicitly indicate otherwise, the intervening sequence in the target is the same length as the bridge sequence). The last three numbers, 5:1:1, describe the foot sequence, giving the number of nucleotides that are 5' of the interrogating nucleotide(s), then the number of interrogating nucleotides (which is 1 for all of the experiments described herein), and finally the number of nucleotides that are 3' of the interrogating nucleotide(s). Thus, in this case, the foot was seven nucleotides long with a penultimate interrogating nucleotide. The results of these real-time assays, utilizing the intensity of SYBR Green® fluorescence to measure the number of amplicons present after the completion of each thermal cycle (determined at the end of the chain elongation stage of each cycle) are presented in FIG. 7. Comparing FIGS. 5 and 7, one sees that the $C_T$ with the intended, perfectly matched target is delayed, in this case by about 3 cycles. One also sees that the $C_T$ with the unintended target (containing a single-nucleotide polymorphism that is not complementary to the interrogating nucleotide in the foot) is even more delayed, giving a $\Delta C_T$ of about 19 cycles between the intended target sequence and the unintended target sequence, which is approximately a 500,000-fold difference in selectivity ($2^{19}$ is 524,288).

While not wishing to be bound by any theory, we believe the following to be true:

A. Even though the foot sequence is tethered to the template by the anchor hybrid, the foot is so small, and it is separated from the anchor hybrid by such a large bubble (comprising the bridge sequence of the primer and the intervening sequence in the template), and the annealing temperature is so high for a short foot sequence, that at any given moment (under the equilibrium conditions of the annealing stages of the PCR assay), only a very small portion of the template molecules that are present in the sample being tested are hybridized to the foot at any given moment.

B. Moreover, the hybrids that do form between the foot and the target are relatively weak, so the mean time during which they persist is very short (perhaps a hundred microseconds).

C. As a consequence of both the reduced probability of a hybrid existing at any given moment, and the reduced mean persistence times of the resulting weak hybrids, there is an extremely low probability of a stable (extendable) complex being formed between a hybrid (even a perfectly complementary hybrid) and a DNA polymerase molecule.

D. This is seen in PCR assays carried out with preferred multi-part primer designs as an approximately 10-cycle delay in the appearance of the amplicons made from perfectly complementary ("mutant") targets (that is, instead of a $C_T$ of about 20, as occurs when conventional linear primers are utilized with $10^6$ perfectly complementary targets), the Ct is about 30. An increase of 10 thermal cycles in the $C_T$ value indicates that the probability of forming a stable complex between a DNA polymerase molecule and a perfectly complementary foot hybrid is $1/1,000$ less probable than when a conventional linear primer is utilized under the same reaction conditions.

E. Under these same PCR conditions, utilizing the same preferred multi-part primer design, the $C_T$ value obtained with mismatched ("wild-type") targets occurs almost 20 cycles later than the $C_T$ value that occurs with a perfectly complementary target. There is thus an approximately 30-cycle delay in the appearance of amplicons from these mismatched targets compared to the $C_T$ value that would have occurred under the same conditions had a conventional linear primer been used in place of the multi-part primer. Thus, the probability of forming a stable complex between a DNA polymerase molecule and a hybrid containing a foot sequence bound to a mismatched foot target sequence is immensely lower. This 30-cycle increase in the $C_T$ value indicates that the probability of forming a stable complex between a DNA polymerase molecule and a mismatched foot hybrid is $1/1,000,000,000$ less probable than when a conventional linear primer is utilized under the same reaction conditions.

F. This dramatically lower probability of forming extendable complexes between an unintended target sequence and a DNA polymerase molecule is the product of the following discriminatory elements: (i) the lower stability of the mismatched hybrid (compared to the stability of the perfectly complementary hybrid) markedly decreases the fraction of mismatched hybrids present at any given moment (compared to the fraction of perfectly complementary hybrids that can be present at any given moment); and (ii) the lower stability of the mismatched hybrids results in a shorter mean persistence time for the hybrids, thereby markedly decreasing the ability of a DNA polymerase molecule (subject to constant Brownian motion) to find a hybrid with which to form a stabilized complex.

Example 4 shows that with the assay of Example 3, one can readily distinguish the different results obtained with a sample containing only $10^6$ copies of the unintended target sequence and a sample containing ten or more copies of the intended target sequence in the presence of $10^6$ copies of the unintended target sequence. The real-time PCR results obtained for a dilution series ($10^6$, $10^5$, $10^4$, $10^3$, $10^2$, $10^1$ copies of the intended target sequence in a reaction mixture containing $10^6$ copies of the unintended target sequence) are presented in FIG. 8, and the $C_T$'s determined for those results are presented in FIG. 9, where they are plotted against the logarithm of the starting copy number of the intended target sequence. Referring to those figures, one sees that the $C_T$ of SYBR Green® fluorescence is delayed by approximately 10 cycles for every thousand-fold decrease in the concentration of the intended target, and that a sample with 10 copies of the intended target sequence plus $10^6$ copies of the unintended target sequence is distinguished from a sample with no intended target sequence and $10^6$ copies of the unintended target sequence; that is, detection of one mutant sequence in a population of 100,000 copies of the corresponding wild-type sequence is enabled. Further, the assay is quantitative, with the threshold cycle corresponding to the logarithm of the number of mutant copies in the starting reaction mixture.

Figure 8:
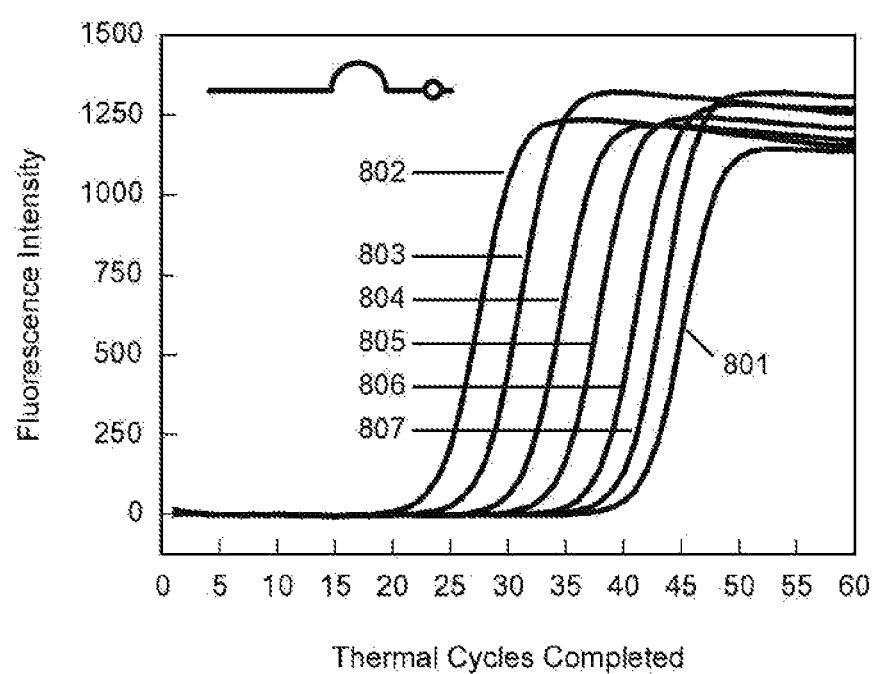
FIG. 8 shows the real-time fluorescence results obtained with a multi-part primer according to this invention in a series of reactions that each contains 1,000,000 unintended target sequences and either: 0; 10; 100; 1,000; 10,000; 100,000; or 1,000,000 intended target sequences.
Figure 9:
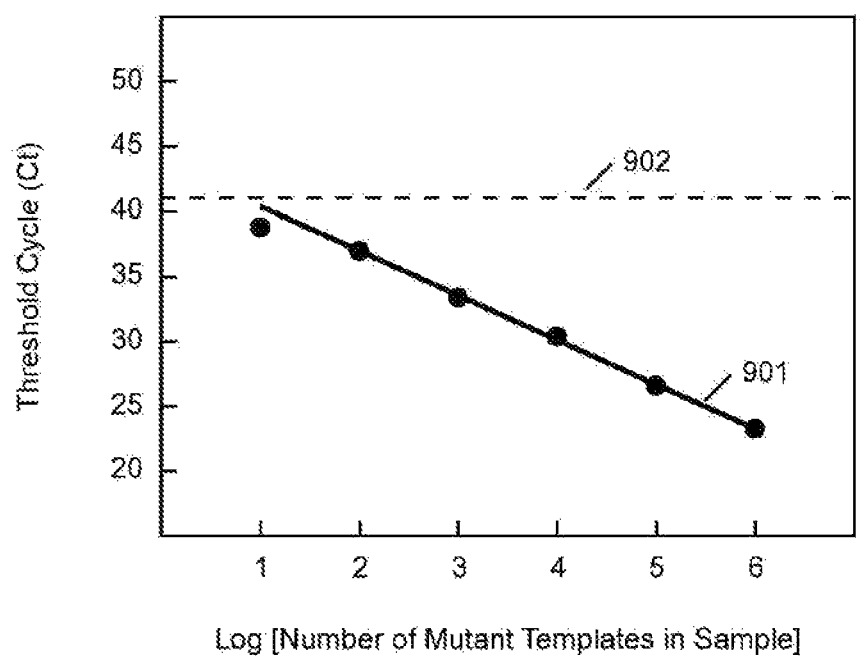
FIG. 9 is a graph showing the inverse linear relationship between the threshold cycle observed for each reaction shown in FIG. 8 versus the logarithm of the number of intended targets present in each reaction, and a dotted line in the figure indicates the threshold cycle obtained for the reaction that contained 1,000,000 unintended target sequences and no intended target sequences.

These results confirm the following aspects of the use of selective primers according to this invention:

A. Once a multi-part primer forms a hybrid that binds to a DNA polymerase during an annealing stage of a PCR assay, that stabilized hybrid is extended during the elongation stages of the PCR assay, and the resulting amplicons are then amplified with high efficiency (just as though the reaction was carried out with classical linear primers). This can be seen by the fact that a reduction in the number of mutant templates originally present in a sample by a factor of 1,000 results in a delay in the appearance of a significant number of amplicons by approximately 10 thermal cycles (e.g., in the experiment whose results are shown in FIG. 8 and FIG. 9, the $C_T$ value of a sample possessing 100,000 mutant templates was approximately 27 and the $C_T$ value of a sample possessing 100 mutant templates was approximately 37). If the number of amplicons present efficiently doubles every thermal cycle, then after ten cycles there should be 1,024 times as many amplicons (i.e., $2^{10}$). These results confirm that the amplicons generated from the mutant templates present in the sample being tested are then amplified efficiently.

B. Efficient amplification of the amplicons occurs because once a multi-part primer is incorporated into the 5' end of a product amplicon (the "plus" amplicon strand), the complementary amplicon generated in the next cycle of synthesis (the "minus" amplicon strand) possesses a sequence at its 3' end that is perfectly complementary to the entire sequence of the multi-part primer. Consequently, with respect to amplicons (as opposed to the original template molecules), the multi-part primers behave as though they were classical linear primers for the further amplification of the amplicons.

C. The extraordinarily selective generation of amplicons from the perfectly complementary mutant templates present in the sample being tested (compared to the generation of amplicons from the mismatched wild-type templates present in the sample being tested), combined with the efficient amplification of the amplicons by the primers once the amplicons are synthesized, enables the resulting real-time data to be used to quantitatively measure the number of mutant template molecules that were present in the sample being tested.

There is an inverse linear relationship (in exponential amplification reactions such as PCR assays) between the logarithm of the number of target molecules present in a sample being tested and the number of thermal cycles that it takes to synthesize a predetermined number of amplicons, as reflected in the $C_T$ values obtained from samples containing different numbers of mutant template molecules. See Kramer & Lizardi (1989) Nature 339:401-402. The linearity of a plot of $C_T$ versus the logarithm of the number of intended (mutant) template molecules present in each sample being tested, as for example in the experiment whose results are shown in FIG. 9, indicates that there are no significant amplicons being generated from the wild-type templates (even though 1,000,000 wild-type template molecules were present in each sample). Had there been significant numbers of amplicons generated from the wild-type templates, the $C_T$ values for samples containing only a few mutant template would have been lower (that is, the results would not have formed a straight line, because the appearance of unwanted amplicons synthesized from the abundant unintended target molecules would obscure the appearance of amplicons from very rare intended target molecules).

Figure 10:
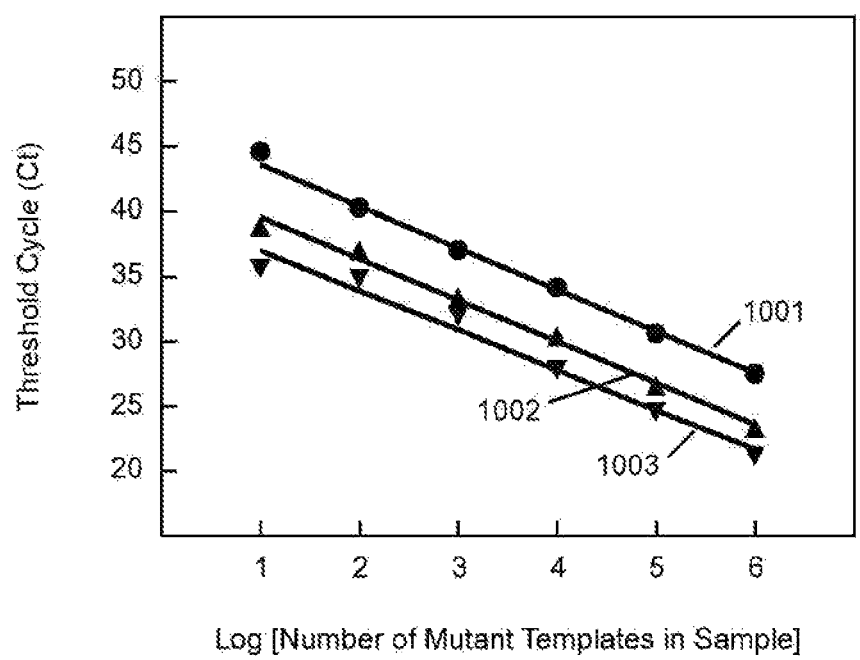
FIG. 10 is a graph showing the results that were obtained with the same dilution series used for the experiment shown in FIG. 8 and FIG. 9, utilizing three otherwise identical multi-part primers whose foot was either 6, 7, or 8 nucleotides in length (where the interrogating nucleotide was located at the penultimate position in each foot sequence).

As reported in Example 5, we investigated the effect of the length of the foot of a multi-part primer on the amplification reaction using the assay of Example 4 with a series of three probes: 24-14-4:1:1, 24-14-5:1:1 and 24-14-6:1:1. The length of the anchor sequence was maintained at 24 nucleotides. The length of the bridge sequence was maintained at 14 nucleotides, the same single-nucleotide difference between the target sequences was maintained, and the location of the interrogating nucleotide was maintained at the penultimate position from the 3' terminus of the foot. The length of the foot sequence was varied from 6 nucleotides to 7 nucleotides to 8 nucleotides by changing the number of nucleotides 5' of the location of the interrogating nucleotide from 4 to 5 to 6. The $C_T$ values that were obtained are summarized in Table 1 and plotted in FIG. 10 against the logarithm of the starting copy number of the intended target sequence. Straight lines 1001 (foot length 6), 1002 (foot length 7) and 1003 (foot length 8) are fitted to the data. It can be seen that all three primers provided quantitative results, as reported above for FIG. 9. It can also be seen that fitted lines 1001, 1002 and 1003 are close to parallel, indicating the same quantitative relationship between $C_T$ and the logarithm of the starting copy number for all three foot lengths. FIG. 10 also shows that shortening the length of the foot delays the $C_T$, but as seen in FIG. 10, shortening the length of the foot also gives a better straight-line fit of the data from $10^6$ to $10^1$ copies of the intended target sequence (that is, the shorter the foot length, the less likely it is that amplicons synthesized from abundant unintended target molecules in a sample being tested will obscure the amplicons synthesized from rare intended target molecules that are present in the same sample).

Figure 11:
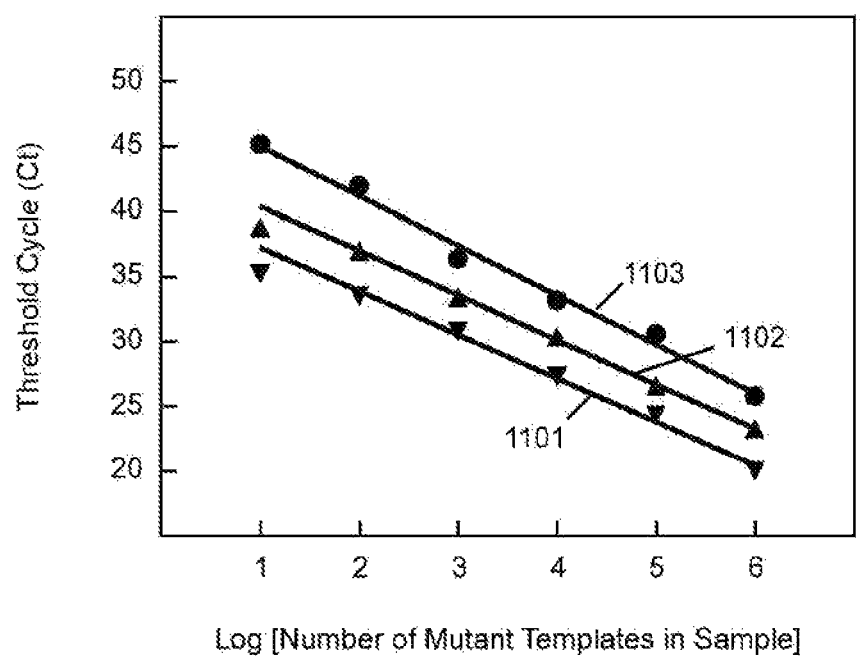
FIG. 11 is a graph showing the results that were obtained with the same dilution series used for the experiment shown in FIG. 8, FIG. 9, and FIG. 10, utilizing three multi-part primers whose bridge sequences form bubbles of different circumferences with an identical-length intervening sequence in the target molecules.

As reported in Example 6, we also investigated the effect on amplification of the circumference of the bubble formed by the bridge sequence of a multi-part primer and the intervening sequence of the intended and unintended target sequences, using the assay of Example 4 with a series of three primers: 24-10-5:1:1, 24-14-5:1:1, and 24-18-5:1:1. We maintained the length of the anchor sequence at 24 nucleotides; we maintained the foot sequence at 5:1:1; and we varied the length of the bridge sequence from 10 to 14 to 18 nucleotides, and chose the sequence of the anchor for each multi-part primer so that the intervening sequence in the target would be the same length as the bridge in that primer. Consequently, the circumference of the bubble (expressed in nucleotides) formed by each of the three primers when their foot sequence was hybridized to a target (including the four nucleotides contributed by the anchor hybrid and the foot hybrid) were 24, 32, and 40, respectively. The $C_T$ values obtained are summarized in Table 2 and plotted in FIG. 11 against the logarithm of the starting copy number of the intended target sequence. Straight lines 1101 (bubble circumference 24), 1102 (bubble circumference 32) and 1103 (bubble circumference 40) are fitted to the data. It can be seen that all three primers provided quantitative results, as reported above for FIG. 9 and FIG. 10. It can also be seen that fitted lines 1101, 1102 and 1103 are close to parallel, indicating the same quantitative relationship between $C_T$ and the logarithm of starting copy number for all three bubble circumferences. FIG. 11 also shows that increasing the circumference of the bubble delays the $C_T$, but as seen in FIG. 11, increasing the bubble circumference gives a better straight-line fit of the data from $10^6$ to $10^1$ copies of the intended target sequence (that is, the bigger the bubble, the less likely it is that amplicons synthesized from abundant unintended target molecules in a sample being tested will obscure the amplicons synthesized from rare intended target molecules that are present in the same sample).

These experimental observations demonstrate that shorter foot lengths and/or larger bubbles cause hybrid formation to be considerably less likely, and shorter foot lengths and/or larger bubbles result in increased selectivity against mismatched wild-type templates, which is evidenced by the enhanced linearity of plots of $C_T$ versus the logarithm of the number of intended target molecules. In order to gain an understanding of why this is so, we examined the thermodynamics of formation of a foot hybrid under the equilibrium conditions that exist during the annealing stages of PCR assays. Here is our understanding:

A. There is a very high concentration of multi-part primers present in our PCR assays (as there needs to be sufficient multi-part primers available to be incorporated into the approximately $10^{13}$ amplicons that can be synthesized in each reaction). Consequently, virtually every template molecule is rapidly bound to the anchor sequence of a multi-part primer under the equilibrium conditions that exist at the annealing stages of these PCR assays. Moreover, because the anchor sequence is long (for example, 24 nucleotides), the bond between the anchor sequence and the template molecules is very strong and persists, on average, for a long time (measured, perhaps, in minutes). At equilibrium, in a very small portion of these anchored complexes, the short foot sequence is also hybridized to the template molecule. At any given instant, the concentration of anchored complexes whose foot sequence is not hybridized is "[A]", and the concentration of anchored complexes whose foot sequence is hybridized is "[B]". The classical equilibrium constant ("k") that describes the interrelationship these two states is:

$$k=[B]/[A] \quad \text{Equation 1}$$

Thermodynamically, the probability of forming a hybrid at equilibrium depends on both hybrid strength (enthalpy) and on the physical relationship that determines the probability that the two sequences will be able to interact to form a hybrid (entropy). The equilibrium constant can be determined from the change in enthalpy that occurs upon conversion of an anchored complex whose foot sequence is not hybridized to a foot sequence that is hybridized ($\Delta H$) and from the change in entropy that occurs upon conversion of an anchored complex whose foot sequence is not hybridized to a foot sequence that is hybridized ($\Delta S$), according to the following classical formula:

$$(\Delta H - T\Delta S) = -RT \ln(k) \quad \text{Equation 2}$$

where R is the thermodynamic gas constant, T is the temperature expressed in degrees Kelvin, and ln(k) is the natural logarithm of the equilibrium constant. Rearranging this equation to obtain an expression for k:

$$k = e^{-(\Delta H - T\Delta S)/RT} \quad \text{Equation 3}$$

where e=2.71828. For the very same reaction, the fraction of complexes that possess a hybridized foot sequence ($\Theta$) is described by the following equation: $\Theta=[B]/([A]+[B])$. However, as [B] becomes very small (as is the case for reactions employing multi-part primers), Θ approaches 0, and the equation for Θ can be expressed as follows:

$$\Theta \cong [B]/[A] \qquad \text{Equation 4}$$

Since the expression for Θ in Equation 4 is virtually identical to the expression for k in Equation 1, we can substitute Θ for k in Equation 3, to obtain an equation that relates the very low abundance of primer-template complexes that possess a hybridized foot (Θ) to the classical thermodynamic parameters, ΔH and ΔS, as follows:

$$\Theta = e^{-(\Delta H - T\Delta S)/RT} \qquad \text{Equation 5}$$

For nucleic acid hybridization reactions that occur under PCR conditions, the quantity (ΔH−TΔS) is a positive value, so e is raised to a negative number, giving a fractional value for Θ. The smaller the value of (ΔH−TΔS), the smaller is the fraction Θ. Moreover, during the annealing stages of a PCR reaction, T is constant. Therefore, to understand how Θ is altered as a consequence of alterations in the design of multi-part primers, we need only consider the magnitude of the values of ΔH and ΔS for each primer design, in order to understand the effect of that design when the multi-part primers are hybridized to intended targets compared to when they are hybridized to unintended targets.

B. Entropy is a measure of the number of conformationally distinct states that a molecular complex can form. Therefore, when the foot of an anchored complex hybridizes to its target, the number of topologically distinct states that the complex can form goes from a high number to a low number. Therefore, the change in entropy (ΔS) upon forming a foot hybrid has a negative value.

C. Enthalpy is a measure of the stability of a molecular complex, expressed in terms of the amount of energy present in the solution containing the complex. Since high temperatures are required to dissociate a nucleic acid hybrid, heat energy is added when the complex is broken apart and heat energy is released upon formation of the complex. Therefore, the change in enthalpy (ΔH) upon formation of a foot hybrid also has a negative value.

D. The fraction of complexes that possess a hybridized foot sequence (Θ), when multi-part primers are used in PCR assays, is well described by Equation 5. In the experiments described above, in which the length of the foot was varied or the circumference of the bubble was varied, the only variables are ΔH and ΔS. For the formation of foot hybrids, ΔH and ΔS are negative, and the quantity (ΔH−TΔS), which is known as the Gibbs free energy (ΔG), is positive. Consequently, the quantity TΔS is more negative than ΔH. In terms of calculating the fraction of complexes that possess a hybridized foot sequence (Θ), the smaller the negative magnitude of ΔH, the smaller will be Θ. Similarly, the greater the negative magnitude of ΔS, the smaller will be Θ.

E. In order to determine the effect of different foot lengths on the fraction of complexes that possess a foot hybrid (Θ), it is necessary to realize that, all else being equal, ΔH is less negative the shorter is the length of the foot hybrid. Consequently, the shorter the length of the foot hybrid, the lower is the proportion, at any given moment, of the primer-target complexes that possess foot hybrids.

F. Similarly, in order to determine the effect of different bubble circumferences on the fraction of complexes that possess a foot hybrid (Θ), it is necessary to realize that, all else being equal, ΔS is more negative the greater the circumference of the bubble. Consequently, the greater the circumference of the bubble, the lower is the proportion, at any given moment, of the primer-target complexes that possess foot hybrids.

G. Given these realizations, now let's look at how the design of the foot sequences in multi-part primers contributes to the discrimination between perfectly complementary target sequences (intended target sequences) and mismatched target sequences (unintended target sequences). For example, the multi-part primers used for the experiment whose results are shown in FIG. 8 and FIG. 9 possessed feet of different lengths ("6:1:1" or "5:1:1" or "4:1:1"). These designations indicate that the overall length of each foot was either 8 nucleotides, 7 nucleotides, or 6 nucleotides, respectively, with the interrogating nucleotide (that is either complementary to the corresponding nucleotide in the intended target sequence or not complementary to the corresponding nucleotide in the unintended) being located at the penultimate position from the 3' end of the primer.

H. The reason that we locate the key nucleotide at the penultimate position is that we believe that when the penultimate base pair cannot form (due to a mismatch) that the terminal base pair also cannot form (even though the 3' nucleotide of the foot is complementary to the corresponding nucleotide in the target), because an isolated base pair is extremely unlikely to be stable at the annealing temperature of a PCR assay (approximately 60° C.). Thus, for a given foot sequence, a mismatched hybrid will be two base pairs shorter than a perfectly complementary hybrid.

I. Here is what this means (conceptually): In order to illustrate the point, assume that the temperature (T)=1, and assume that the gas constant (R)=1, because they are constants. Imagine that the ΔH value for the formation of a perfectly complementary hybrid with a 6:1:1 foot is −16 and that the ΔH value for the formation of the shorter mismatched hybrid with a 6:1:1 foot is −12. Let's also imagine that the ΔS value for both of these hybrids, which is determined by the circumference of the bubble, is −20. Consequently, the ΔG value for the perfectly complementary hybrid is 4 (calculated as 20−16), and the ΔG value for the mismatched hybrid is 8 (calculated as 20−12). Plugging these values into equation 5, the conceptual value of Θ for the hybrid formed with an intended target ($\Theta_m$) equals $e^{-4}$, which has the value 0.0183. By comparison, the conceptual value of Θ for the hybrid formed with unintended target ($\Theta_w$) equals $e^{-8}$, which has the value 0.000335. There is thus, in this conceptual example, the abundance of perfectly complementary hybrids is 54.6 times greater than the abundance of mismatched hybrids. Although this calculation illustrates that the use of a multi-part primer according to this invention results in a much lower probability of a foot hybrid formed with an unintended target being present (at any given moment) compared to the probability of a foot hybrid formed with intended target being present (at any given moment), and although this difference certainly results in a greater delay in the $C_T$ for amplicons synthesized from the unintended targets compared to the $C_T$ for amplicons synthesized from the intended targets, the actual values of $\Theta_m$ and $\Theta_w$ will be different from this conceptual example.

J. Now let's do the same conceptual calculation for a multi-part primer possessing a 5:1:1 foot. In this case, the ΔH value for the formation of a perfectly complementary hybrid with a 5:1:1 foot is −14 and the ΔH value for the formation of a mismatched hybrid with a 4:1:1 foot is −10; and the resulting ΔG values (for the same size bubble, for which ΔS=−20) are as follows: the ΔG value for the perfectly complementary hybrid is 6 (calculated as 20−14=6), and the ΔG value for the mismatched hybrid is 10 (calculated as 20−10). Plugging these values into equation 5, the conceptual value of θ for the hybrid formed with an intended target ($\Theta_m$) equals $e^{-6}$, which has the value 0.00248. By comparison, the conceptual value of Θ for the hybrid formed with unintended target ($\Theta_w$) equals $e^{-10}$, which has the value 0.0000454. Surprisingly, in this conceptual example, the abundance of perfectly complementary hybrids is also 54.6 times greater than the abundance of mismatched hybrids.

K. Now let's do the same conceptual calculation for a multi-part primer possessing a 4:1:1 foot. In this case, the ΔH value for the formation of a perfectly complementary hybrid with a 4:1:1 foot is −12 and the ΔH value for the formation of a mismatched hybrid with a 4:1:1 foot is −8; and the resulting ΔG values (for the same size bubble, for which ΔS=−20) are as follows: the ΔG value for the perfectly complementary hybrid is 8 (calculated as 20−12=8), and the ΔG value for the mismatched hybrid is 12 (calculated as 20−8). Plugging these values into equation 5, the conceptual value of Θ for the hybrid formed with an intended target ($\Theta_m$) equals et which has the value 0.000335. By comparison, the conceptual value of Θ for the hybrid formed with unintended target ($\Theta_w$) equals $e^{-12}$, which has the value 0.00000614. And even more surprisingly, in this conceptual example, the abundance of perfectly complementary hybrids is also 54.6 times greater than the abundance of mismatched hybrids. Therefore, we conclude that, even though shorter feet result in lower values for Θ, and even though shorter feet result in increased $C_T$ values, from a strictly thermodynamic viewpoint, there is no reason to believe that shorter foot sequences lead to enhanced discrimination between intended target sequences and unintended target sequences.

L. Furthermore, even though increased bubble circumference also lowers the value of Θ, it is clear that increasing the circumference of the bubble, though making the formation of hybrids less likely, does not alter the equilibrium ratio of foot hybrids formed from intended targets compared to foot hybrids formed from unintended hybrids.

M. In terms of classical thermodynamic analysis, it can be shown that for any given multi-part primer for which the fraction of molecular complex that form foot hybrids is extremely low, the ratio of the fraction of foot hybrids formed with the intended targets ($\Theta_m$) compared to the fraction of foot hybrids formed with the unintended targets ($\Theta_w$) is not affected by increasing the circumference of the bubble (which alters ΔS), nor is it affected by decreasing the length of the foot (which alters ΔH), but rather, these changes decrease the values of both $\Theta_w$ and $\Theta_m$, but do not alter the ratio ($\Theta_m/\Theta_w$), which is a function of the difference in the enthalpies ($\Delta H_m - \Delta H_w$). Consequently, from a classical thermodynamic point of view, the only thing that affects the relative abundance of the intended hybrids compared to the unintended hybrids is the difference in their enthalpy values, and this difference is a consequence of the difference in the number of base pairs formed, which is the same no matter what the length of the foot is. The thermodynamic equation describing the ratio ($\Theta_m/\Theta_w$) is as follows:

$$(\Theta_m/\Theta_w) \cong e^{-(\Delta H_m - \Delta H_w)/RT} \quad \text{Equation 6}$$

The experimental results shown in FIG. 10 and FIG. 11 demonstrate that increasing the circumference of the bubble and decreasing the length of the foot significantly increases the selectivity of the multi-part primers according to this invention, i.e., these alterations in the design of a multi-part primer, though decreasing the abundance of the foot hybrids, significantly increase the discriminatory ratio, ($\Theta_m/\Theta_w$), as this increase in the discriminatory ratio is evidenced by an increase in the difference in $C_T$ values ($\Delta C_T$) between the $C_T$ obtained with $10^6$ intended target molecules and the $C_T$ obtained with $10^6$ unintended target molecules. These observations suggest that there are additional (perhaps non-thermodynamic reasons) for the extraordinary selectivity of the multi-part primers according to this invention.

The explanation for the enhanced selectivity that occurs when the multi-part primers according to this invention are designed so as to decrease the proportion of foot targets that exist at any moment under the equilibrium conditions of the annealing stages of PCR amplification assays cannot lie in the discriminatory consequences of ARMS, because the degree to which DNA polymerase molecules reject hybrids that do not have a base pair that includes the 3'-terminal nucleotide of the primer is the same no matter what the abundance of those primers is. Yet, it is clear from the experimental results that an additional discriminatory mechanism is enabling the extraordinary selectivity that occurs when the primers are designed to rarely form foot hybrids.

While not wishing to be bound by any theory, here is why we believe that decreasing the length of the foot and increasing the circumference of the bubble enhances selectivity. The explanation lies in our unexpected realization that at the relatively high temperatures that exist during the annealing stages of a PCR assay, very short foot hybrids only exist for a very short time before they dissociate (measured, perhaps, in tens or hundreds of microseconds). Moreover, the shorter the hybrid, and the larger the bubble circumference, the shorter is the mean time during which that hybrid exists. We conjecture that the shorter the mean persistence time of a particular type of hybrid, the more unlikely it is for a DNA polymerase molecule to encounter one of those hybrids and to then form a stabilized complex with that hybrid that can undergo chain elongation. The key point here is that whether or not a hybrid will form a stabilized complex with a DNA polymerase molecule is a function of the mean persistence time of that hybrid. We believe that the ratio of the mean persistence time of a perfectly complementary hybrid formed with a particular multi-part primer, compared to the mean persistence time of a mismatched (shorter) hybrid formed with the same type of multi-part primer, is greater when the foot length of the primer is decreased and the bubble circumference of the primer is increased. Thus, more stringent multi-part primer designs (shorter feet, longer bubbles) produce shorter lived hybrids that are considerably less likely to form stabilized hybrids with DNA polymerase molecules. Consequently, shorter foot hybrids are not only less abundant, they have a lowered chance of forming a stabilized complex with a DNA polymerase molecule, and this additional discriminatory property accounts for the extraordinary selectivity of multi-part primers.

Figure 12:
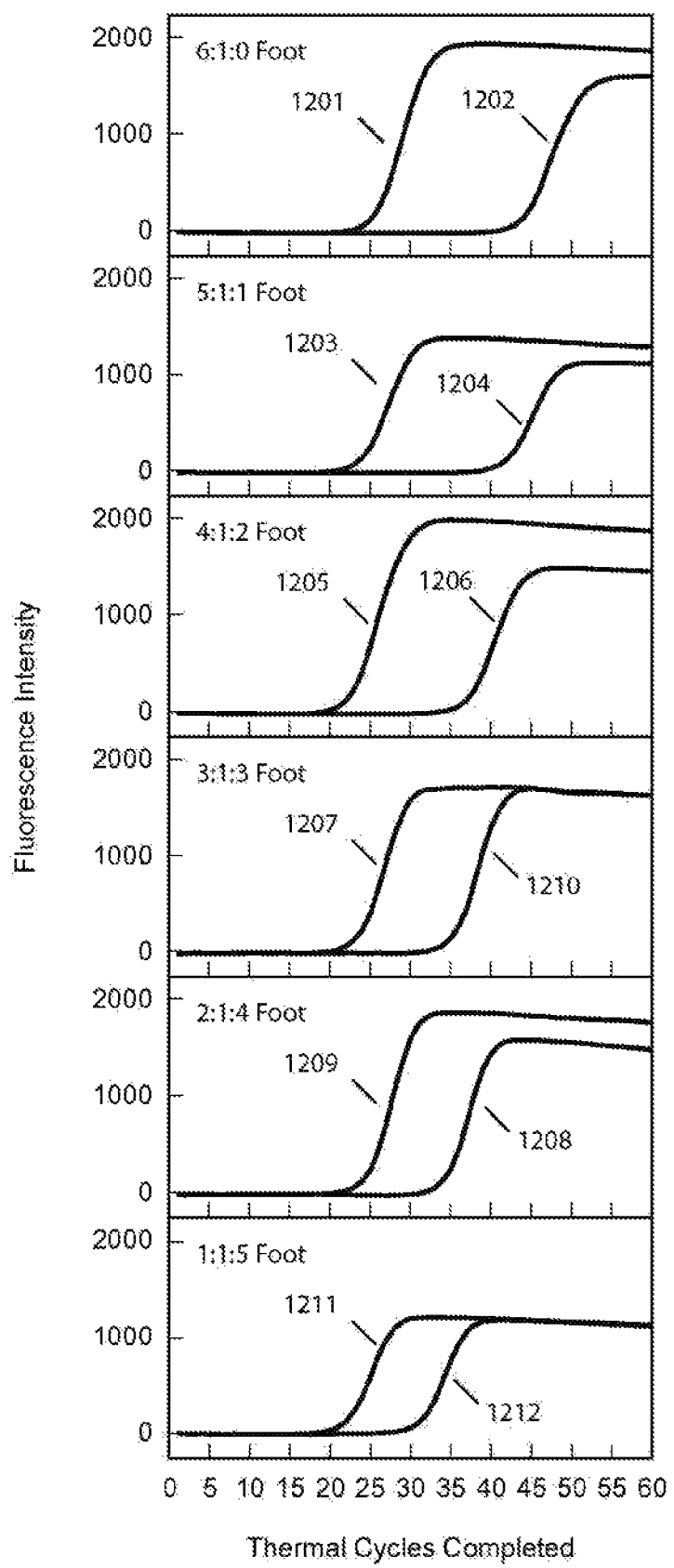
FIG. 12 is a series of graphs showing the real-time fluorescence results obtained with otherwise identical multi-part primers according to this invention and either 1,000,000 intended target sequences or 1,000,000 unintended target sequences (differing from the intended target sequence by a single-nucleotide polymorphism), where the interrogating nucleotide in the foot of the primer (which is complementary to the corresponding nucleotide in the intended target sequence, but not complementary to the corresponding nucleotide in the unintended target sequence) is located at different positions relative to the 3' end of the primer.

As reported in Example 7, we also investigated the effect of varying the location of the interrogating nucleotide in the foot sequence of a multi-part primer according to this invention. We utilized a series of six primers: 24-14-6:1:0, 24-14-5:1:1, 24-14-4:1:2, 24-14-3:1:3, 24-14-2:1:4, and 24-14-1:1:5. We maintained the length of the anchor sequence, the length of the bridge sequence, and the length of the foot sequence (seven nucleotides), only varying the location of the interrogating nucleotide within the foot sequence. The real-time fluorescence results obtained for each of these primers with $10^6$ copies of intended target (mutant) and with $10^6$ copies of unintended target (wild-type) are shown in FIG. 12, and the calculated $C_T$ values are summarized in Table 3. The results show that the window of discrimination ($\Delta C_T$) between intended target sequences and unintended target sequences increases progressively the closer the location of the interrogating nucleotide is to the 3' terminus of the foot. These results indicate that preferred locations for the interrogating nucleotide are at the 3' terminus of the foot (enabling ARMS discrimination) and at the 3'-penultimate nucleotide of the foot (causing two base pairs to be prevented from forming, rather than preventing only one base pair from forming).

Figure 13:
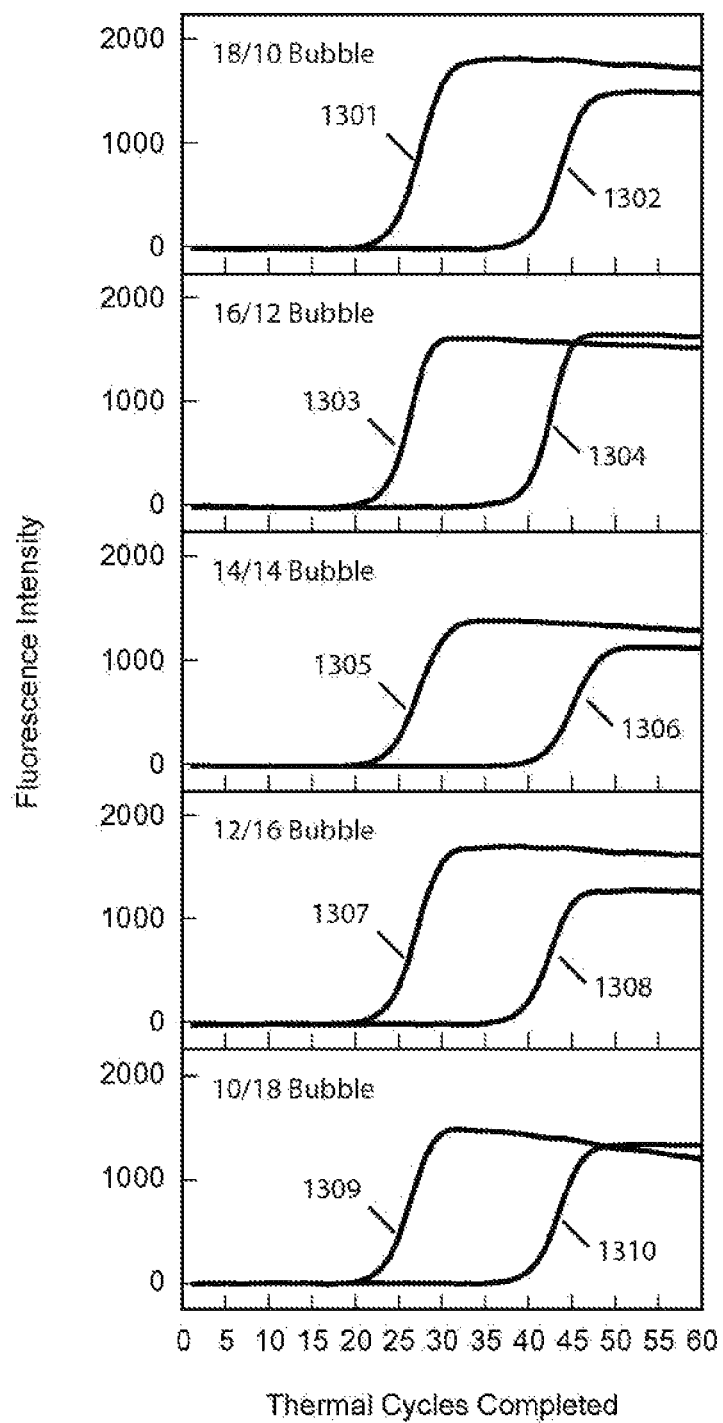
FIG. 13 is a series of graphs showing the real-time fluorescence results obtained with multi-part primers according to this invention and either 1,000,000 intended target sequences or 1,000,000 unintended target sequences differing by a single nucleotide, in which the length of the bridge sequence plus the length of the intervening sequence in the target molecule is held constant (i.e., the circumference of the bubble is the same), but where the symmetry of the bubble formed by the bridge sequence and intervening sequence in the target molecule (relative lengths of those sequences) is varied.

As reported in Example 8, we also investigated the shape of the bubble formed between the bridge sequence of a multi-part primer according to this invention and the intervening sequence in the intended and unintended target sequences. We altered the "shape of the bubble" by choosing the relative lengths of these two sequences. In performing the assay, we utilized a series of primers having an anchor sequence 24 nucleotides long and having a 5:1:1 foot sequence. We maintained the bubble circumference at 32 nucleotides, but we varied the length of the bridge sequence and the length of the intervening sequence (by altering the sequence of the anchor so that upon its hybridization to a template molecule, the intervening sequence would be of the desired length). In addition to testing a multi-part primer that forms a symmetric bubble, that is, a primer possessing a bridge sequence of 14 nucleotides and an anchor sequence that causes the intervening sequence to be 14 nucleotides long (a 14/14 bubble), we tested multi-part primers that produced asymmetric bubbles that had relatively longer bridge sequences (an 18/10 bubble and a 16/12 bubble) and that had relatively shorter bridge sequences (a 12/16 bubble and a 10/18 bubble). The real-time fluorescence results obtained for each of these primers with $10^6$ copies of intended target (mutant) and with $10^6$ copies of unintended target (wild-type) are shown in FIG. 13, and the calculated $C_T$ values are summarized in Table 4. The results show that the window of discrimination ($\Delta C_T$) between intended target sequences and unintended target sequences is largest with a symmetric 14/14 bubble, but only modestly so. Consequently, our most preferred bubbles are symmetric.

Figure 14:
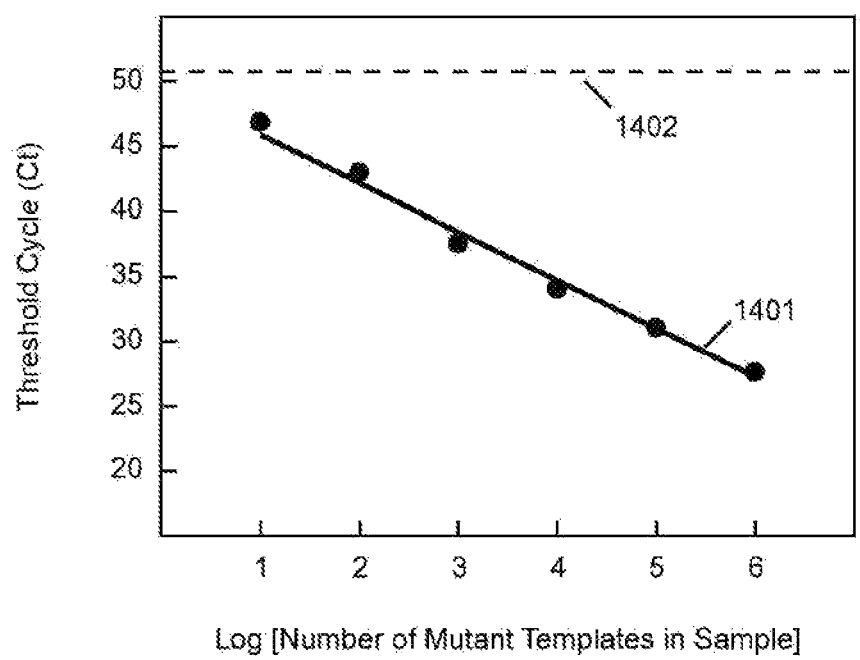
FIG. 14 is a graph showing the inverse linear relationship between the threshold cycle observed and the logarithm of the number of V600E mutant human B-raf target sequences in a series of reactions that each contained 1,000,000 wild-type human B-raf target sequences, and either: 10; 100; 1,000; 10,000; 100,000; or 1,000,000 V600E mutant human B-raf target sequences. The dotted line indicates the threshold cycle obtained for a reaction that contained DNA from 1,000,000 wild-type human B-raf target sequences and no DNA from V600E mutant human B-raf target sequences.

Example 9 reports an experiment utilizing the assay method of Example 4 for a different target, B-raf mutation V600E (instead of EGFR mutation L858R) and a 24-14-5:1:1 multi-part primer for that mutation. FIG. 14 is a graph of $C_T$ versus the log of the starting number of intended target templates. As can be seen from FIG. 14, this assay provided a $\Delta C_T$ of 23.1 cycles between a sample containing $10^6$ WT templates and a sample containing $10^6$ MUT templates in the presence of $10^6$ WT templates, which is even greater than the corresponding $\Delta C_T$ achieved in Example 4.

Figure 15:
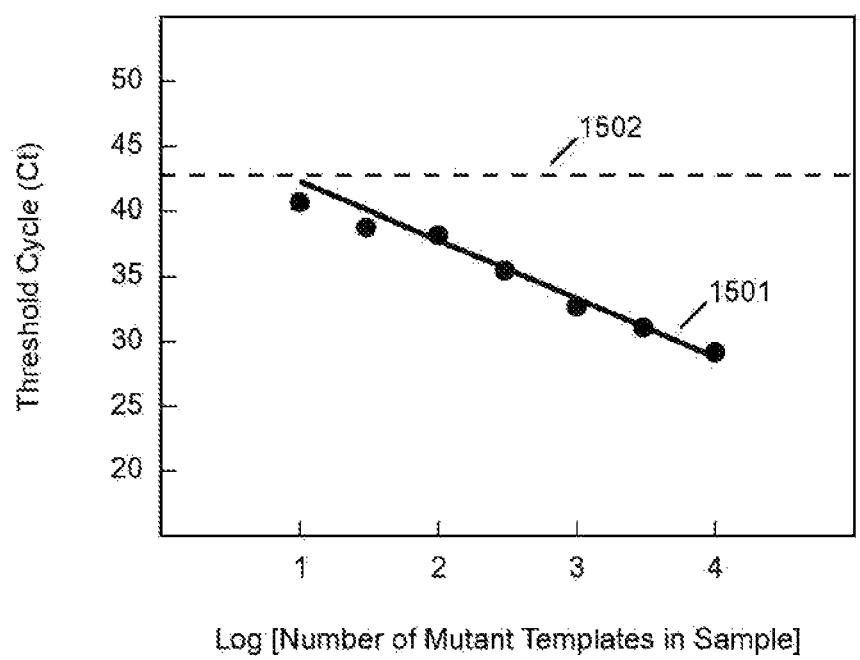
FIG. 15 is a graph showing the inverse linear relationship between the threshold cycle observed and the logarithm of the number of mutant target sequences present in a series of reactions that each contained 10,000 wild-type target sequences present in genomic DNA isolated from cultured normal human cells and either: 10; 30; 100; 300; 1,000; 3,000; or 10,000 mutant target sequences present in genomic DNA isolated from cultured human cancer cells possessing the T790M mutation in the EGFR gene. The dotted line indicates the threshold cycle obtained for a reaction that contained 10,000 wild-type target sequences and no DNA from cancer cells.

Example 10 reports another variation, this time utilizing EGFR mutation T790M and PCR amplification using genomic DNA with up to 10,000 copies of the wild-type target template, and a 24-14-4:1:1 multi-part primer. FIG. 15 is a graph of $C_T$ versus the log of the starting number of intended mutant target templates. As can be seen from FIG. 15, this assay provided a $\Delta C_T$ of 12.6 cycles between a sample containing $10^4$ WT templates and a sample containing $10^4$ MUT templates in the presence of $10^4$ WT templates.

Figure 16:
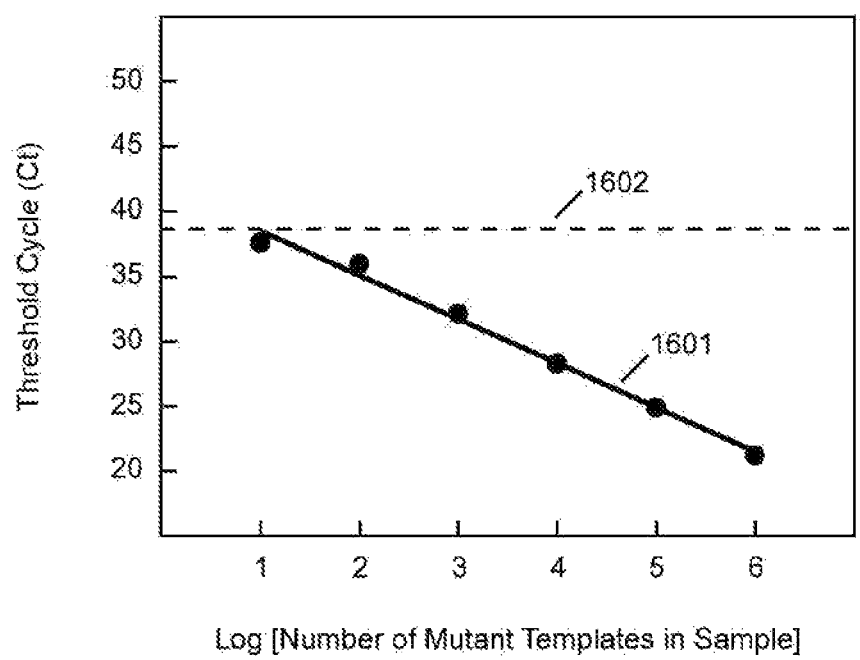
FIG. 16 shows the results of an experiment that is similar to the experiment whose results were shown in FIG. 9, except that an Applied Biosystems PRISM 7700 spectrofluorometric thermal cycler was used to carry out the experiment, instead of a Bio-Rad IQ5 spectrofluorometric thermal cycler.

Example 11 reports an assay similar to the assay for EGFR mutation L858R in Example 4 using a different spectrafluorometric thermal cycler, the ABI PRISM 7700, the same 24-14-5:1:1 multi-part primer, and plasmid DNA, except that this time the templates were not digested. FIG. 16 is a graph of $C_T$ versus the log of the starting number of intended target templates. As can be seen from FIG. 16, this assay provided a $\Delta C_T$ of 16.4 cycles between a sample containing $10^6$ WT templates and a sample containing $10^6$ MUT templates in the presence of $10^6$ WT templates.

Figure 17:
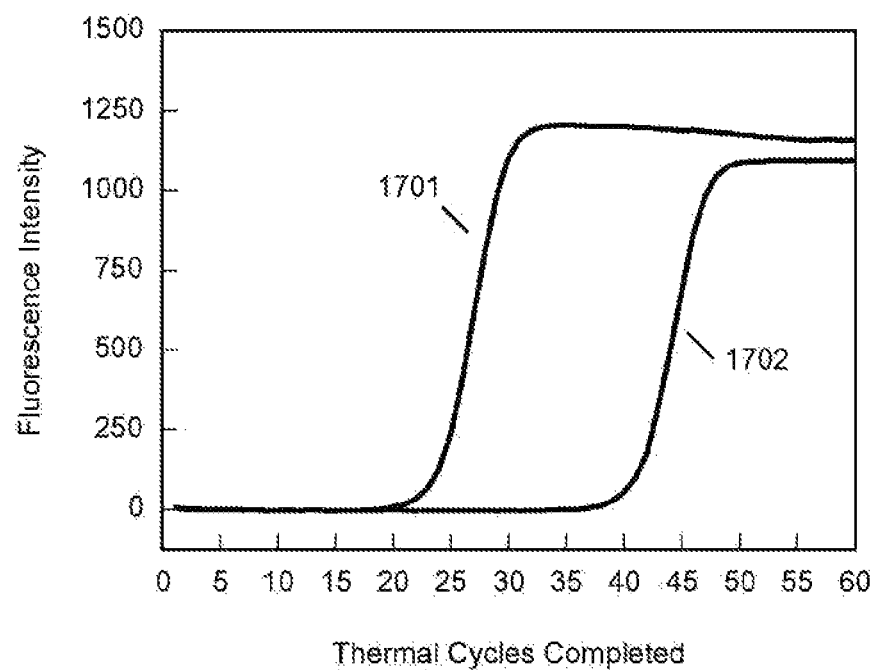
FIG. 17 shows the real-time fluorescence results obtained, panel A, with a multi-part primer according to this invention in reactions containing either 1,000,000 molecules of the primer's intended target sequence or 1,000,000 molecules of the primer's unintended target sequence (where the multi-part primer possessed an interrogating nucleotide at the penultimate position of the foot sequence), and, panel B, with a truncated version of the primer missing the 3'-penultimate and 3'-terminal nucleotides.
Figure 17:
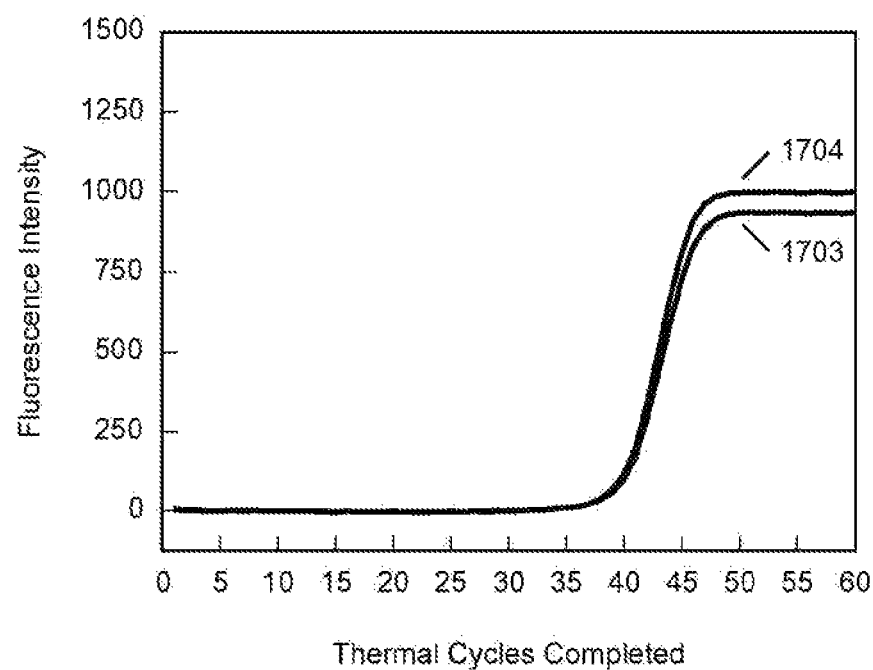

FIG. 17 shows the results of an experiment described in Example 12. The experiment was designed to demonstrate the relative contribution of thermodynamic considerations compared to enzymatic (ARMS-type) considerations in determining the selectivity of the multi-part primers described herein. What we did was to repeat the assay of Example 3 using not only the 24-14-5:1:1 primer, but also a truncated 24-14-5:0:0 primer that omitted the 3'-penultimate and terminal nucleotides. Thus, the foot sequence of the latter primer was perfectly complementary to both the intended target sequence and the unintended target sequence. FIG. 17, panel A, compares the amplification of 1,000,000 intended target sequences to the amplification of 1,000,000 unintended target sequences with the 24-14-5:1:1 multi-part primer whose foot/target hybrid is destabilized at the 3' end, as is done with ARMS, as well as thermodynamics, to discriminate between the two types of templates. The $C_T$ values for primer 24-14-5:1:1 were 23.1 for the intended target sequence (curve 1701) and 40.7 for the unintended target sequence (curve 1702), giving a $\Delta C_T$ of 17.6 cycles.

FIG. 17, panel B, compares the amplification of 1,000,000 intended target sequences to the amplification of 1,000,000 unintended target sequences with the 24-14-5:0:0 primer whose foot/target hybrid is not destabilized at the 3' end. The $C_T$ values for primer 24-14-5:0:0 were 39.7 for the intended target sequence and 39.4 for the unintended target sequence, giving a $\Delta C_T$ of −0.3 cycles.

Like truncated primer 24-14-5:0:0, multi-part primer 24-14-5:1:1 forms a foot hybrid with the same five nucleotides in the wild-type template (curve 1702), because this primer's interrogating nucleotide is not complementary to the single-nucleotide polymorphism, and the resulting mismatched base pair at the penultimate position of the foot sequence prevents the adjacent 3'-terminal nucleotide of this primer's foot sequence from forming an isolated base pair. There is a difference, however, between the hybrid formed by primer 24-14-5:0:0 with the wild-type template and the hybrid formed by primer 24-14-5:1:1 with the wild-type template, and that difference is that the foot sequence in the hybrid formed by primer 24-14-5:1:1 with the wild-type template has two overhanging nucleotides caused by the 3'-penultimate mismatch, and is therefore subject to ARMS-type discrimination by DNA polymerase, whereas the truncated foot sequence in the hybrid formed by primer 24-14-5:0:0 with the wild-type template does not have any overhanging 3'-terminal base pairs, and is therefore not subject to ARMS-type discrimination by DNA polymerase. If ARMS-type discrimination plays a significant role in selectivity when multi-part primers according to this invention are utilized, we would have expected that the $C_T$ value of the reaction involving primer 24-14-5:0:0 with wild-type templates (curve 1704) would have been lower (i.e., less delayed) than the $C_T$ value of the reaction involving primer 24-14-5:1:1 with wild-type templates (curve 1702), because ARMS-type discrimination cannot play a role in the reaction involving primer 24-14-5:0:0 with wild-type templates, but can play a discriminatory role in the reaction involving primer 24-14-5:1:1 with wild-type templates. These results suggest that the role of ARMS-type discrimination is absent, or significantly diminished, when multi-part primers according to this invention are utilized (perhaps as a result of the extremely short mean persistence time of the foot hybrids formed by these highly selective nucleic acid amplification primers).

Assays according to this invention may include screening assays looking for the presence of any rare target when one of multiple possible rare targets may be present. For such assays a multi-part primer is used for each possible rare target, but detection need not identify which target is present. Therefore, SYBR Green dye can be used as the detection reagent, as can a dual-labeled hybridization probe that signals indiscriminately, as can a 5' functional sequence on the primers that signals indiscriminately. Assays that employ multi-part primers according to this invention include amplification and detection, which may include quantitation, of two or more rare target sequences simultaneously in a single reaction tube, reaction well, or other reaction vessel, where one needs to identify which target or targets are present. The amplification and detection in a single reaction tube of two or more rare target sequences that do not have sequence homology and are located in different positions in a genome (for example the simultaneous detection of rare single-nucleotide polymorphisms located in different genes) may include for each different intended target sequence, a specific, uniquely colored, hybridization probe, such as a molecular beacon probe, a ResonSense® probe, or a 5'-nuclease (TaqMan®) probe that hybridizes to a unique sequence in either strand of the amplified product downstream from the multi-part primer. This applies not only to free-floating detector probes, but also to tethered probes such as molecular beacon probe 409 in FIG. 4. Alternatively, the multi-part primer for each different target sequence may include a labeled hairpin, such as hairpin 404 in FIG. 4. Referring to FIG. 4, two or more different multi-part primers 103, each specific for a different rare intended target sequence, and each labeled with a uniquely colored fluorescent label 408, 413, or 416, can be used to simultaneously identify and quantitate each intended target sequence present in an individual sample.

5. Multiplex Assays

An especially attractive feature of SuperSelective primers of this invention is their potential use in multiplex assays that simultaneously measure the abundance of different rare mutant sequences in the same clinical sample. The results of these assays can provide patient-specific information to tailor therapy for each individual.

An intriguing multiplex labeling strategy is based on the realization that, because there is no relation between the bridge sequence and the intended target sequence, assay designers are free to select a distinctly different bridge sequence for each of the different SuperSelective primers that are simultaneously present in a multiplex assay. Since the entire sequence of each primer becomes an integral part of the amplicon that is generated when that primer binds to its mutant target, the distinctive nucleic acid sequence of the bridge segment can serve as a "serial number" within that amplicon that identifies the mutant target from which it was generated.

These identifying bridge sequences can be relatively long (e.g., 20 nucleotides in length to assure their uniqueness), and the primers can be designed to form correspondingly short intervening sequences within the template. To simultaneously detect and quantitate different mutant target sequences that are present in a clinical sample, a set of specific molecular beacon probes (Tyagi et al., (1996) Nat. Biotechnol. 14, 303-308, Tyagi et al., (1998) Nat. Biotechnol., 16, 49-53, and Bonnet et al., (1999) Proc. Natl. Acad. Sci. USA, 96, 6171-6176) can be included in the real-time, gene amplification reactions, each specific for the complement of the distinctive bridge sequence of one of the SuperSelective primers, and each labeled with a differently colored fluorophore.

In these reactions, we prefer that the concentration of the SuperSelective forward primers should be limited, and the linear reverse primers should be present in excess, thereby assuring that the reactions will not be symmetric, and that the molecular beacons will be able to bind to virtually all of the target amplicons that are synthesized in excess, without significant competition from less abundant complementary amplicons (Pierce et al., (2005) Proc. Natl. Acad. Sci. USA, 102, 8609-8614). These multiplex assays can even distinguish different mutations that occur in the same codon, since a SuperSelective primer designed to detect a particular mutation will discriminate against a neighboring or alternative mutation in the same way that it discriminates against a wild-type target sequence.

Figure 18:
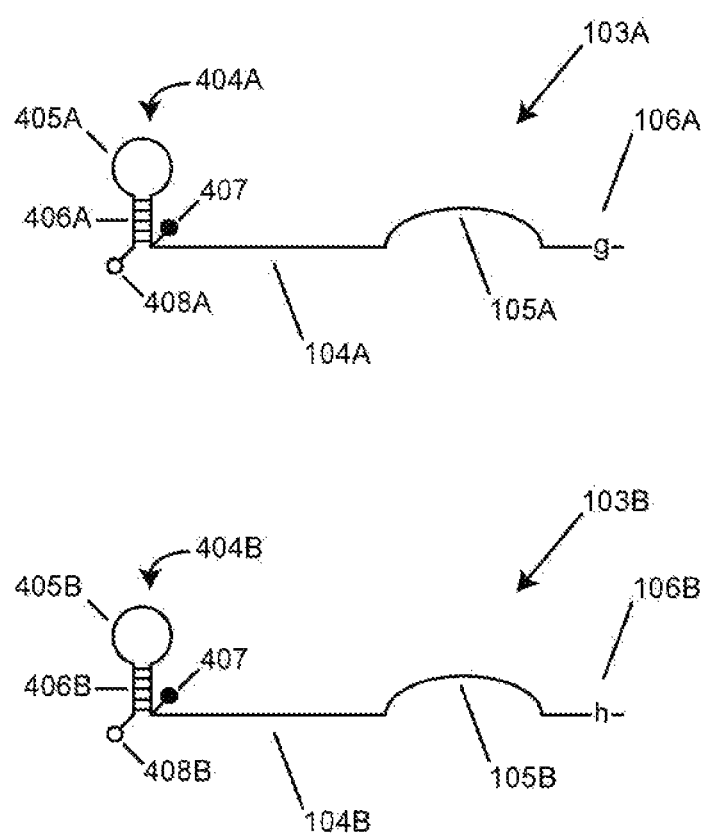
FIG. 18 is a schematic representation of two multi-part primers according to this invention that may be used in a multiplex reaction for two closely related intended target sequences.

Another multiplex strategy is shown in FIG. 18, which is a schematic representation of two multi-part primers according to this invention that may be used in a multiplex reaction for two closely related intended target sequences.

Where there is sequence homology between or among intended target sequences in a multiplex assay, a unique sequence can be introduced by utilizing for each different intended target sequence a unique bridge sequence. As explained above in connection with FIG. 2, the reverse primer copies the entire forward (multi-part) primer into the reverse product strand, so in subsequent cycles of amplification the entire multi-part primer (anchor sequence, bridge sequence, and foot sequence) is complementary to the product made by extension of the reverse primer. In multiplex assays it is important that only one multi-part primer, the "correct" primer that was so copied, hybridizes to and primes that reverse product strand. It will be appreciated that, therefore, one must make the bridge sequence of the "correct" multi-part primer sufficiently distinct to prevent another multi-part primer from priming that reverse product strand (so-called "cross hybridization"). That having been done, a specific, uniquely colored hybridization probe, free-floating or tethered to the primer, that is targeted against the complement of the bridge sequence will signal amplification of only one intended target and will not signal falsely by hybridizing to the multi-part primer itself. Similarly, only the "correct" multi-part primer with a uniquely colored hairpin tail (hairpin 405 in FIG. 4) will hybridize to the reverse product strand and signal, For distinguishing and quantitating the occurrence of different rare target sequences that are almost identical (differing from each other by only one or two single-nucleotide polymorphisms) and which occur very close to each other within a genome (for example, medically significant variants of the human K-ras gene, in which different single-nucleotide polymorphisms can occur within codon 12, each specifying the identity of a different amino acid in that gene's encoded protein), two or more multi-part primers can be utilized that possess the structure outlined in FIG. 18 or in FIG. 19. Turning first to FIG. 18, the top structure 103A shows a multi-part primer whose foot sequence 106A is perfectly complementary to a specific intended rare target sequence, including the nucleotide in that target sequence that corresponds to complementary nucleotide "g" (the interrogating nucleotide). The lower structure 103B shows a multi-part primer whose foot sequence 106B is perfectly complementary to a different specific rare intended target sequence that is a variant of the target for foot 106A and which is located at (or very close to) the position in the genome of the intended target sequence for foot 106A. In foot sequence 106B, nucleotide "h" is the interrogating nucleotide that is perfectly complementary to the corresponding nucleotide in the intended target sequence of foot 106B. In order to be able to simultaneously distinguish, or distinguish and quantitate the abundance of each of these rare target sequences in the same reaction, primer 103A can be linked to a unique structure 404A, that differs in sequence 405A and 406A and fluorophore label 408A, from sequence 405B and 406B and fluorophore label 408B in structure 404B of primer 103B. When two or more multipart primers, such as primers 103A and 103B, are used simultaneously for distinguishing and quantitating similar intended rare target sequences at the same (or at a very similar location), it is often the case that their respective anchor sequences will be identical or very similar (in order to cause the primers to bind to the desired location close to where the variant sequences to be distinguished occur). However, since there is no relation between a bridge sequence of a multi-part primer of this invention and its intended target sequence, bridge sequence 105A in primer 103A can be chosen so that its nucleotide sequence is different from bridge sequence 105B in primer 103B. Here is how two or more multi-part primers of this invention can be utilized simultaneously to distinguish and quantitate rare intended target sequences that are alleles of each other and are located at the same (or very similar position) in a genome:

Extension of reverse primer 203 (FIG. 2) continues through labeled structures 404A and 404B, separating quencher 407 from fluorophore labels 408A and 408B, respectively. As a result, primers 103A and 103B will each fluoresce in their unique identifying color when they are incorporated into amplicons, if their fluorescence intensity is measured in real-time at the end of each chain elongation cycle (in an amplification reaction in which the amplicons become double-stranded, such as in PCR amplifications). Alternatively, primers 103A and 103B will each fluoresce in their unique identifying color when their fluorescence intensity is measured at the end of the annealing stage of an amplification reaction, because their quencher group 407 becomes separated from their fluorophore label (408A or 408B) as a consequence of each primer (103A or 103B) binding to its fully complementary sequence at the 3' end of those amplicon strands 204 (FIG. 2) whose synthesis was initiated by the incorporation of the same primer.

Figure 19:
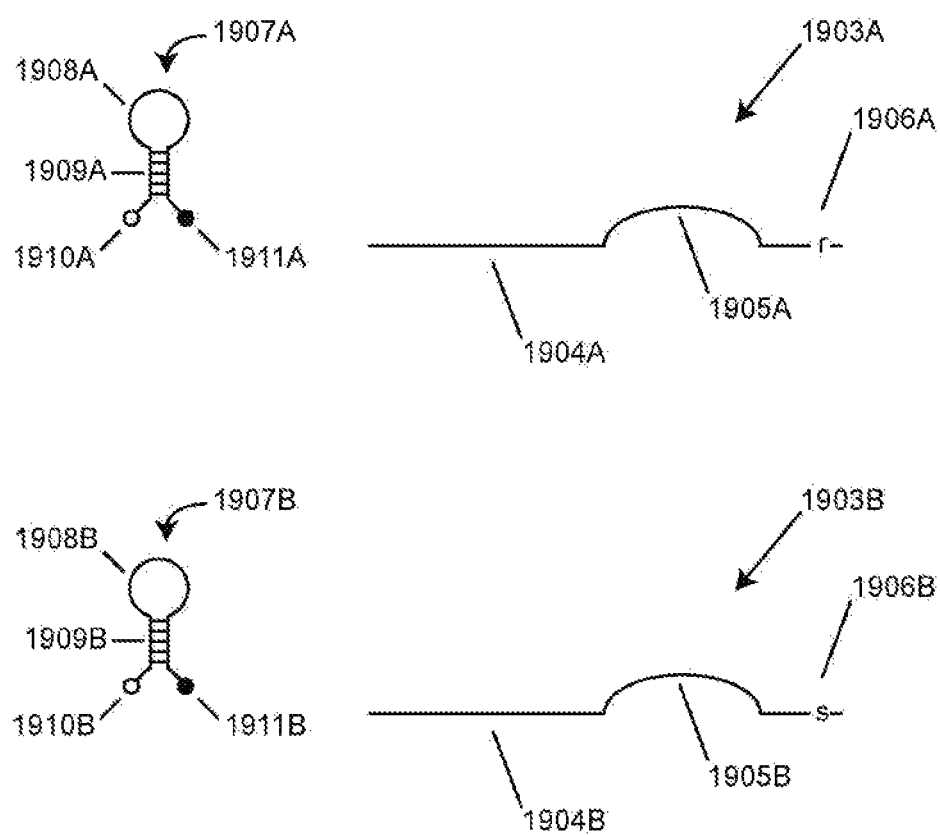
FIG. 19 is a schematic representation of two multi-part primers and two molecular beacon probes that may be used in a multiplex reaction for two closely related intended target sequences.

FIG. 19 describes primers and probes for a similar assay utilizing free-floating molecular beacon probes rather than labeled hairpin tails. In FIG. 19 multi-part primer 1903A has foot sequence 1906A that is perfectly complementary to a specific first intended rare target sequence, including interrogating nucleotide "r". Multi-part primer 1903B has foot sequence 1906B that is perfectly complementary to a different specific second rare target sequence that is a variant of the target for foot sequence 1906A and which is located at (or very close to) the position in the genome of the intended target sequence of foot 1906A. In foot sequence 1906B, nucleotide "s" is the interrogating nucleotide. In this embodiment interrogating nucleotide "r" is not complementary to either to the second rare target sequence or to the wild-type sequence. And interrogating nucleotide "s" is not complementary either to the first rare target sequence or to the wild-type sequence. In order to be able to distinguish amplification products of the two rare target sequences in the same reaction, as well as to prevent cross hybridization, the sequence of bridge 1905A is made quite different from the sequence of bridge 1905B. Molecular beacon probe 1907A, comprised of loop 1908A, stem 1909A, fluorophore 1910A and quencher 1911A, has a loop that is specific for the complement of bridge sequence 1905A. Molecular beacon probe 1907B, comprised of loop 1908B, stem 1909B, fluorophore 1910B and quencher 1911B, has a loop that is specific for the complement of bridge sequence 1905B. Fluorophores 1911A and 1911B are different colors. Detection by probes 1907A and 1907B can be either real time or end point.

The key feature that enables simultaneous real-time measurements to be made of the different amplicons generated from different rare intended allelic target sequences is that the multi-part primers of this invention can be designed to possess quite different sequences in their labeled hairpin tails (for example 404A and 404B) and in their bridge sequences (for example 105A and 105B). Consequently, the annealing conditions can be adjusted to assure that each type of primer only binds to the amplicons whose synthesis was initiated by the same type of primer. Moreover, if a particular type of primer were to bind to a non-cognate amplicon, the signaling hairpin at the end of that primer would not be complementary to the sequence at 3' end of that amplicon, so no fluorescence would occur. As an alternative to simply utilizing different bridge sequences for each multi-part primer that will be simultaneously present in a reaction, different anchor sequences can be utilized by shortening one or sliding it along the target. Alternatively, different lengths for the bridge sequences (such as 105A and 105B) would enable the use of different anchor sequences (such as 104A and 104B) without significantly altering the selectivity of each primer. This will lower the probability of formation of a mismatched hybrid between primer 103A and non-cognate amplicons containing the priming sequence for primer 103B, as well as lowering the probability of formation of a mismatched hybrid between primer 103B and non-cognate amplicons containing the priming sequence for primer 103B.

6. Additional Considerations for Design of Multi-Part Primers

Design of multi-part primers according to this invention is straightforward. We recommend that design be for a particular amplification protocol on a particular instrument, as instruments vary particularly in their detection and presentation of fluorescence. A suitable procedure is to choose a design (anchor length, bridge length, and foot length, with the interrogating nucleotide located at either the 3'-terminal nucleotide or at the penultimate nucleotide from the 3' end of the foot. Then, by simply varying the bridge sequence length and the foot sequence length, in a few trials one can optimize the primer design to achieve the desired large $\Delta C_T$ between a sample containing intended target and a sample containing unintended target. This involves making the primer inefficient for amplifying the intended target sequence. Considerations for design are those discussed above relative to the Examples. In particular, shortening the foot sequence and increasing the size of the bubble formed by the bridge sequence and the target's intervening sequence increase the delay in $C_T$ with the intended target and increases the $\Delta C_T$ between a sample containing intended target and a sample containing unintended target.

There are additional considerations in designing multi-part primers of this invention. The primer must not prime other sequences that are, or may be, present in the sample. Conventional computer methods for preventing that are well known and readily available.

a. Anchor Sequence

The anchor sequence is usually (but not necessarily) perfectly complementary to the template sequence, and it usually can be located approximately 14 nucleotides from the 5' end of the foot sequence and can usually be 15-40, 15-30 or 20 to 30 (such as 20 to 24) nucleotides in length.

Its length is chosen so that the melting temperature of the hybrid that it forms with the template will be in a suitable range, such as 66° C. to 72° C. in several of the Examples. If it turns out that the anchor sequence in a multi-part primer designed to discriminate against a particular polymorphism is not sufficiently specific because its target sequence is present elsewhere in the genome, this problem may be solved by designing a multi-part primer that discriminates against the same polymorphism, but binds to the complementary target strand.

b. Bridge Sequence

Regarding the bridge sequence, we recommend checking for and, if necessary, eliminating transient hybridization events that may occur if that sequence can form low-Tm hybrids with the target, thereby reducing its effective length. Also, the effect of the bridge can be modified by adjusting the rigidity of the bridge sequence, as different nucleotide sequences have somewhat different rigidities. See Goddard et al. (2000) Phys. Rev. Lett. 85:2400-2403.

In one example, the bridge sequence can be approximately at least 6 (e.g., 7, 8, 9, 10, 11, 12, 13, 14, 15, or 20) nucleotides in length. Its nucleotide sequence can be chosen to ensure that, under annealing conditions: (i) it does not hybridize to the corresponding "intervening sequence" in the template strand (which is located between the foot target sequence and the anchor target sequence); (ii) it does not hybridize to any sequence in the human genome; (iii) it does not form any secondary structures under assay conditions that would effectively shorten its length; and (iv) it does not hybridize to the conventional reverse primer used to prime the synthesis of the complementary template strand. In addition, if the intervening sequence in the template strand might form secondary structures under assay conditions that effectively shorten its length, the length of the bridge sequence can be increased and the length of the intervening sequence can be decreased by a corresponding number of nucleotides (accomplished by selecting an anchor target sequence that is closer to the foot target sequence by the same number of nucleotides).

The realization that the bridge sequence can be chosen to be relatively short or relatively long, and the realization that the probe designer can chose any arbitrary sequence for the bridge segment, opens up a plethora of functional possibilities for the design of the SuperSelective primers of this invention.

For example, if the sequence of a putative intervening sequence that occurs naturally in the template is such that it might form a secondary structure under assay conditions, the primer can be designed so as to create a relatively small intervening sequence in the primer-template hybrid, thereby disrupting the formation of the secondary structure, and the primer's bridge sequence can be chosen to be of a relatively longer length, thereby preserving the selectivity of the assay (see the results shown in Table 4). Moreover, primer function can be fine-tuned, by selecting a sequence for the bridge that takes into account differences in the flexibility of the intervening sequence and the bridge sequence.

Furthermore, the choice of an appropriate bridge sequence for a SuperSelective primer apparently suppresses the occurrence of false amplicons, such as primer-dimers. Unlike the design of conventional linear primers (whose sequence is determined by the template to which it binds), an arbitrary sequence is used for the bridge segment. We take care to select a bridge sequence that: (i) does not form secondary structures; (ii) is unrelated to the sequence of the template, the sequence of the genomic DNA, and the sequence of the conventional reverse primer; and that, (iii) when incorporated into the full-length primer, does not enable primer self-hybridization.

c. Role of the Bubble Formed By the Bridge Sequence and the Intervening Sequence Within the acceptable ranges described above, the greater the circumference of the bubble formed by the hybridization of a SuperSelective primer to an original template molecule, the greater is the suppression of wild-type amplicon synthesis relative to the suppression of mutant amplicon synthesis (see for example, FIG. 11). From a thermodynamic point of view, larger bubbles should reduce the equilibrium abundance of both the wild-type hybrids and the mutant hybrids, but should not alter their relative abundance. However, from a kinetic point of view, it is appropriate to consider the forces that impinge upon the bubble that connects the foot hybrid to the target hybrid, because the bubble is subject to random Brownian motions of the water molecules in the reaction mixture. This creates a force that has the potential to pull the foot hybrids apart. The greater the circumference of the bubble, the greater is this potentially disruptive force. Moreover, mismatched wild-type hybrids, which are weaker than perfectly complementary mutant hybrids, are more likely to be pulled apart.

Thus, mismatched wild-type hybrids, not only exist for a shorter length of time due to their lower stability, they are also more easily pulled apart by the random forces that impinge on the bubble. We therefore believe that the extraordinary selectivity of SuperSelective primers arises from both thermodynamic factors that affect hybrid stability, and from kinetic factors that affect the mean persistence time of the resulting hybrids.

d. Foot Sequence

The foot sequence is located at the 3' end of the primer; it is complementary to the region of the template strand where there is at least one nucleotide difference between the intended target sequence and its closely related unintended target sequence such as a single-nucleotide polymorphism is located; and it is usually seven nucleotides in length. The "interrogating nucleotide" in the foot sequence may be located at the penultimate position from the 3' end of the foot sequence, or at the 3' end of the foot sequence. The length of the foot sequence can be modified to improve selectivity. The foot sequence can be shorter (six or even five nucleotides in length), especially if it has a high G-C content. If the interrogating nucleotide would form a G:T base pair with the wild-type template strand, it is desirable to design the primer so that it binds to the complementary template strand, instead.

If the foot sequence is hybridized to the target sequence, and if the DNA polymerase is able to form a functional complex with that hybrid before the hybrid falls apart, then the extension of the foot sequence can be catalyzed by the DNA polymerase to generate an amplicon. It will be appreciated that short foot sequences, for example, 6 or 7 nucleotides in length, generally are so short that they are complementary to sequences that occur at a large number of different locations within the nucleic acids that may be present in a sample being tested, for example in genomic DNA from human cells. However, the foot sequence is so short, and consequently has a melting temperature, Tm, that is so extremely low under the conditions used for amplification, such as the conditions that are used in PCR assays, that the foot sequence will not form a hybrid with any perfectly complementary sequence in the nucleic acid sample being tested, unless the anchor sequence of the primer has first hybridized to a location within the nucleic acid being tested that is only a few nucleotides away from the desired target sequence.

Once designed in the manner disclosed herein, primer sequences can be examined with the aid of any suitable computer program, such as the OligoAnalyzer computer program (Integrated DNA Technologies, Coralville, Iowa), to ensure that under assay conditions they are unlikely to form internal hairpin structures or self-dimers, and to ensure that they do not form heterodimers with the conventional reverse primers.

7. Kits

This invention further includes reagent kits containing reagents for performing the above-described amplification methods, including amplification and detection methods. To that end, one or more of the reaction components for the methods disclosed herein can be supplied in the form of a kit for use in the detection of a target nucleic acid. In such a kit, an appropriate amount of one or more reaction components is provided in one or more containers or held on a substrate (e.g., by electrostatic interactions or covalent bonding).

The kit described herein includes one or more of the primers described above. The kit can include one or more containers containing one or more primers of the invention. A kit can contain a single primer in a single container, multiple containers containing the same primer, a single container containing two or more different primers of the invention, or multiple containers containing different primers or containing mixtures of two or more primers. Any combination and permutation of primers and containers is encompassed by the kits of the invention The kit also contains additional materials for practicing the above-described methods. In some embodiments, the kit contains some or all of the reagents, materials for performing a method that uses a primer according to the invention. The kit thus may comprise some or all of the reagents for performing a PCR reaction using the primer of the invention. Some or all of the components of the kits can be provided in containers separate from the container(s) containing the primer of the invention. Examples of additional components of the kits include, but are not limited to, one or more different polymerases, one or more primers that are specific for a control nucleic acid or for a target nucleic acid, one or more probes that are specific for a control nucleic acid or for a target nucleic acid, buffers for polymerization reactions (in 1× or concentrated forms), and one or more dyes or fluorescent molecules for detecting polymerization products. The kit may also include one or more of the following components: supports, terminating, modifying or digestion reagents, osmolytes, and an apparatus for detecting a detection probe.

The reaction components used in an amplification and/or detection process may be provided in a variety of forms. For example, the components (e.g., enzymes, nucleotide triphosphates, probes and/or primers) can be suspended in an aqueous solution or as a freeze-dried or lyophilized powder, pellet, or bead. In the latter case, the components, when reconstituted, form a complete mixture of components for use in an assay.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: reagents (including buffers) for lysis of cells, divalent cation chelating agents or other agents that inhibit unwanted nucleases, control DNA for use in ensuring that primers, the polymerase and other components of reactions are functioning properly, DNA fragmenting reagents (including buffers), amplification reaction reagents (including buffers), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in amplification or detection of target nucleic acids. In some embodiments, the kits can further include instructions to use the components in any of the methods described herein, e.g., a method using a crude matrix without nucleic acid extraction and/or purification.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like).

8. Additional Definitions

As used herein, the term "target nucleic acid" or "target sequence" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid. A template may be a purified or isolated nucleic acid, or may be non-purified or non-isolated.

As used herein the term "amplification" and its variants includes any process for producing multiple copies or complements of at least some portion of a polynucleotide, said polynucleotide typically being referred to as a "template." The template polynucleotide can be single stranded or double stranded. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotide capable of being incorporated into an extension product during amplification, i.e., DNA, RNA, or a derivative if DNA or RNA, which may include a label.

"Hybridization" or "hybridize" or "anneal" refers to the ability of completely or partially complementary nucleic acid strands to come together under specified hybridization conditions (e.g., stringent hybridization conditions) in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

The term "stringent hybridization conditions" or "stringent conditions" means conditions in which a probe or oligomer hybridizes specifically to its intended target nucleic acid sequence and not to another sequence. Stringent conditions may vary depending well-known factors, e.g., GC content and sequence length, and may be predicted or determined empirically using standard methods well known to one of ordinary skill in molecular biology (e.g., Sambrook, J. et al., 1989, Molecular Cloning, A Laboratory Manual, 2nd ed., Ch. 11, pp. 11.47-11.57, (Cold Spring Harbor Laboratory Press, Cold Spring Harbor, N.Y.)).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Examples

Example 1: EGFR Mutation L858R and a Conventional Linear Primer

Two PCR amplification and detection assays were carried out using as a template either a plasmid DNA containing EGFR mutation L858R or a plasmid DNA containing the corresponding wild-type sequence, which differed from each other by a single-nucleotide polymorphism. Conventional forward and reverse primers were used to generate a double-stranded amplification product 49 nucleotides long. The forward primer (FP) was a conventional primer, containing the interrogating nucleotide near the middle of the primer sequence. The reverse primer (RP) was a conventional primer that was perfectly complementary to both target sequences. The primer sequences and the intended target sequence possessing the mutant allele (MUT), were as follows:

```
FP:
                                              (SEQ ID No. 1)
5'-ATTTTGGGCGGGCCAAACTGC-3'

MUT:
                                              (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

(SEQ ID No. 3)
RP: 5'-GCATGGTATTCTTTCTCTTCCGCA-3'
```

In the forward primer sequence, the nucleotide that is complementary to the mutant target template, but mismatched to the wild-type template, is bold, underlined, and larger. In the mutant target sequence, the binding site for the forward primer is underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 µM; [Nat]=60 mM; [Mg$^{2+}$]=3 mM; [dNTPs]=0.25 mM), the calculated Tm of the forward primer bound to the mutant allele is 67.5° C., and the calculated Tm for the reverse primer is 64.0° C.

Plasmids were prepared by inserting a 115 base pair EGFR gene fragment, containing either the EGFR L858R mutation or the corresponding EGFR wild-type sequence, into a pGEM-11Zf(+) vector (Promega). Mutant and wild-type plasmid DNAs were digested with the restriction endonuclease Mse I (New England Biolabs). The digestion mixture contained 10 units Mse I and 4 µg of mutant or wild-type genomic DNA in a 20-µl volume that contained 5 mM KAc, 2 mM Tris-Ac (pH 7.9), 1 mM MgAc, 1% bovine serum albumin, and 100 µM dithiothreitol. The reactions were incubated for 120 min at 37° C., followed by an incubation for 20 min at 65° C. to inactivate the enzyme.

PCR amplifications were performed in a 30-µl volume containing 50 mM KCl, 10 mM Tris-HCl (pH 8.0), 3 mM $MgCl_2$, 1.5 Units AmpliTaq Gold DNA polymerase (Life Technologies), 250 µM each of the four deoxyribonucleoside triphosphates (dNTPs), 60 nM of each primer, and 1×SYBR® Green (Life Technologies). In this series, reaction mixtures contained either $10^6$ copies of the mutant template (MUT) or $10^6$ copies of wild-type template (WT). Amplifications were carried out using 0.2 ml polypropylene PCR tubes (white) in a Bio-Rad IQ5 spectrofluorometric thermal cycler. The thermal-cycling profile was 10 min at 95° C., followed by 60 cycles of 94° C. for 15 sec, 60° C. for 15 sec, and 72° C. for 20 sec. SYBR® Green fluorescence intensity was measured at the end of each chain elongation stage (72° C.).

Real-time fluorescence results, that is, SYBR Green® fluorescence intensity as a function of the number of amplification cycles completed, are shown in FIG. 5, where curve 501 is the reaction containing $10^6$ MUT templates and curve 502 is the reaction containing $10^6$ WT templates. The assay instrument automatically calculates the threshold cycle ($C_T$) for each reaction. These values were 20.0 (curve 501) and 19.7 (curve 502). In the upper left-hand corner of the graph is a schematic representation of the conventional forward primer (straight line) with the interrogating nucleotide (circle) in the middle.

Example 2: EGFR Mutation L858R and a Conventional Linear Primer with a 3'-Terminal Interrogating Nucleotide A PCR amplification and detection assay was carried out using the mutant (MUT) and wild-type (WT) templates described in Example 1. In this experiment, the forward primer is an "ARMS Primer," that is, a primer perfectly complementary to the mutant template, but possessing a 3'-terminal mismatch to the WT template, that is, possessing an interrogating nucleotide at the 3' end of the priming sequence. We used the same reverse primer as in Example 1. The primer sequences and the intended target sequence possessing the mutant allele (MUT), were as follows:

FP:
(SEQ ID No. 4)
5'-CAAGATCACAGATTTTGGGCG-3'

MUT:
(SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

RP:
(SEQ ID No. 3)
5'-GCATGGTATTCTTTCTCTTCCGCA-3'

In the forward primer sequence, the nucleotide that is complementary to the mutant target template, but mismatched to the wild-type template, is bolded, underlined, and larger. In the mutant target sequence, the binding site for the forward primer is underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 µM; [Nat]=60 mM; [$Mg^{2+}$]=3 mM; [dNTPs]=0.25 mM), the calculated Tm of the forward primer bound to the mutant allele is 60.7° C., and the calculated Tm for the reverse primer is 64.0° C.

Figure 6:
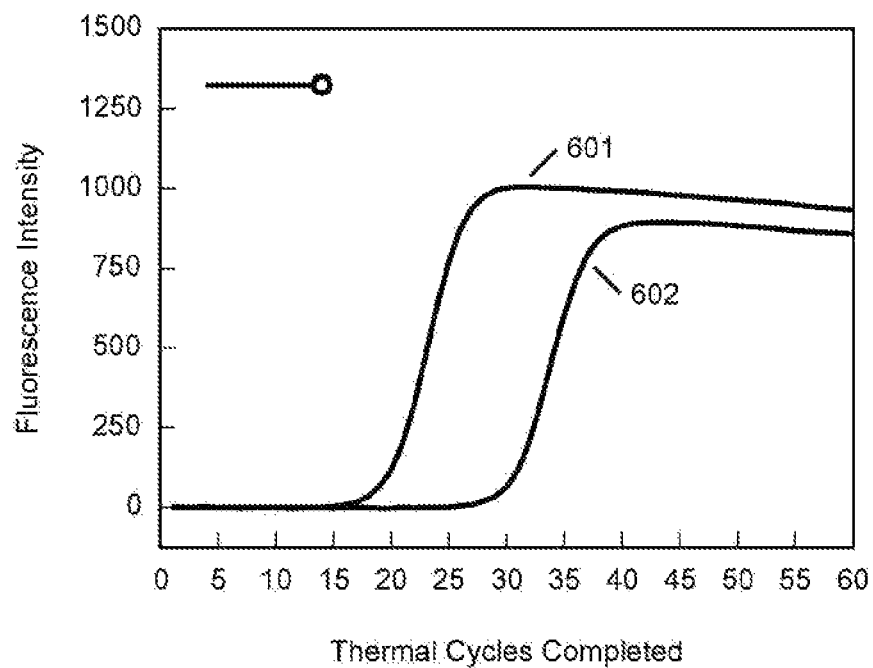
FIG. 6 shows the real-time fluorescence results obtained with an ARMS primer and either 1,000,000 intended target sequences or 1,000,000 unintended, mismatched target sequences differing by a single nucleotide, where the "interrogating nucleotide" in the primer (which is complementary to the corresponding nucleotide in the intended target sequence, but not complementary to the corresponding nucleotide in the unintended target sequence) is the 3'-terminal nucleotide of the primer; and the figure also shows the results obtained with a similar primer where the interrogating nucleotide is at the penultimate nucleotide from the 3' end of the primer.
Figure 6:
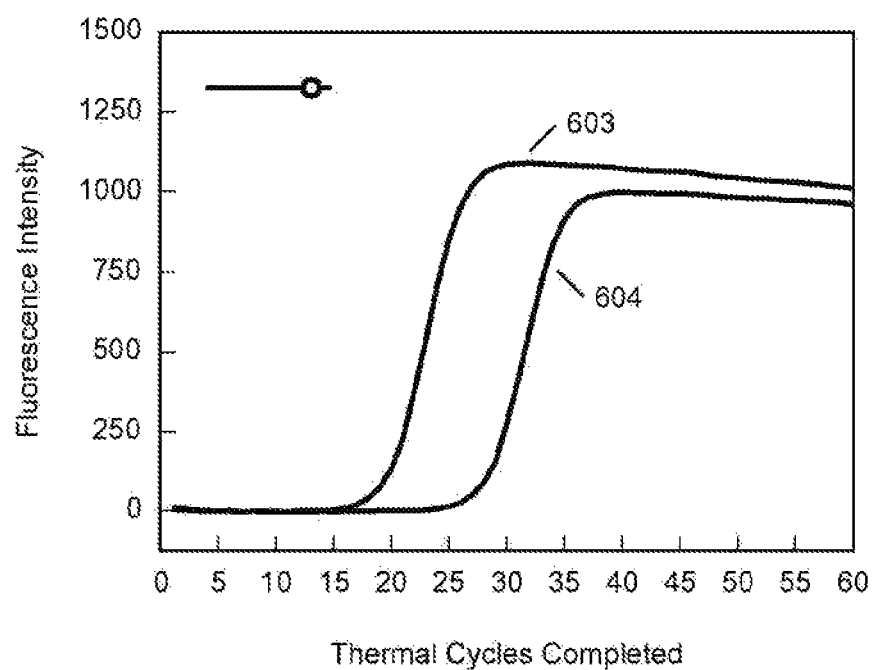

PCR amplification was carried out as described in Example 1. Real-time fluorescence results, that is, SYBR Green® fluorescence intensity as a function of the number of amplification cycles completed, are shown in FIG. 6, Panel A, where curve 601 is the reaction starting with $10^6$ MUT templates and curve 602 is the reaction starting with $10^6$ WT templates. The assay instrument automatically calculates the threshold cycle ($C_T$) for each curve. Those values were 19.4 (curve 601) and 30.4 (curve 602), resulting in a $\Delta C_T$ of 11 cycles. In the upper left-hand corner of the graph is a schematic representation of the conventional forward primer (straight line) with the interrogating nucleotide (circle) located at the 3' end of the primer.

The experiment described above was repeated with a forward primer that possessed the interrogating nucleotide at the penultimate position from its 3' end (we added a G to the 3' end of the primer and removed the 5'-terminal C to maintain primer length). The sequence of the resulting forward primer was:

FP:
(SEQ ID No. 5)
5'-AAGATCACAGATTTTGGGCGG-3'

Using Integrated DNA Technologies' SciTools program, and the same reaction conditions described above, the calculated Tm of the forward primer bound to the mutant allele was 61.9° C.

Real-time fluorescence results, that is, SYBR Green® fluorescence intensity as a function of the number of amplification cycles completed, are shown in FIG. 6, Panel B, where curve 603 is the reaction starting with $10^6$ MUT templates and curve 604 is the reaction starting with $10^6$ WT templates. The machine-calculated $C_T$ values were 19.1 (curve 603) and 27.8 (curve 604), resulting in a $\Delta C_T$ of 8.8 cycles. In the upper left-hand corner of the graph is a schematic representation of the conventional forward primer (straight line) with the interrogating nucleotide (circle) located at the penultimate position from the 3' end of the primer.

Example 3: EGFR Mutation L858R and a 24-14-5:1:1 Multi-Part Primer (Real-Time Data)

Two PCR amplification and detection assays were carried out using the mutant (MUT) and wild-type (WT) template described in Example 1. In this experiment, the forward primer (FP) is a multi-part primer according to this invention. We used the same reverse primer as in Example 1.

In our nomenclature, the multi-part primer used in this example is referred to as a 24-14-5:1:1 primer, referring to an anchor sequence that is 24 nucleotides long, a bridge sequence that is 14 nucleotides long, and a foot sequence that is seven nucleotides long (comprising, from the 5' end of the foot, five nucleotides complementary to both the MUT and WT targets, one interrogating nucleotide that is not complementary to the corresponding nucleotide in the WT target, but that is complementary to the corresponding nucleotide in the MUT target, and, finally, one nucleotide complementary to both targets. Because the interrogating nucleotide is located one nucleotide inboard of the 3' end of the primer, we refer to this nucleotide as being located at the "3'-penultimate position." Comparing the bridge sequence to the region of the target sequence lying between the binding sequence of the anchor and the binding sequence of the foot, which we call the "intervening sequence," one sees that the intervening sequence in this example is fourteen nucleotides long, the same length as the bridge sequence. The sequence of the bridge sequence is chosen so that it is not complementary to the intervening sequence, in order to prevent the hybridization of the bridge sequence to the intervening sequence during primer annealing. Instead of annealing to each other, the bridge sequence and the intervening sequence form a single-stranded "bubble" when both the anchor sequence and the foot sequence are hybridized to the template. The "circumference of the bubble" is defined as the sum of the number of nucleotides in the bridge sequence plus the number of nucleotides in the intervening sequence plus the anchor sequence's 3' nucleotide and its complement plus the foot sequence's 5'-terminal nucleotide and its complement. Consequently, the circumference of the bubble formed by the binding of the multi-part primer in this example to the template molecules used in this example is 14+14+2+2, which equals 32 nucleotides in length.

The primer sequences and the intended target sequence possessing the mutant allele (MUT), were as follows:

```
Primer 24-14-5:1:1 Anchor Bridge Foot
FP:
                                        (SEQ ID No. 6)
5'-CTGGTGAAAACACCGCAGCATGTCGCACGAGTGAGCCCTGGGC

GG-3'

MUT:
                                        (SEQ ID No. 2)
3'-CCTTGCATGACCACTTTTGTGGCGTCGTACAGTTCTAGTGTCTAAA

ACCCGCCCGGTTTGACGACCCACGCCTTCTCTTTCTTATGGTACGTCT

T-5'

RP:
                                        (SEQ ID No. 3)
5'-GCATGGTATTCTTTCTCTTCCGCA-3'
```

In the multi-part forward primer, the bridge sequence is underlined, and the interrogating nucleotide in the foot sequence is bolded, underlined, and larger. In the mutant target sequence, the binding sequence for the forward primer's anchor and for the forward primer's foot are underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 μM; [Nat]=60 mM; [$Mg^{2+}$]= 3 mM; [dNTPs]=0.25 mM), the Tm for the binding of the anchor sequence to a template is 66.9° C., and the Tm for the binding of the entire multi-part primer to the resulting complementary amplicon is 79.9° C.

Figure 7:
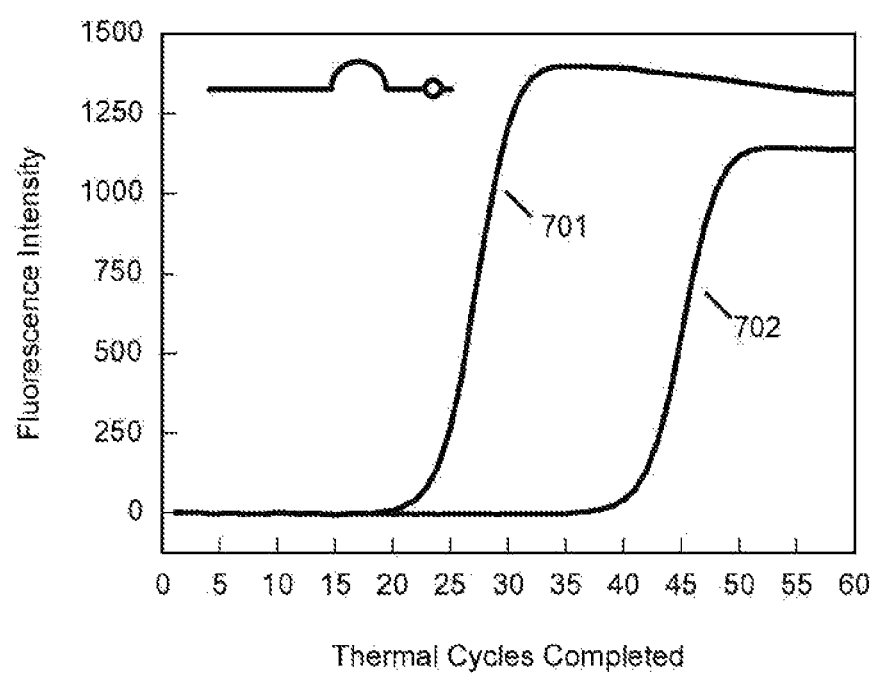
FIG. 7 shows the real-time fluorescence results obtained with a multi-part primer according to this invention in reactions containing either 1,000,000 molecules of the primer's intended target sequence or 1,000,000 molecules of the primer's unintended target sequence (where the multi-part primer possessed an interrogating nucleotide at the penultimate position of the foot sequence).

PCR amplifications were carried out as described in Example 1. Real-time fluorescence results, that is, SYBR Green® fluorescence intensity as a function of the number of amplification cycles completed, are shown in FIG. 7, where curve 701 is the reaction starting with $10^6$ MUT templates and curve 702 is the reaction starting with $10^6$ WT templates. The assay instrument automatically calculates the threshold cycle ($C_T$) for each reaction. These values were 22.9 (curve 701) and 41.1 (curve 702), resulting in a $\Delta C_T$ of 18.2 cycles. In the upper left-hand corner of the graph is a schematic representation of the multi-part primer (the bridge sequence being the semicircle) with the interrogating nucleotide (circle) located at the penultimate position from 3' end of the primer.

Example 4: EGFR Mutation L858R and a 24-14-5:1:1 Multi-Part Primer (Selective Amplification)

A series of PCR amplification and detection assays was carried out using the same multi-part primer, reverse primer, intended target (MUT), and unintended target (WT) described in Example 3. The amplifications were carried out as described in Example 3. Real-time fluorescence results, that is, SYBR Green® fluorescence intensity as a function of the number of amplification cycles completed, are shown in FIG. 8, where curve 801 is the reaction starting with $10^6$ WT templates, and curves 802-807 are the dilution series where each reaction contained $10^6$ WT templates plus either $10^6$, $10^5$, $10^4$, $10^3$, $10^2$, or $10^1$ MUT templates, respectively. The assay instrument automatically calculates the threshold cycle ($C_T$) for each reaction. Those values were 41.1 (curve 801), 23.3 (curve 802), 26.8 (curve 803), 30.5 (curve 804), 33.8 (curve 805), 37.0 (curve 806), and 39.2 (curve 807). In the upper left-hand corner of the graph is a schematic representation of the multi-part primer (the bridge sequence being the semicircle) with the interrogating nucleotide (circle) located at the penultimate position from 3' end of the primer.

FIG. 9 is a graph of the $C_T$ values observed for each reaction that contained MUT templates (obtained from curves 802 through 807 in FIG. 8) as a function of the logarithm of the number of MUT templates present in that reaction. Line 901 is a linear correlation fit to the data points. Dashed line 902 identifies the $C_T$ value for the amplification initiated with $10^6$ WT templates and no MUT templates.

Example 5: EGFR Mutation L858R and the Effect of Decreasing the Multi-part Primer Foot Length The experiment described in Example 4 was repeated using the same 24-14-5:1:1 primer (SEQ. ID No. 6) possessing a foot sequence that is seven-nucleotides long; and also using two additional multi-part primers of the same design, except that the foot sequence of one of the additional primers was one nucleotide longer (24-14-6:1:1), and the foot sequence of the other additional primer was one nucleotide shorter (24-14-4:1:1). In all three cases, the anchor sequence was 24 nucleotides long, the bridge sequence was 14 nucleotides long, and the target's intervening sequence was 14 nucleotides long, creating a bubble circumference of 32 nucleotides in all cases. Furthermore, in all three cases, the interrogating nucleotide was located at the 3'-penultimate position in the foot of the primer. Primer sequences and their intended target sequence (MUT), were as follows:

```
Primer 24-14-4:1:1 Anchor Bridge Foot
FP:
                                         (SEQ ID No. 7)
5'-TGGTGAAAACACCGCAGCATGTCACACGAGTGAGCCCCGGGCGG-3'

MUT:
                                         (SEQ ID No. 2)
3'-CCTTGCATGACCACTTTTGTGGCGTCGTACAGTTCTAGTGTCTAAA

ACCCGCCCGGTTTGACGACCCACGCCTTCTCTTTCTTATGGTACGTCT

T-5'

Primer 24-14-5:1:1 Anchor Bridge Foot
FP:
                                         (SEQ ID No. 6)
5'-CTGGTGAAAACACCGCAGCATGTCGCACGAGTGAGCCCTGGGCG

G-3'

MUT:
                                         (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-6:1:1 Anchor Bridge Foot
FP:
                                         (SEQ ID No. 8)
5'-ACTGGTGAAAACACCGCAGCATGTTGGAGCTGTGAGCCTTGGGCG

G-3'

MUT:
                                         (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Reverse Primer
RP:
                                         (SEQ ID No. 3)
5'-GCATGGTATTCTTTCTCTTCCGCA-3'
```

In the multi-part forward primers, the bridge sequence is underlined, and the interrogating nucleotide in the foot sequence is bolded, underlined, and larger. In the mutant target sequence, the binding sequence for the forward primer's anchor and for the forward primer's foot are underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 μM; [Nat]=60 mM; [Me]=3 mM; [dNTPs]=0.25 mM); the Tm for the binding of the 24-14-4:1:1 anchor sequence to a template is 68.1° C., and the Tm for the binding of the entire multi-part primer to the resulting complementary amplicon is 80.3° C.; the Tm for the binding of the 24-14-5:1:1 anchor sequence to a template is 66.9° C., and the Tm for the binding of the entire multi-part primer to the resulting complementary amplicon is 79.9° C.; and the Tm for the binding of the 24-14-6:1:1 anchor sequence to a template is 68.1° C., and the Tm for the binding of the entire multi-part primer to the resulting complementary amplicon is 79.4° C.

For each of the three multi-part primer designs, a series of PCR amplification and detection assays was carried out as described in Example 4, utilizing a dilution series starting with $10^6$ WT templates plus $10^6$, $10^5$, $10^4$, $10^3$, $10^2$, or $10^1$ copies of the MUT template, respectively. The assay instrument automatically calculates the threshold cycle ($C_T$) for each reaction. The $C_T$ values calculated from the real-time data for each reaction (not shown) are listed in Table 1, along with the calculated $C_T$ value for reactions initiated with $10^6$ WT templates and no MUT templates.

TABLE 1

| Primer | Threshold Cycles ($C_T$) Observed for Reactions Containing Different Numbers of Intended Targets | | | | | | |
|---|---|---|---|---|---|---|---|
|  | $10^6$ | $10^5$ | $10^4$ | $10^3$ | $10^2$ | $10^1$ | 0 |
| 24-14-4:1:1 | 27.5 | 30.7 | 34.2 | 37.1 | 40.3 | 44.6 | 42.0 |
| 24-14-5:1:1 | 23.3 | 26.6 | 30.4 | 33.4 | 37.0 | 38.8 | 41.1 |
| 24-14-6:1:1 | 21.2 | 24.6 | 27.9 | 32.0 | 34.9 | 35.6 | 37.5 |

FIG. 10 is a set of graphs showing the $C_T$ values observed (for each set of reactions containing the same primer) as a function of the logarithm of the number of MUT templates present in each reaction. Line 1001 is a linear correlation fit to the $C_T$ values for the primer possessing a six-nucleotide-long foot sequence (4:1:1); line 1002 is a linear correlation fit to the $C_T$ values for the primer possessing a seven-nucleotide-long foot sequence (5:1:1); and line 1003 is a linear correlation curve fit to the $C_T$ values for the primer possessing a seven-nucleotide-long foot sequence (6:1:1). When the 24-14-6:1:1 primer was used, the lower abundance MUT template samples gave $C_T$ values that occurred somewhat earlier than predicted, suggesting the presence of a few obscuring amplicons generated from the abundant WT templates in the sample.

These results demonstrate that the use of a multi-part primer possessing a shorter foot sequence, such as primer 24-14-5:1:1, reduces this problem, and the use of a primer possessing the shortest foot sequence, such as primer 24-14-4:1:1, virtually eliminates this problem, enabling the detection and quantitation of as few as 10 intended template molecules in the presence of 1,000,000 unintended template molecules.

Example 6: EGFR Mutation L858R and the Effect of Increasing the Multi-Part Primer Bubble Circumference The experiment described in Example 4 was repeated using the same 24-14-5:1:1 primer (SEQ. ID No. 6) possessing a bridge sequence 14-nucleotides long that creates an intervening sequence when hybridized to its template that is also 14-nucleotides long; and also using two additional multi-part primers of the same design, except that the bridge sequence of one of the additional primers was 18-nucleotides long (24-18-5:1:1), and the bridge sequence of the other additional primer was 10-nucleotides long (24-10-5:1:1). In all three cases, the anchor sequence was 24-nucleotides long, the foot sequence was 5:1:1, and the choice of the anchor sequence was such that the intervening sequence created when the primer binds to its template was the same length as the primer's bridge sequence. Consequently, the bubble circumferences formed by this series of three multi-part primers are 24, 32, and 40 nucleotides in length, respectively. Furthermore, in all three cases, the interrogating nucleotide was located at the 3'-penultimate position in the foot of the primer. Primer sequences and the intended target sequence (MUT), were as follows:

Primer 24-10-5:1:1 Anchor Bridge Foot
FP:
(SEQ ID No. 10)
5'-TGAAAACACCGCAGCATGTCAAGACACTCAGCCCTGGGCGG-3'

MUT:
(SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-5:1:1 Anchor Bridge Foot
FP:
(SEQ ID No. 6)
5'-CTGGTGAAAACACCGCAGCATGTCGCACGAGTGAGCCCTGGGCG

G-3'

MUT:
(SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-18-5:1:1 Anchor Bridge Foot
FP:
(SEQ ID No. 9)
5'-CGTACTGGTGAAAACACCGCAGCACTGACGACAAGTGAGCCCTGGGC

GG-3'

MUT:
(SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Reverse Primer
RP:
(SEQ ID No. 3)
5'-GCATGGTATTCTTTCTCTTCCGCA-3'

In the multi-part forward primers, the bridge sequence is underlined, and the interrogating nucleotide in the foot sequence is bolded, underlined, and larger. In the mutant target sequence, the binding sequence for the forward primer's anchor and for the forward primer's foot are underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 µM; [Nat]=60 mM; [Mg$^{2+}$]=3 mM; [dNTPs]=0.25 mM); the Tm for the binding of the 24-10-5:1:1 anchor sequence to a template is 66.3° C., and the Tm for the binding of the entire multi-part primer to the resulting complementary amplicon is 78.0° C.; the Tm for the binding of the 24-14-5:1:1 anchor sequence to a template is 66.9° C., and the Tm for the binding of the entire multi-part primer to the resulting complementary amplicon is 79.9° C.; and the Tm for the binding of the 24-18-5:1:1 anchor sequence to a template is 67.9° C., and the Tm for the binding of the entire multi-part primer to the resulting complementary amplicon is 79.3° C.

For each of the three multi-part primer designs, a series of PCR amplification and detection assays was carried out as described in Example 4, utilizing a dilution series starting with 10$^6$ WT templates plus 10$^6$, 10$^5$, 10$^4$, 10$^3$, 10$^2$, or 10$^1$ copies of the MUT template, respectively. The assay instrument automatically calculates the threshold cycle ($C_T$) for each reaction. The $C_T$ values calculated from the real-time data for each reaction (not shown) are listed in Table 2, along with the calculated $C_T$ value for reactions initiated with 10$^6$ WT templates and no MUT templates.

TABLE 2

| Primer | Threshold Cycles ($C_T$) Observed for Reactions Containing Different Numbers of Intended Targets | | | | | | |
|---|---|---|---|---|---|---|---|
| | 10$^6$ | 10$^5$ | 10$^4$ | 10$^3$ | 10$^2$ | 10$^1$ | 0 |
| 24-10-5:1:1 | 20.0 | 24.3 | 27.3 | 30.8 | 33.5 | 35.2 | 35.0 |
| 24-14-5:1:1 | 23.3 | 26.6 | 30.4 | 33.4 | 37.0 | 38.8 | 41.1 |
| 24-18-5:1:1 | 25.8 | 30.6 | 33.2 | 36.4 | 42.0 | 45.2 | 43.9 |

FIG. 11 is a set of graphs showing the $C_T$ values observed (for each set of reactions containing the same primer) as a function of the logarithm of the number of MUT templates present in each reaction. Line 1101 is a linear correlation fit to $C_T$ values for the primer that forms a bubble with a circumference that is 24-nucleotides long; line 1102 is a linear correlation fit to $C_T$ values for the primer that forms a bubble with a circumference that is 32-nucleotides long; and line 1103 is a linear correlation fit to $C_T$ values for the primer that forms a bubble with a circumference that is 40-nucleotides long. Similar to what occurred with primers possessing longer foot sequences, when the 24-10-5:1:1 primer, which forms a relatively small bubble, was used, the lower abundance MUT template samples gave $C_T$ values that occurred somewhat earlier than predicted, suggesting the presence of a few obscuring amplicons generated from the abundant WT templates in the sample.

These results demonstrate that the use of a multi-part primer that forms a larger bubble, such as primer 24-14-5:1:1, reduces this problem, and the use of a primer that forms the largest bubble, such as primer 24-18-5:1:1, virtually eliminates this problem, enabling the detection and quantitation of as few as 10 intended template molecules in the presence of 1,000,000 unintended template molecules.

Example 7: EGFR Mutation L858R and the Effect of Varying the Position of the Interrogating Nucleotide within the Foot Sequence of a Multi-Part Primer The experiment described in Example 3 was repeated using the same 24-14-5:1:1 primer (SEQ. ID No. 6) which includes a seven-nucleotide-long foot sequence in which the interrogating nucleotide is located at the penultimate position from the 3' end of the primer, and also using five additional multi-part primers of the same design, except that the position of the interrogating nucleotide with the foot sequence was varied. In all six cases, the anchor sequence was 24-nucleotides long, the bridge sequence was 14-nucleotides long, and the foot sequence was 7-nucleotides long. Primer sequences and the intended target sequence (MUT), were as follows:

Primer 24-14-6:1:0 Anchor Bridge Foot
FP:
(SEQ ID No. 11)
5'-ACTGGTGAAAACACCGCAGCATGTTGCACGAGTGAGCCTTGGGC

G-3'

MUT:
(SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

-continued

```
Primer 24-14-5:1:1 Anchor Bridge Foot
FP:
                                        (SEQ ID No. 6)
5'-CTGGTGAAAACACCGCAGCATGTCGCACGAGTGAGCCCTGGGCG

G-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-4:1:2 Anchor Bridge Foot
FP:
                                        (SEQ ID No. 12)
5'-TGGTGAAAACACCGCAGCATGTCACACGAGTGAGCCACGGGCGG

G-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-3:1:3 Anchor Bridge Foot
FP:
                                        (SEQ ID No. 13)
5'-GGTGAAAACACCGCAGCATGTCAAACGAGTGAGCCACAGGCGGG

C-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-2:1:4 Anchor Bridge Foot
FP:
                                        (SEQ ID No. 14)
5'-GTGAAAACACCGCAGCATGTCAAGGAAGTGAGCCACAAGCGGGC

C-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-1:1:5 Anchor Bridge Foot
FP:
                                        (SEQ ID No. 15)
5'-TGAAAACACCGCAGCATGTCAAGACAGACTGACCCAAACGGGCC

A-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Reverse Primer
RP:
                                        (SEQ ID No. 3)
5'-GCATGGTATTCTTTCTCTTCCGCA-3'
```

In the multi-part forward primers, the bridge sequence is underlined, and the interrogating nucleotide in the foot sequence is bolded, underlined, and larger. In the mutant target sequence, the binding sequence for the forward primer's anchor and for the forward primer's foot are underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 µM; [Nat]=60 mM; [Mg$^{2+}$]= 3 mM; [dNTPs]=0.25 mM); the Tm for the binding of the 24-14-6:1:0 anchor sequence to a template is 67.9° C., and the Tm for the binding of the entire multi-part primer to the resulting complementary amplicon is 79.0° C.; the Tm for the binding of the 24-14-5:1:1 anchor sequence to a template is 66.9° C., and the Tm for the binding of the entire multi-part primer to the resulting complementary amplicon is 79.9° C.; the Tm for the binding of the 24-14-4:1:2 anchor sequence to a template is 68.1° C., and the Tm for the binding of the entire multi-part primer to the resulting complementary amplicon is 80.0° C.; the Tm for the binding of the 24-14-3:1:3 anchor sequence to a template is 67.0° C., and the Tm for the binding of the entire multi-part primer to the resulting complementary amplicon is 78.9° C.; the Tm for the binding of the 24-14-2:1:4 anchor sequence to a template is 65.6° C., and the Tm for the binding of the entire multi-part primer to the resulting complementary amplicon is 78.2° C.; and the Tm for the binding of the 24-14-1:1:5 anchor sequence to a template is 66.6° C., and the Tm for the binding of the entire multi-part primer to the resulting complementary amplicon is 78.1° C.

PCR amplifications were carried out as described in Example 1. Real-time fluorescence results, that is, SYBR Green® fluorescence intensity as a function of the number of amplification cycles completed, are shown in the six panels of FIG. 12, where each panel identifies the multi-part primer that was used. In each panel the odd-numbered curve is the results obtained for a sample begun containing $10^6$ MUT templates, and the even-numbered curve is the results obtained for a sample containing $10^6$ WT templates. Table 3 lists the machine-calculated $C_T$ values for both targets with each primer, and also shows the difference ($\Delta C_T$).

TABLE 3

Threshold Cycles ($C_T$) Observed for Reactions Containing Primers whose Interrogating Nucleotide is Located at Different Positions in the Foot Sequence

| Primer | $10^6$ MUT Templates | $10^6$ WT Templates | $\Delta C_T$ |
|---|---|---|---|
| 24-14-6:1:0 | 24.3 | 43.1 | 18.8 |
| 24-14-5:1:1 | 22.9 | 41.1 | 18.2 |
| 24-14-4:1:2 | 21.2 | 36.1 | 14.9 |
| 24-14-3:1:3 | 23.0 | 35.2 | 12.2 |
| 24-14-2:1:4 | 23.1 | 33.2 | 10.1 |
| 24-14-1:1:5 | 21.1 | 30.4 | 9.3 |

Example 8: EGFR Mutation L858R and the Effect of Varying Multi-Part Primer Bubble Symmetry The experiment described in Example 3 was repeated using the same 24-14-5:1:1 primer (SEQ. ID No. 6), which forms a symmetrical bubble that includes its 14-nucleotide-long bridge sequence and a 14-nucleotide-long intervening sequence from the template; and the experiment also used four additional multi-part primers that form different asymmetric bubbles with the mutant target (SEQ ID No. 2). By "asymmetric bubble," we mean a bubble formed by a bridge sequence and an intervening sequence in the template that have different lengths. In this experiment, all of the multi-part primers that were compared had an anchor sequence 24-nucleotides long, a 5:1:1 foot sequence, and a different-length bridge sequence (which were 18, 16, 14, 12, or 10 nucleotides in length). For each multi-part primer, the identity of the anchor sequence was selected so that the sum of the length of the bridge sequence plus the length of the intervening sequence (formed by the binding of both the anchor sequence and the foot sequence to the template) equals 28. Consequently, the circumference of the bubble formed by each of these five multi-part primers was always the same. The aim of the experiment was to determine whether or not the formation of an asymmetrical bubble affects the selectivity of the primer. Primer sequences and the intended target sequence (MUT) were as follows:

```
Primer 24-18/10-5:1:1 Anchor Bridge Foot
FP:
                                        (SEQ ID No. 16)
5'-TGAAAACACCGCAGCATGTCAAGACACACGACAAGTGAGCCCTGGGC
GG-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-16/12-5:1:1 Anchor Bridge Foot
FP:
                                        (SEQ ID No. 17)
5'-GGTGAAAACACCGCAGCATGTCAATCCAACAAGTGAGCCCTGGGCG
G-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14/14-5:1:1 Anchor Bridge Foot
FP:
                                        (SEQ ID No. 6)
5'-CTGGTGAAAACACCGCAGCATGTCGCACGAGTGAGCCCTGGGCG
G-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-12/16-5:1:1 Anchor Bridge Foot
FP:
                                        (SEQ ID No. 18)
5'-TACTGGTGAAAACACCGCAGCATGGACGACGAGCCCTGGGCG
G-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'
```

```
-continued
Primer 24-10/18-5:1:1 Anchor Bridge Foot
FP:
                                        (SEQ ID No. 19)
5'-CGTACTGGTGAAAACACCGCAGCACTGACGGCCCTGGGCGG-3'

MUT:
                                        (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Reverse Primer
RP:
                                        (SEQ ID No. 3)
5'-GCATGGTATTCTTTCTCTTCCGCA-3'
```

In the multi-part forward primers, the bridge sequence is underlined, and the interrogating nucleotide in the foot sequence is bolded, underlined, and larger. In the mutant target sequence, the binding sequence for the forward primer's anchor and for the forward primer's foot are underlined, and the sequence of the reverse primer is underlined. In addition, in the mutant target sequence, the nucleotide specific to the mutant is bolded, underlined, and larger. Using Integrated DNA Technologies' SciTools program for calculating the melting temperatures of DNA hybrids (specifying parameters: [oligo]=0.06 µM; [Nat]=60 mM; [Mg$^{2+}$]=3 mM; [dNTPs]=0.25 mM); the Tm for the binding of the 24-18/10-5:1:1 anchor sequence to a template is 66.3° C., and the Tm for the binding of the entire multi-part primer to the resulting complementary amplicon is 79.1° C.; the Tm for the binding of the 24-16/12-5:1:1 anchor sequence to a template is 67.0° C., and the Tm for the binding of the entire multi-part primer to the resulting complementary amplicon is 78.5° C.; the Tm for the binding of the 24-14/14-5:1:1 anchor sequence to a template is 66.9° C., and the Tm for the binding of the entire multi-part primer to the resulting complementary amplicon is 79.9° C.; the Tm for the binding of the 24-12/16-5:1:1 anchor sequence to a template is 66.3° C., and the Tm for the binding of the entire multi-part primer to the resulting complementary amplicon is 79.5° C.; and the Tm for the binding of the 24-10/18-5:1:1 anchor sequence to a template is 67.9° C., and the Tm for the binding of the entire multi-part primer to the resulting complementary amplicon is 79.3° C.

PCR amplifications were carried out as described in Example 1. Real-time fluorescence results, that is, SYBR Green® fluorescence intensity as a function of the number of amplification cycles completed are shown in the five panels of FIG. 13, where each panel identifies the bubble the bubble that can be formed by the length of the bridge sequence and the length of the target's intervening sequence (for example, an "18/10 Bubble" signifies use of forward primer 24-18/10-5:1:1 which can form an intervening sequence with the target that is 10 nucleotides long). In each panel the odd-numbered curve is the results obtained for a sample begun containing 10$^6$ MUT templates, and the even-numbered curve is the results obtained for a sample containing 10$^6$ WT templates. Table 4 lists the machine-calculated $C_T$ values for both targets with each primer, and also shows the difference ($\Delta C_T$).

TABLE 4

Threshold Cycles ($C_T$) Observed for Reactions Containing Primers that Form Bubbles with Varying Symmetries

| Primer | $10^6$ MUT Templates | $10^6$ WT Templates | $\Delta C_T$ |
|---|---|---|---|
| 24-18/10-5:1:1 | 22.8 | 39.3 | 16.5 |
| 24-16/12-5:1:1 | 22.1 | 38.2 | 16.1 |
| 24-14/14-5:1:1 | 22.9 | 41.1 | 18.2 |
| 24-12/16-5:1:1 | 22.5 | 38.4 | 15.9 |
| 24-10/18-5:1:1 | 22.1 | 39.5 | 17.4 |

Example 9: B-raf Mutation V600E

We used the method of Example 4 with a multi-part primer according to this invention targeted to B-raf mutation V600E, which is a single-nucleotide polymorphism. For comparative purposes, we utilized a 24-14-5:1:1 design for the primer. The primer sequences and the intended target sequence (MUT) were as follows:

```
B-raf Primer Anchor Bridge Foot
FP:
                                    (SEQ ID No. 20)
5'-AGACAACTGTTCAAACTGATGGGAAAACACAATCATCTATTTCT
C-3'

MUT:
                                    (SEQ ID No. 21)
3'-GGTCTGTTGACAAGTTTGACTACCCTGGGTGAGGTAGCTCTAAAGAG

ACATCGATCTGGTTTTAGTGGATAAAAA-5'

Reverse Primer
RP:
                                    (SEQ ID No. 22)
5'-ATAGGTGATTTTGGTCTAGC-3'
```

In the multi-part forward primer, the bridge sequence is underlined, and the interrogating nucleotide in the foot sequence is bolded, underlined, and larger. In the mutant target sequence, the binding sequence for the forward primer's anchor and the binding sequence for the forward primer's foot are underlined, and the sequence of the reverse primer is underlined. Using Integrated DNA Technologies' SciTools program for calculating the melting temperatures of DNA hybrids (specifying parameters: [oligo]=0.06 µM; [Nat]=60 mM; [Mg$^2$+]=3 mM; [dNTPs]=0.25 mM), the Tm for the binding of the anchor sequence to a template is 63.5° C., the Tm for the binding of the entire multi-part primer to the resulting complementary amplicon is 71.1° C., and the calculated Tm for the binding of the reverse primer is 56.1° C.

Plasmids were prepared by inserting synthetic oligonucleotides into a pGEM-11Zf(+) vector (Promega) that corresponded to a 116 bp EGFR gene fragment that contained either the B-raf V600E mutation or the B-raf wild-type sequence. Mutant and wild-type plasmid DNA was digested with restriction endonuclease Mse I (New England Biolabs). The digestion mixture contained 10 units Mse I and 4 µg of mutant or wild-type genomic DNA in a 20-µl volume that contained 5 mM KAc, 2 mM Tris-Ac (pH 7.9), 1 mM MgAc, 1% bovine serum albumin, and 100 µM dithiothreitol. The reactions were incubated for 120 min at 37° C., followed by an incubation for 20 min at 65° C. to inactivate the enzyme.

PCR amplifications were performed in a 30-µl volume containing 50 mM KCl, 10 mM Tris-HCl (pH 8.0), 3 mM MgCl$_2$, 1.5 Units AmpliTaq Gold DNA polymerase, 250 µM of each deoxyribonucleoside triphosphate (dNTP), 60 nM of each primer, and 1×SYBR® Green. Amplifications were carried out using 0.2 ml polypropylene PCR tubes (white) in a Bio-Rad IQ5 spectrofluorometric thermal cycler. The thermal-cycling profile was 10 min at 95° C., followed by 60 cycles of 94° C. for 15 sec, 60° C. for 20 sec, and 72° C. for 20 sec. SYBR® Green fluorescence intensity was measured at the end of each chain elongation stage (72° C.).

The PCR amplification and detection assays were carried out, utilizing a dilution series containing $10^6$ WT templates plus $10^6$, $10^5$, $10^4$, $10^3$, $10^2$, or $10^1$ copies of the MUT template, respectively. We also included a sample containing only $10^6$ WT templates. From the real-time fluorescence data (not shown), the assay instrument automatically calculates the threshold cycle ($C_T$) for each reaction. For the B-raf V600E mutant dilution series, those values were 27.7 ($10^6$ MUT templates), 31.1 ($10^5$ MUT templates), 34.1 ($10^4$ MUT templates), 37.6 ($10^3$ MUT templates), 43.0 ($10^2$ MUT templates), 46.9 ($10^1$ MUT templates), and 50.8 ($10^6$ WT templates and no MUT templates). FIG. 14 is a graph of the $C_T$ value observed for each reaction that contained MUT templates, as a function of the logarithm of the number of MUT templates present in that reaction. Line 1401 is a linear correlation fit to the data points. Dashed line 1402 identifies the $C_T$ value for the amplification initiated with $10^6$ WT templates and no MUT templates.

Example 10: EGFR Mutation T790M in Human Genomic DNA

A series of PCR amplification and detection assays was carried out using as templates human genomic DNA containing EGFR mutation T790M (isolated from cell line H1975, which contains the EFGR T790M mutation) and human genomic DNA containing the corresponding wild-type sequence (isolated from human genomic DNA obtained from Coriell Cell Repositories), which differ by a single-nucleotide polymorphism in the EGFR gene. The forward primer was a 24-14-4:1:1 multi-part primer according to this invention. The reverse primer was a conventional linear primer. The primer sequences and the intended target sequence (MUT) were as follows:

```
T790M Primer Anchor Bridge Foot
FP:
                                    (SEQ ID No. 23)
5'-GCCTGCTGGGCATCTGCCTCACCTAATAATCTACAACAATCAT
G-3'

MUT:
                                    (SEQ ID No. 24)
3'-CACGGCGGACGACCCGTAGACGGAGTGGAGGTGGCACGTCGAGTAGT

ACGTCGAGTACGGGAAGCCGACGGAGGACC-5'

Reverse Primer
RP:
                                    (SEQ ID No. 25)
5'-GAGGCAGCCGAAGGGCATGAGC-3'
```

In the multi-part forward primer, the bridge sequence is underlined, and the interrogating nucleotide in the foot sequence is bolded, underlined, and larger. In the mutant target sequence, the binding sequence for the forward primer's anchor and the binding sequence for the forward primer's foot are underlined, and the sequence of the reverse primer is underlined. Using Integrated DNA Technologies'

SciTools program for calculating the melting temperatures of DNA hybrids (specifying parameters: [oligo]=0.06 µM; [Nat]=60 mM; [Mg$^{2+}$]=3 mM; [dNTPs]=0.25 mM), the Tm for the binding of the anchor sequence to a template is 72.5° C., the Tm for the binding of the entire multi-part primer to the resulting complementary amplicon is 73.9° C., and the calculated Tm for the binding of the reverse primer is 68.2° C. Mutant and wild-type human genomic DNAs were digested with restriction endonuclease Mse I. The digestion mixture contained 10 units Mse I and 4 µg of mutant or wild-type genomic DNA in a 20-µl volume that contained 5 mM KAc, 2 mM Tris-Ac (pH 7.9), 1 mM MgAc, 1% bovine serum albumin, and 100 µM dithiothreitol. The reactions were incubated for 120 min at 37° C., followed by incubation for 20 min at 65° C. to inactivate the enzyme.

PCR amplifications were performed in a 20-µl volume containing 50 mM KCl, 10 mM Tris-HCl (pH 8.0), 3 mM MgCl$_2$, 1.0 Unit AmpliTaq Gold DNA polymerase, 250 µM of each deoxyribonucleoside triphosphate (dNTP), 60 nM of each primer, and 1×SYBR® Green. Amplifications were carried out using 0.2 ml polypropylene PCR tubes (white) on a Bio-Rad IQ5 spectrofluorometric thermal cycler. The thermal-cycling profile was 10 min at 95° C., followed by 60 cycles of 94° C. for 15 sec, 55° C. for 15 sec, and 72° C. for 20 sec. SYBR® Green fluorescence intensity was measured at the end of each chain elongation stage (72° C.).

The PCR amplification and detection assays were carried out, utilizing a dilution series containing 10,000 WT templates plus: 10,000; 3,000; 1,000; 300; 100; 30; or 10 copies of the MUT template, respectively. We also included a sample containing only 10,000 WT templates. From the real-time fluorescence data (not shown), the assay instrument automatically calculates the threshold cycle ($C_T$) for each reaction. For this T790M dilution series, those values were 29.2 (10,000 MUT templates), 31.1 (3,000 MUT templates), 32.7 (1,000 MUT templates), 35.5 (300 MUT templates), 38.2 (100 MUT templates), 38.8 (30 MUT templates), 40.7 (10 MUT templates), and 42.8 (10,000 WT templates and no MUT templates). FIG. 15 is a graph of the $C_T$ value observed for each reaction that contained MUT templates, as a function of the logarithm of the number of MUT templates present in that reaction. Line 1501 is a linear correlation fit to the data points. Dashed line 1502 is the $C_T$ value for the amplification initiated with 10,000 WT templates and no MUT templates.

Example 11: EGFR Mutation L858R Quantitated in the Applied Biosystems PRISM 7700 Spectrofluorometric Thermal Cycler An experiment similar to the assay reported in Example 4 was performed to amplify and detect mutation L858R in the EGFR gene, utilizing a different thermal cycling instrument, the Applied Biosystems PRISM 7700 spectrofluorometric thermal cycler. A series of PCR amplification and detection assays was carried out using as templates plasmid DNA containing EGFR mutation L858R and plasmid DNA containing the corresponding wild-type sequence, which differ by a single-nucleotide polymorphism in the EGFR gene. In contrast to the templates used in Example 4, in this experiment, the templates were not digested with a restriction endonuclease. The amplifications were carried out with the same multi-part forward primer and conventional reverse primer as described in Example 3. The primer sequences and the intended target sequence (MUT) were as follows:

Primer 24-14-5:1:1 Anchor Bridge Foot
FP:
(SEQ ID No. 6)
5'-CTGGTGAAAACACCGCAGCATGTC<u>GCACGAGTGAGCCC</u>TGGGC<u>G</u>G-3'

MUT:
(SEQ ID No. 2)
3'-CCTTGCAT<u>GACCACTTTTGTGGCGTCGTACAG</u>TTCTAGTGTCTAAA ACCCGCCCGGTTTGACGACCC<u>ACGCCTTCTCTTTCTTATGGTACGTCT</u>T-5'

RP:
(SEQ ID No. 3)
5'-GCATGGTATTCTTTCTCTTCCGCA-3'

In the multi-part forward primer, the bridge sequence is underlined, and the interrogating nucleotide in the foot sequence is bolded, underlined, and larger. In the mutant target sequence, the binding sequence for the forward primer's anchor and the binding sequence for the forward primer's foot are underlined, and the sequence of the reverse primer is underlined. Using Integrated DNA Technologies' SciTools program for calculating the melting temperatures of DNA hybrids (specifying parameters: [oligo]=0.06 µM; [Nat]=60 mM; [Mg$^{2+}$]=3 mM; [dNTPs]=0.25 mM), the Tm for the binding of the anchor sequence to a template is 66.9° C., the Tm for the binding of the entire multi-part primer to the resulting complementary amplicon is 79.9° C., and the calculated Tm for the binding of the reverse primer is 68.2° C.

PCR amplifications were performed in a 40-µl volume that contained 50 mM KCl, 10 mM Tris-HCl (pH 8.0), 3 mM MgCl$_2$, 2.0 Units AmpliTaq Gold DNA polymerase, 250 µM of each deoxyribonucleoside triphosphate (dNTP), 60 nM of each primer, and 1×SYBR® Green. Amplifications were carried out using 0.2 ml polypropylene PCR tubes (transparent) on the Applied Biosystems PRISM 7700 spectrofluorometric thermal cycler. The thermal-cycling profile was 10 min at 95° C., followed by 55 cycles of 94° C. for 15 sec, 60° C. for 20 sec, and 72° C. for 20 sec. SYBR® Green fluorescence intensity was measured at the end of each chain elongation stage (72° C.).

The PCR amplification and detection assays were carried out, utilizing a dilution series containing 10$^6$ WT templates plus 10$^6$, 10$^5$, 10$^4$, 10$^3$, 10$^2$, or 10$^1$ copies of the MUT template, respectively. We also included a sample containing only 10$^6$ WT templates. From the real-time fluorescence data (not shown), the assay instrument automatically calculates the threshold cycle ($C_T$) for each reaction. Those values were 21.2 (10$^6$ MUT templates), 24.9 (10$^5$ MUT templates), 28.3 (10$^4$ MUT templates), 32.2 (10$^3$ MUT templates), 36.0 (10$^2$ MUT templates), 37.6 (10$^1$ MUT templates) and 38.7 (10$^6$ WT templates and no MUT templates). FIG. 16 is a graph of the $C_T$ value observed for each reaction that contained MUT templates, as a function of the logarithm of the number of MUT templates present in that reaction. Line 1601 is a linear correlation fit to the data points. Dashed line 1602 is the $C_T$ value for the amplification initiated with 10$^6$ WT templates and no MUT templates.

Example 12: Role of ARMS Discrimination when Multi-part Primers Are Utilized in PCR Assays To investigate the functioning of multi-part primers according to this invention, we repeated the experiment described in Example 3, not only with the 24-14-5:1:1 primer described there, but also with a truncated 24-14-5:0:0 primer, that is a primer that had the same anchor sequence, the same bridge sequence and the same five 5' nucleotides of the foot sequence. It lacked the last two 3' nucleotides of the foot sequence. Thus, its foot sequence was perfectly complementary to both the intended, mutant target, and the unintended, wild-type target. Primer sequences and the intended target sequence (MUT), were as follows for reactions utilizing each of these two multi-part primers:

```
Primer 24-14-5:1:1 Anchor Bridge Foot
FP:
                                           (SEQ ID No. 6)
5'-CTGGTGAAAACACCGCAGCATGTCGCACGAGTGAGCCCTGGGCG

G-3'

MUT:
                                           (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Primer 24-14-5:0:0 Anchor Bridge Foot
FP:
                                          (SEQ ID No. 26)
5'-CTGGTGAAAACACCGCAGCATGTCGCACGAGTGAGCCCTGGGC-3'

MUT:
                                           (SEQ ID No. 2)
3'-CCTTGCATGACCACTTTTGTGGCGTCGTACAGTTCTAGTGTCTAA

AACCCGCCCGGTTTGACGACCCACGCCTTCTCTTTCTTATGGTACGTC

TT-5'

Reverse Primer
RP:
                                           (SEQ ID No. 3)
5'-GCATGGTATTCTTTCTCTTCCGCA-3'
```

In the multi-part forward primers, the bridge sequence is underlined, and the interrogating nucleotide in the foot sequence is bolded, underlined, and larger. In the mutant target sequence, the binding sequence for the forward primer's anchor and the binding sequence for the forward primer's foot are underlined, and the sequence of the reverse primer is underlined. Using Integrated DNA Technologies' SciTools program for calculating the melting temperatures of DNA hybrids (specifying parameters: [oligo]=0.06 μM; [Nat]=60 mM; [Mg$^2+$]=3 mM; [dNTPs]=0.25 mM), the Tm for the binding of the anchor sequence of both primers to a template is 66.9° C., the Tm for the binding of primer 24-14-5:1:1 to the resulting complementary amplicon is 79.9° C., and the Tm for the binding of primer 24-14-5:0:0 to the resulting complementary amplicon is 79.0° C.

PCR amplifications were carried out as described in Example 3. Real-time fluorescence results, that is, SYBR Green® fluorescence intensity as a function of the number of amplification cycles completed were recorded for each reaction. FIG. 17, Panel A shows the results obtained for reactions containing primer 24-14-5:1:1, where curve 1701 is the reaction containing 10$^6$ MUT templates and curve 1702 is the reaction containing 10$^6$ WT templates; and FIG. 17, Panel B shows the results obtained for reactions containing primer 24-14-5:0:0, where curve 1703 is the reaction containing 10$^6$ MUT templates and curve 1704 is the reaction containing 10$^6$ WT templates. The assay instrument automatically calculates the threshold cycle ($C_T$) for each curve. The $C_T$ values for primer 24-14-5:1:1 were 23.1 (curve 1701) and 40.7 (curve 1702), giving a $\Delta C_T$ of 17.6 cycles; and the $C_T$ values for primer 24-14-5:0:0 were 39.7 (curve 1703) and 39.4 (curve 1704), giving a $\Delta C_T$ of −0.3 cycles (indicating that these two reactions gave virtually identical results).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

The invention claimed is:

1. An amplification and detection method that is capable of detecting as few as 10 copies of at least one rare, mutant DNA target sequence in a mixture containing, for each mutant target sequence, 100,000 copies of a closely related wild-type DNA target sequence, comprising (a) repeatedly cycling a reaction mixture in a primer-dependent amplification reaction having a primer-annealing temperature, said reaction mixture including said at least one mutant target sequence or its closely related wild-type target sequence or both, a DNA polymerase, other reagents needed for amplification, and for each mutant target sequence a primer pair that includes a multi-part primer comprising, in the 5' to 3' direction the following three contiguous DNA sequences:

an anchor sequence that hybridizes with the mutant target sequence and with its closely related wild-type target sequence during primer annealing;

a bridge sequence at least six nucleotides long that does not hybridize to either the mutant target sequence or its closely related wild-type target sequence during primer annealing; and a foot sequence that is at least five nucleotides long, perfectly complementary to the mutant sequence and mismatched to its wild-type sequence by one or two nucleotides, wherein:

(i) if the anchor sequence and the foot sequence of the primer are hybridized either to the mutant target sequence or to its closely related wild-type target sequence, there is in the target sequence an intervening sequence that does not hybridize to the primer's bridge sequence during primer-annealing, and the bridge sequence and the intervening sequence, together create a bubble in the hybrid having a circumference of 16-52 nucleotides, wherein the intervening sequence is at least six nucleotides long and the bridge sequence has a length equal to or greater than that of the intervening sequence, (ii) the circumference of the bubble and the length of the foot sequence in combination result in a weak foot/mutant-target-sequence hybrid that makes copying the mutant target sequence unlikely, (iii) the bridge sequence and the foot sequence do not together prime non-target sequences in the mixture, and (iv) the probability that during said cycling a multi-part primer/wild-type target sequence hybrid will be extended is at least 10,000 times lower than the probability that during said cycling a multi-part primer/mutant target sequence hybrid will be extended, as evidenced by a $\Delta C_T$ of at least 13.3 cycles; and (b) detecting amplified product or products with a dsDNA binding dye, or for each multi-part primer a fluorescent hybridization probe that signals upon hybridization to the amplification product of the primer, or for each multi-part primer a quenched, fluorescently labeled oligonucleotide hairpin at the primer's 5' end that fluoresces only when incorporated in or hybridized to the primer's amplified product, wherein copying is "unlikely" means that, if the reaction were begun with a reaction mixture containing $10^6$ copies of the at least one mutant DNA target sequence, no wild-type sequence and the multi-part primer, and separately with a reaction mixture containing $10^6$ copies of the at least one mutant DNA target sequence, no wild-type sequence and a corresponding conventional primer in place of the multi-part primer, the threshold cycle ($C_T$) of the reaction utilizing the multi-part primer would be delayed by at least three cycles compared to the $C_T$ of the reaction utilizing the conventional primer.

2. The method of claim 1, wherein the bridge sequence is at least 8 nucleotides long, the intervening sequence is at least 8 nucleotides long, and the bubble has a circumference of 28-52 nucleotides.

3. The method of claim 1, wherein the foot sequence of each multi-part primer is mismatched to its wild-type target is at either or both of the primer's 3' nucleotide and 3' penultimate nucleotide.

4. The method of claim 1, wherein for each of the at least one multi-part primers, the $C_T$ delay for a reaction begun with $10^6$ copies of the mutant DNA target sequence and the multi-part primer as compared to a reaction begun with $10^6$ copies of the mutant DNA target sequence and a conventional primer is at least 5 cycles.

5. The method of claim 4, wherein the threshold cycle ($C_T$) of an assay begun with $10^6$ copies of each mutant target sequence is at least 18 cycles earlier than the $C_T$ of an assay begun with $10^6$ copies of its closely related wild-type target sequence.

6. The method of claim 4, wherein the delay is at least 10 cycles.

7. The method of claim 6, wherein the threshold cycle ($C_T$) of an assay begun with $10^6$ copies of each mutant target sequence is at least 18 cycles earlier than the $C_T$ of an assay begun with $10^6$ copies of its closely related wild-type target sequence.

8. The method of claim 1, wherein the bubble circumference is 28-44 nucleotides.

9. The method of claim 1, wherein the at least one mutant target sequence comprises at least two mutant target sequences that are close to each other in an intended target and share sequence homology, wherein there is a multi-part forward primer for each of said at least two mutant sequences and a common reverse primer, wherein the primer-dependent amplification reaction is non-symmetric with the common reverse primer being the excess primer, wherein each multi-part primer has a different bridge sequence that is sufficiently distinct to prevent cross hybridization, wherein the bubble formed when each multi-part primer is asymmetric, with the bridge sequence being longer than the intervening sequence, and wherein amplified products from each multi-part primer are separately detected.

10. The method of claim 1, wherein each multi-part primer contains a unique functional moiety located 5' to the anchor sequence, said functional group not hybridizing either to the mutant target sequence or to the wild-type target sequence.

11. A kit of reagents for performing amplification and detection according to claim 1, including at least one multi-part primer as defined in claim 1, at least one reverse primer, amplification buffer, dNTPs, DNA polymerase, and at least one detection reagent.

12. The kit according to claim 11, comprising one or more of the following:

(A) at least two multi-part primers, and a unique dual-labeled fluorescent probe for the amplified product of each multi-part primer that signals upon binding to either strand of that amplified product, and (B) a multi-part primer for each of at least two mutant target sequences that are close to each other in an intended target and share sequence homology, and a common reverse primer for said multi-part primers, wherein the primer-dependent amplification reaction is non-symmetric with the common reverse primer being the excess primer, wherein each multi-part primer has a different bridge sequence that is sufficiently distinct to prevent cross hybridization, and wherein the bubble formed when each multi-part primer hybridizes to its intended target sequence is asymmetric, with the bridge sequence being longer than the intervening sequence.

* * * * *